US011240995B2

(12) United States Patent
Shen et al.

(10) Patent No.: US 11,240,995 B2
(45) Date of Patent: Feb. 8, 2022

(54) GENETICALLY MODIFIED NON-HUMAN ANIMAL WITH HUMAN OR CHIMERIC TIM-3

(71) Applicant: Biocytogen Pharmaceuticals (Beijing) Co., Ltd., Beijing (CN)

(72) Inventors: Yuelei Shen, Beijing (CN); Jian Ni, Beijing (CN); Yanan Guo, Beijing (CN); Rui Huang, Beijing (CN); Meiling Zhang, Beijing (CN); Lei Zhao, Beijing (CN); Yang Bai, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/409,656

(22) Filed: May 10, 2019

(65) Prior Publication Data

US 2019/0357506 A1 Nov. 28, 2019

Related U.S. Application Data

(63) Continuation of application No. PCT/CN2017/110494, filed on Nov. 10, 2017.

(30) Foreign Application Priority Data

Nov. 11, 2016 (CN) .......................... 201610994218.2
Nov. 10, 2017 (CN) .......................... 201711103773.2

(51) Int. Cl.
*A01K 67/027* (2006.01)

(52) U.S. Cl.
CPC ...... *A01K 67/0271* (2013.01); *A01K 67/0278* (2013.01); *A01K 2227/105* (2013.01); *A01K 2267/0331* (2013.01)

(58) Field of Classification Search
CPC ............ A01K 67/0275; A01K 67/0278; A01K 2207/15; A01K 2217/072
See application file for complete search history.

(56) References Cited

U.S. PATENT DOCUMENTS

| 4,683,195 A | 7/1987 | Mullis et al. |
| 2015/0106961 A1 | 4/2015 | Rojas et al. |
| 2018/0295818 A1* | 10/2018 | Shiota ...................... C12Q 1/68 |

FOREIGN PATENT DOCUMENTS

| CN | 104561095 | 4/2015 |
| WO | WO 2003/002722 | 1/2003 |
| WO | WO 2016/175285 | 11/2016 |
| WO | WO2018/001241 | 1/2018 |
| WO | WO 2018/041118 | 3/2018 |
| WO | WO2018/041119 | 3/2018 |
| WO | WO 2018/041120 | 3/2018 |
| WO | WO2018/041121 | 3/2018 |
| WO | WO 2018/068756 | 4/2018 |

OTHER PUBLICATIONS

Printout from https://en.wikipedia.org/wiki/Genetically_modified_animal, printed 2020, pp. 1-23 (Year: 2020).*
Robert and Ohta. Dev. Dyn. 238(6):1249-1270, 2009 (Year: 2009).*
Hammer. Avian Pathol 3(2):65-78, 1974, abstract only (Year: 1974).*
Dolatshad et al. Mammalian Genome 26:598-608, 2015 (Year: 2015).*
Yao et al. Scientific Reports 4:6926. DOI:10.1038/srep06926. Nov. 2014. pp. 1-8 (Year: 2014).*
DeAngelis et al. (Journal for ImmunoTherapy of Cancer, (Nov. 2017) vol. 5, Supp. Supplement2. Abstract No. P365. Meeting Info: 32nd Annual Meeting and Pre-Conference Programs of the Society for Immunotherapy of Cancer, SITC 2017. National Harbor, MD, United States. Nov. 8, 2017-Nov. 12, 2017 (Year: 2017).*
Tsao et al. PNAS 101(52):18159-18164, 2004 (Year: 2004).*
GenBank Accession No. JX049979.1, "*Homo sapiens* T-cell immunoglobulin and mucin domain-containing protein 3 mRNA, complete cds," GenBank, May 13, 2012, 2 pages.
GenBank Accession No. HW502107.1, "JP 2014039558-A/9: TIM-3 polypeptides," GenBank, Mar. 6, 2014, 2 pages.
Anderson, "Tim-3: an emerging target in the cancer immunotherapy landscape," Cancer Immunol Res., 2014, 2(5):393-8.
Auerbach et al., "Establishment and Chimera Analysis of 129/SvEv- and C57BL/6-Derived Mouse Embtyonic Stem Cell Lines," BioTechniques, 2000, 29:1024-1032.
Chen et al., "Bioinformatics analysis and construction of eukaryotic expression vector of human TIM-3 gene and its fusion protein," Journal of Clinical Hematology, 2011, 24(10):569-573 (with English abstract).
Festing et al., "Revised nomenclature for strain 129 mice," Mammalian Genome, 1999, 10:836.
Foks et al., "Accession No. NP_599011.2, hepatitis A virus cellular receptor 2 homolog precursor [*Homo sapiens*]," NCBI GenBank, 2015.
International Search Report and Written Opinion in Appln. No. PCT/CN2017/110494, dated Feb. 9, 2018, 12 pages.
Ito et al., "NOD/SCID/ ycnull mouse: an excellent recipient mouse model for engraftment of human cells," Blood, 2002, 100(9):3175-3182.
Wang et al., "Recent studies on the Role of Tim-3 in Immunoregulation," International Journal of Immunology, 2003, 29(2): 107-111 (with English abstract).
Yin et al., "Delivery technologies for genome editing," Nature Reviews Drug Discovery, 2017, 16(6):387-399.
Yuan et al., "Accession No. NP_116171.3, hepatitis A virus cellular receptor 2 homolog precursor [*Homo sapiens*]," NCBI GenBank, 2016.
Lee et al., "Phosphotyrosine-dependent coupling of Tim-3 to T-cell receptor signaling pathways," Molecular and cellular biology, Oct. 1, 2011, 31(19):3963-3974.

(Continued)

*Primary Examiner* — Marcia S Noble
(74) *Attorney, Agent, or Firm* — Fish & Richardson P.C.

(57) ABSTRACT

The present disclosure relates to the genetically modified non-human animals that express a human or chimeric (e.g., humanized) T-cell immunoglobulin and mucin-domain containing-3 (TIM-3), and methods of use thereof.

20 Claims, 25 Drawing Sheets

Specification includes a Sequence Listing.

(56) References Cited

OTHER PUBLICATIONS

PCT International Preliminary Report on Patentability in Appln. No. PCT/CN2017/110494, dated May 23, 2019, 7 pages.

* cited by examiner

| | Score | Expect | Method | Identities | Positives | Gaps |
|---|---|---|---|---|---|---|
| | 337 bits(863) | 3e-121 | Compositional matrix adjust. | 187/292(64%) | 213/292(72%) | 12/292(4%) |

```
Mouse    1   MFSGLTLNCVLLILQLLLLARSLENAYVFEVGKNAYLPCSYTLSTPGALVPMCWGKGFCPW    60
             MFS L  +CVLILL LLL RS E  Y   EVG+NAYLPC YT + PG LVP+CWGKG CP
Human    1   MFSHLPFDCVLLLLLLLTRSSEVEYRAEVGQNAYLPCFYTPAAPGNLVPVCWGKGACPV     60

Mouse    61  SQCTNELLRTDERNVTYQKSSRYQLKGDLNKGDVSLIIKNVTLDDHGTYCCRIQFPGLMN   120
             +C N +LRTDER+V  Y  +SRY L GD  KGDVSL I+NVTL D G YCCRIQ PG+MN
Human    61  FECGNVVLRTDERDVNYW-TSRYWLNGDFRKGDVSLTIENVTLADSGIYCCRIQIPGIMN   119

Mouse    121 DKKLELKLDIKAAKVTPAQTAHGDSTTASPRTLTTERNG-SETQTLVTLHNNNGTKISTW   179
             D+K  LKL IK AKVTPA T   D T A PR LTT  +G +ETQTL +L + N  T+IST
Human    120 DEKFNLKLVIKPAKVTPAPTRQRDFTAAFPRMLTTRGHGPAETQTLGSLPDINLTQISTL   179

Mouse    180 ADEIKDS--------GETIRTAIHIGVGVSAGLTLALIIGVLLILKWYSCKKKKLSSLSL   230
             A+E++DS        G TIR  I+IG G+ AGL LALI G LI KWYS  K+K+ +LSL
Human    180 ANELRDSRLANDLRDSGATIRIGIYIGAGICAGLALALIFGALIFKWYSHSKEKIQNLSL   239

Mouse    231 ITLANLPPGGLANAGAVRIRSEENIYTIEENVYEVENSNEYYCYVNS-QQPS           281
             I+LANLPP GLANA A   IRSEENIYTIEENVYEVE  NEYYCYV+S QQPS
Human    240 ISLANLPPSGLANAVAEGIRSEENIYTIEENVYEVEEPNEYYCYVSSRQQPS           291
```

FIG. 24

GENETICALLY MODIFIED NON-HUMAN ANIMAL WITH HUMAN OR CHIMERIC TIM-3

CLAIM OF PRIORITY

This application claims benefit of PCT/CN2017/110494, which further claims the benefit of Chinese Patent Application App. No. 201610994218.2, filed on Nov. 11, 2016, and Chinese Patent Application App. No. 201711103773.2, filed on Nov. 10, 2017. The entire contents of the foregoing are incorporated herein by reference.

TECHNICAL FIELD

This disclosure relates to genetically modified animal expressing human or chimeric (e.g., humanized) T-cell immunoglobulin and mucin-domain containing-3 (TIM-3), and methods of use thereof.

BACKGROUND

The immune system has developed multiple mechanisms to prevent deleterious activation of T cells. One such mechanism is the intricate balance between positive and negative costimulatory signals delivered to T cells. Targeting the inhibitory pathways for the immune system is considered to be a potential approach for the treatment of various diseases, e.g., cancers, and autoimmune diseases.

The traditional drug research and development for these inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to an animal model with humanized TIM-3. The animal model can express human TIM-3 or chimeric TIM-3 (e.g., humanized TIM-3) protein in its body. It can be used in the studies on the function of TIM-3 gene, and can be used in the screening and evaluation of anti-human TIM-3 antibodies. In addition, the animal models prepared by the methods described herein can be used in drug screening, pharmacodynamics studies, treatments for immune-related diseases (e.g., autoimmune disease), and cancer therapy for human TIM-3 target sites; in addition, they can be used to facilitate the development and design of new drugs, and save time and cost. In summary, this disclosure provides a powerful tool for studying the function of TIM-3 protein and screening for cancer drugs.

Furthermore, the disclosure also provides TIM-3 gene knockout mice. Moreover, the mice described in the present disclosure can be mated with the mice containing other human or chimeric genes (e.g., chimeric CTLA-4, chimeric PD-1, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy. In one aspect, the disclosure relates to genetically-modified, non-human animals whose genome comprises at least one chromosome comprising a sequence encoding a human or chimeric T-cell immunoglobulin and mucin-domain containing-3 (TIM-3). In some embodiments, the sequence encoding the human or chimeric TIM-3 is operably linked to an endogenous regulatory element at the endogenous TIM-3 gene locus in the at least one chromosome. In some embodiments, the sequence encoding a human or chimeric TIM-3 comprises a sequence encoding an amino acid sequence that is at least 50%, 55%, 65%, 70%, 75%, 80%, 85%, 90%, 95%, 99%, or 100% identical to human TIM-3 (NP_116171.3 (SEQ ID NO: 26)). In some embodiments, the sequence encoding a human or chimeric TIM-3 comprises a sequence encoding an amino acid sequence that is at least 50%, 55%, 65%, 70%, 75%, 80%, 85%, 90%, 95%, 99%, or 100% identical to SEQ ID NO: 30. In some embodiments, the sequence encoding a human or chimeric TIM-3 comprises a sequence encoding an amino acid sequence that corresponds to amino acids 22-128 of SEQ ID NO: 26.

In some embodiments, the animal is a mammal, e.g., a monkey, a rodent or a mouse. In some embodiments, the animal is a C57BL/6 mouse. In some embodiments, the animal does not express endogenous TIM-3. In some embodiments, the animal has one or more cells expressing human or chimeric TIM-3. In some embodiments, the animal has one or more cells expressing human or chimeric TIM-3, and the expressed human or chimeric TIM-3 can bind to or interact with human protein GALECTIN-9 and/or HMGB1. In some embodiments, the animal has one or more cells expressing human or chimeric TIM-3, and the expressed human or chimeric TIM-3 can bind to or interact with endogenous GALECTIN-9 and/or HMGB1.

In one aspect, the disclosure relates to genetically-modified, non-human animals, wherein the genome of the animals comprises a replacement, at an endogenous TIM-3 gene locus, of a sequence encoding a region of endogenous TIM-3 with a sequence encoding a corresponding region of human TIM-3. In some embodiments, the sequence encoding the corresponding region of human TIM-3 is operably linked to an endogenous regulatory element at the endogenous TIM-3 locus, and one or more cells of the animal expresses a chimeric TIM-3. In some embodiments, the animal does not express endogenous TIM-3. In some embodiments, the region of endogenous TIM-3 is the extracellular region of TIM-3. In some embodiments, the animal has one or more cells expressing a chimeric TIM-3 having an extracellular region, a transmembrane region, and a cytoplasmic region, wherein the extracellular region comprises a sequence that is at least 50%, 60%, 70%, 80%, 90%, 95%, or 99% identical to the extracellular region of human TIM-3. In some embodiments, the extracellular region of the chimeric TIM-3 has a sequence that has at least 10, 20, 30, 40, 50, 60, 70, 80, 90, or 100 contiguous amino acids that are identical to a contiguous sequence present in the extracellular region of human TIM-3. In some embodiments, the animal is a mouse, and the sequence encoding the region of endogenous TIM-3 is exon 1, exon 2, exon 3, exon 4, exon 5, exon 6, and/or exon 7 of the endogenous mouse TIM-3 gene. In some embodiments, the animal is heterozygous with respect to the replacement at the endogenous TIM-3 gene locus. In some embodiments, the animal is homozygous with respect to the replacement at the endogenous TIM-3 gene locus.

In one aspect, the disclosure relates to methods for making a genetically-modified, non-human animal. The methods involve replacing in at least one cell of the animal, at an endogenous TIM-3 gene locus, a sequence encoding a region of an endogenous TIM-3 with a sequence encoding a corresponding region of human TIM-3. In some embodiments, the sequence encoding the corresponding region of human TIM-3 comprises exon 1, exon 2, exon 3, exon 4, exon 5, exon 6 and/or exon 7 of a human TIM-3 gene. In some embodiments, the sequence encoding the corresponding region of TIM-3 comprises exon 2 or part of exon 2 of a human TIM-3 gene, and/or a part of exon 1 and/or exon 3 of a human TIM-3 gene. In some embodiments, the sequence encoding the corresponding region of human TIM-3 encodes amino acids 22-128 of SEQ ID NO: 26. In some embodiments, the region is located within the extracellular region of TIM-3. In some embodiments, the animal is a mouse, and the sequence encoding the region of the endogenous TIM-3 locus is exon 2 of mouse TIM-3 gene.

In one aspect, the disclosure relates to non-human animals comprising at least one cell comprising a nucleotide sequence encoding a chimeric TIM-3 polypeptide, wherein the chimeric TIM-3 polypeptide comprises at least 50 contiguous amino acid residues that are identical to the corresponding contiguous amino acid sequence of a human TIM-3, wherein the animal expresses the chimeric TIM-3. In some embodiments, the chimeric TIM-3 polypeptide has at least 50 contiguous amino acid residues that are identical to the corresponding contiguous amino acid sequence of a human TIM-3 extracellular region. In some embodiments, the chimeric TIM-3 polypeptide comprises a sequence that is at least 90%, 95%, or 99% identical to amino acids 22-128 of SEQ ID NO: 26. In some embodiments, the nucleotide sequence is operably linked to an endogenous TIM-3 regulatory element of the animal. In some embodiments, the chimeric TIM-3 polypeptide comprises an endogenous TIM-3 transmembrane region and/or an endogenous TIM-3 cytoplasmic region. In some embodiments, the nucleotide sequence is integrated to an endogenous TIM-3 gene locus of the animal. In some embodiments, the chimeric TIM-3 has at least one mouse TIM-3 activity (e.g., interacting with mouse GALECTIN-9 and/or mouse HMGB1, and inhibiting mouse T-cell immune responses) and/or at least one human TIM-3 activity (e.g., interacting with human GALECTIN-9 and/or human HMGB1, and inhibiting human T-cell immune responses).

In one aspect, the disclosure relates to methods of making a genetically-modified mouse cell that expresses a chimeric TIM-3, the method including: replacing, at an endogenous mouse TIM-3 gene locus, a nucleotide sequence encoding a region of mouse TIM-3 with a nucleotide sequence encoding a corresponding region of human TIM-3, thereby generating a genetically-modified mouse cell that includes a nucleotide sequence that encodes the chimeric TIM-3, wherein the mouse cell expresses the chimeric TIM-3. In some embodiments, the chimeric TIM-3 comprises an extracellular region of mouse TIM-3 comprising a mouse signal peptide sequence, an extracellular region of human TIM-3, a transmembrane and/or a cytoplasmic region of a mouse TIM-3. In some embodiments, the nucleotide sequence encoding the chimeric TIM-3 is operably linked to an endogenous TIM-3 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (TNFRSF4 or OX40). In some embodiments, the animal or mouse further comprises a sequence encoding an additional human or chimeric protein. In some embodiments, the additional human or chimeric protein is programmed cell death protein 1 (PD-1), CTLA-4, LAG-3, BTLA, PD-L1, 4-1BB, CD27, CD28, CD47, TIGIT, CD27, GITR, or OX40.

In one aspect, the disclosure relates to methods of determining effectiveness of an anti-TIM-3 antibody for the treatment of cancer, including: administering the anti-TIM-3 antibody to the animal as described herein, wherein the animal has a tumor, and determining the inhibitory effects of the anti-TIM-3 antibody to the tumor. In some embodiments, the tumor comprises one or more tumor cells that express GALECTIN-9 and/or HMGB1.

In some embodiments, the tumor comprises one or more cancer cells that are injected into the animal. In some embodiments, determining the inhibitory effects of the anti-TIM-3 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells.

In one aspect, the disclosure relates to methods of determining effectiveness of an anti-TIM-3 antibody for the treatment of various immune-related disorders, e.g., autoimmune diseases.

In one aspect, the disclosure relates to methods of determining effectiveness of an anti-TIM-3 antibody and an additional therapeutic agent for the treatment of a tumor, including administering the anti-TIM-3 antibody and the additional therapeutic agent to the animal as described herein, wherein the animal has a tumor, and determining the inhibitory effects on the tumor. In some embodiments, the animal further comprises a sequence encoding a human or chimeric programmed cell death protein 1 (PD-1) or cytotoxic T-lymphocyte-associated protein 4 (CTLA-4). In some embodiments, the additional therapeutic agent is an anti-PD-1 antibody. In some embodiments, the tumor comprises one or more tumor cells that express GALECTIN-9 and/or HMGB1. In some embodiments, the tumor comprises one or more tumor cells that express PD-L1 or PD-L2. In some embodiments, the tumor comprises one or more tumor cells that express CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells).

In one aspect, the disclosure relates to proteins comprising an amino acid sequence, wherein the amino acid sequence is one of the following: (a) an amino acid sequence set forth in SEQ ID NO: 30; (b) an amino acid sequence that is at least 90% identical to SEQ ID NO: 30; (c) an amino acid sequence that is at least 91%, 92%, 93%, 94%, 95%, 96%, 97%, 98%, or 99% identical to SEQ ID NO: 30; (d) an amino acid sequence that is different from the amino acid sequence set forth in SEQ ID NO: 30 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 30. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 28; (c) SEQ ID NO: 29; (d) a sequence that is at least 90% identical to SEQ ID NO: 28 or SEQ ID NO: 29; (e) a sequence that is at least 91%, 92%, 93%, 94%, 95%, 96%, 97%, 98%, or 99% identical to SEQ ID NO: 28; and (f) a sequence that is at least 91%, 92%, 93%, 94%, 95%, 96%, 97%, 98%, or 99% identical to SEQ ID NO: 29. In some embodiments, provided herein are cells comprising the nucleic acids disclosed herein. In some embodiments, provided herein are animals having the nucleic acids disclosed herein.

In one aspect, the disclosure relates to a targeting vector, including a) a DNA fragment homologous to the 5' end of a region to be altered (5' arm), which is selected from the TIM-3 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the TIM-3 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000077.6; c) the DNA fragment homologous to the 3' end of the region to be altered (3' arm/receptor) is selected from the nucleotide sequences that have at least 90% homology to the NCBI accession number NC_000077.6.

In some embodiments, a) the DNA fragment homologous to the 5' end of a region to be altered (5' arm/receptor) is selected from the nucleotides from the position 46454902 to the position 46456260 of the NCBI accession number NC_000077.6; c) the DNA fragment homologous to the 3' end of the region to be altered (3' arm/receptor) is selected from the nucleotides from the position 46456585 to the position 46457884 of the NCBI accession number NC_000077.6.

In some embodiments, a length of the selected genomic nucleotide sequence is about 1.2 kb, 1.5 kb or 1 kb. In some embodiments, the length is about 1359 bp or 1300 bp. In some embodiments, the region to be altered is exon 2 of TIM-3 gene. In some embodiments, the sequence of the 5' arm is shown in SEQ ID NO: 31. In some embodiments, the sequence of the 3' arm is shown in SEQ ID NO: 37.

In some embodiments, the targeting vector further includes a selectable gene marker.

In some embodiments, the target region is derived from human. In some embodiments, the target region is a part or entirety of the nucleotide sequence of a humanized TIM-3.

In some embodiments, the nucleotide sequence is shown as one or more of the first exon, the second exon, the third exon, the fourth exon, the fifth exon, the sixth exon, and the seventh exon of the DNA sequence of the human TIM-3.

In some embodiments, the nucleotide sequence of the human TIM-3 encodes the human TIM-3 protein with the NCBI accession number NP_116171.3 (SEQ ID NO: 26). The disclosure also relates to a cell including the targeting vector as described herein.

In another aspect, the disclosure relates to an sgRNA sequence for constructing a humanized animal model, wherein the sgRNA sequence targets the TIM-3 gene, the sgRNA is unique on the target sequence of the TIM-3 gene to be altered, and meets the sequence arrangement rule of 5'-NNN (20)-NGG3' or 5'-CCN—N (20)-3'. In some embodiments, the targeting site of the sgRNA in the mouse TIM-3 gene is located on the exon 2 of the mouse TIM-3 gene.

In another aspect, the disclosure relates to an sgRNA sequence for constructing a humanized animal model, wherein an upstream sequence thereof is shown as SEQ ID NO: 14, and a downstream sequence thereof is shown as SEQ ID NO: 16, and the sgRNA sequence recognizes a 5' targeting site.

The disclosure also relates to an sgRNA sequence for constructing a humanized animal model, wherein an upstream sequence thereof is shown as SEQ ID NO: 15, which is obtained by adding TAGG to the 5' end of SEQ ID NO: 14; a downstream sequence thereof is shown as SEQ ID NO: 17, which is obtained by adding AAAC to the 5' end of SEQ ID NO: 16, and the sgRNA sequence recognizes a 5' targeting site.

The disclosure also relates to an sgRNA sequence for constructing a humanized animal model, wherein an upstream sequence thereof is shown as SEQ ID NO: 18, and a downstream sequence thereof is shown as SEQ ID NO: 20, and the sgRNA sequence recognizes a 3' targeting site.

The disclosure further relates to an sgRNA sequence for constructing a humanized animal model, wherein an upstream sequence thereof is shown as SEQ ID NO: 19, which is obtained by adding TAGG to the 5' end of SEQ ID NO: 18; a downstream sequence thereof is shown as SEQ ID NO: 21, which is obtained by adding AAAC to the 5' end of SEQ ID NO: 20, and the sgRNA sequence recognizes a 3' targeting site.

In one aspect, the disclosure relates to a construct including the sgRNA sequence as described herein.

The disclosure also relates to a cell comprising the construct as described herein. In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to methods for establishing a TIM-3 gene humanized animal model. The methods include the steps of (a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of TIM-3 gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a TIM-3 gene humanized animal model to obtain a TIM-3 gene genetically modified humanized mouse;

(b) mating the TIM-3 gene genetically modified humanized mouse obtained in step (a) with another humanized mouse, and then screening to obtain a double humanized mouse model.

In some embodiments, in step (b), the TIM-3 gene genetically modified humanized mouse obtained in step (a) is mated with a PD-1 or CTLA-4 humanized mouse to obtain a TIM-3 and PD-1 double humanized mouse model or a TIM-3 and CTLA-4 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized TIM-3 gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a TIM-3 amino acid sequence of a humanized mouse, wherein the amino acid sequence is selected from the group consisting of:

a) an amino acid sequence shown in SEQ ID NO: 30;

b) an amino acid sequence having a homology of at least 90% with the amino acid sequence shown in SEQ ID NO: 30;

c) an amino acid sequence encoded by a nucleic acid sequence, wherein the nucleic acid sequence is able to hybridize to a nucleotide sequence encoding the amino acid shown in SEQ ID NO: 30 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 30;

e) an amino acid sequence that is different from the amino acid sequence shown in SEQ ID NO: 30 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 30.

The disclosure also relates to a TIM-3 DNA sequence of a humanized mouse, wherein the DNA sequence is selected from the group consisting of:

a) a DNA sequence that encodes the TIM-3 amino acid sequence of a humanized mouse;

b) a DNA sequence that is set forth in SEQ ID NO: 34;

c) a DNA sequence having a coding DNA sequence (CDS) as shown in SEQ ID NO: 28;

d) a DNA sequence that is able to hybridize to the nucleotide sequence as shown in SEQ ID NO: 34 or SEQ ID NO: 28 under a low stringency condition;

e) a DNA sequence that has a homology of at least 90% with the nucleotide sequence as shown in SEQ ID NO: 28 or SEQ ID NO: 29;

f) a DNA sequence that encodes an amino acid sequence, wherein the amino acid sequence has a homology of at least 90% with the amino acid sequence shown in SEQ ID NO: 30;

g) a DNA sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 30;

h) a DNA sequence that encodes an amino acid sequence, wherein the amino acid sequence is different from the amino acid sequence shown in SEQ ID NO: 30 by no more than 10, 9, 8, 7, 6, 5, 4, 3, 2 or no more than 1 amino acid; and/or i) a DNA sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 30.

j) and optimized SEQ ID NO: 34.

The disclosure further relates to a TIM-3 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the TIM-3 gene function, human TIM-3 antibodies, the drugs or efficacies for human TIM-3 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

In FIGS. 14A and 14B, + is hCTLA-4 homozygous positive control, − is wildtype negative control, WT is wildtype. In FIGS. 14C and 14D, + is hTIM-3 heterozygous positive control, − is wildtype negative control, WT is wildtype. The mouse numbered 301 was homozygous for both humanized CTLA-4 and humanized TIM-3. The mice numbered 300, 302, and 308 were TIM-3$^{H/+}$/CTLA-4$^{H/G}$. The mouse numbered 306 was TIM-3$^{H/H}$/CTLA-4$^{H/+}$. The mice numbered 294, 295, and 304 were TIM-3$^{H/+}$/CTLA-4$^{H/+}$.

In FIGS. 15A and 15B, + is TIM-3 heterozygous control, − is wildtype negative control, WT is wildtype. In FIGS. 15C and 15D, −/− is humanized PD-1 homozygous, +/− is humanized PD-1 heterozygous, and WT is wildtype. The mice numbered from 6901 to 6916 are hTIM-3 homozygous (FIGS. 15A and 15B). The mice numbered from 6901 to 6916 are hPD-1 homozygous. All sixteen mice were thus all homozygous for both hTIM-3 and hPD-1.

FIG. 24 shows the alignment between mouse TIM-3 amino acid sequence (NP_599011.2; SEQ ID NO: 24) and human TIM-3 amino acid sequence (NP_116171.3; SEQ ID NO: 26) by NCBI Basic Local Alignment Search Tool (BLAST).

SEQUENCE LISTING

Figure 1A:
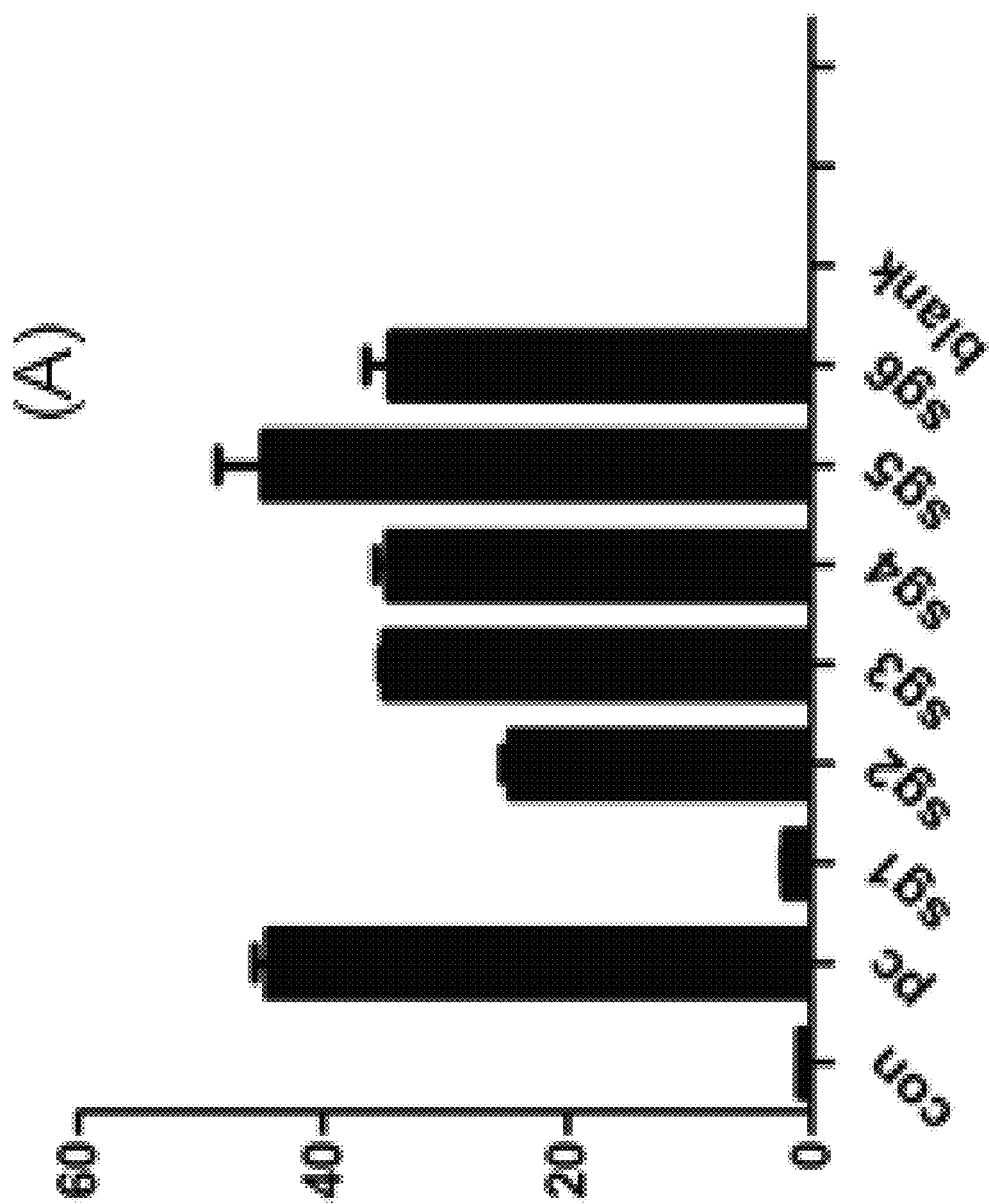
FIG. 1A is a graph showing activity testing results for sgRNA1-sgRNA6 (Con is a negative control; PC is a positive control; and blank is a blank control).

The instant application contains a Sequence Listing which has been submitted electronically in ASCII format and is hereby incorporated by reference in its entirety. Said ASCII copy, created on Jul. 31, 2019, is named SEQUENCE LISTING-Updated.txt and is 34,863 bytes in size.

DETAILED DESCRIPTION

This disclosure relates to transgenic non-human animal with human or chimeric (e.g., humanized) T-cell immunoglobulin and mucin-domain containing-3 (TIM-3), and methods of use thereof.

TIM-3, also known as Hepatitis A Virus Cellular Receptor 2 (HAVCR2), is a co-inhibitory receptor of T cells. Tim-3 is found on T cells in patients with cancer, and is a marker of dysfunctional T cells in multiple cancer types both in experimental models and in humans. In patients with advanced melanoma, approximately 30% of NY-ESO-1-specific CD8+ T cells express Tim-3. In patients with non-small cell lung cancer (NSCLC), approximately one third of CD8+ tumor-infiltrating lymphocytes (TIL) express Tim-3. In patients with follicular B-cell non-Hodgkin lymphoma, approximately one third of lymph node CD4+ and CD8+ T cells express Tim-3. In these three cancers, all Tim-3+ T cells co-express PD-1 and exhibit defects in proliferation and effector cytokine production. In addition to regulating CD8+ T-cell effector function in cancer, TIM-3 is involved in the function of intratumoral FoxP3+ regulatory T cells (Treg). The presence of Tim-3+ Tregs has been suggested to be a common feature across multiple different cancers as Tim-3+ Tregs have been reported in hepatocellular, ovarian, colon, and cervical carcinomas. (Cancer Immunol Res. 2014 May; 2(5):393-8; Curr Top Microbiol Immunol. 2017 Sep. 13.)

As TIM-3 is involved in T cell inhibitory pathway, it thus can be expected that the TIM-3 antibody has great application values, e.g., as a tumor immunotherapy or a treatment for autoimmune disease (e.g., systemic lupus erythematosus, multiple sclerosis, or CNS autoimmune disease). In order to make the animal experiments more effective and more relevant, the present disclosure provides humanized TIM-3 genetically modified animal models and methods of establishing such animal models.

Experimental animal models are an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered, 1985); Oligonucleotide Synthesis (M. J. Gaited., 1984); Mullis et al U.S. Pat. No. 4,683,195; Nucleic Acid Hybridization (B. D. Hames& S. J. Higginseds. 1984); Transcription And Translation (B. D. Hames& S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986), each of which is incorporated herein in its entirety by reference.

TIM-3 (T-Cell Immunoglobulin and Mucin-Domain Containing-3)

TIM-3 is a type I transmembrane protein. Tim-3 acts as a negative regulator of Th1 and CTL responses. TIM-3 harbors five conserved tyrosine residues, two of which are phosphorylated and important for binding to the intracellular adapter protein Bat3 (HLA-B associated transcript 3). Phosphorylation of the two tyrosines in the Tim-3 tail promotes downstream inhibitory signals. In the absence of binding of Tim-3 ligands, Bat3 is bound to the unphosphorylated cytoplasmic tail of Tim-3, recruits Lck, and preserves or may even promote T cell signaling.

Tim-3 has been shown to interact with phosphatidylserine displayed on the surface of apoptotic cells, the alarmin protein HMGB1 (High-Mobility Group Box 1) and Galectin-9, a widely expressed soluble protein with specificity for carbohydrate chains containing β-galactoside sugars. The interaction of Tim-3 with its ligands (galectin-9) induces an intracellular calcium flux and phosphorylation of the two critical tyrosine residues (Y256 and Y263), which releases Bat3 from the cytoplasmic tail of Tim-3. The release of Bat3 allows for the binding of SH2 domain-containing Src kinases and promotion of subsequent negative regulation of TCR signaling. (Curr Top Microbiol Immunol. 2017 Sep. 13.) In addition, interaction between Tim-3 and HMGB1 has also been reported to suppress the activation of dendritic cells associated with tumors.

Figure 3A:
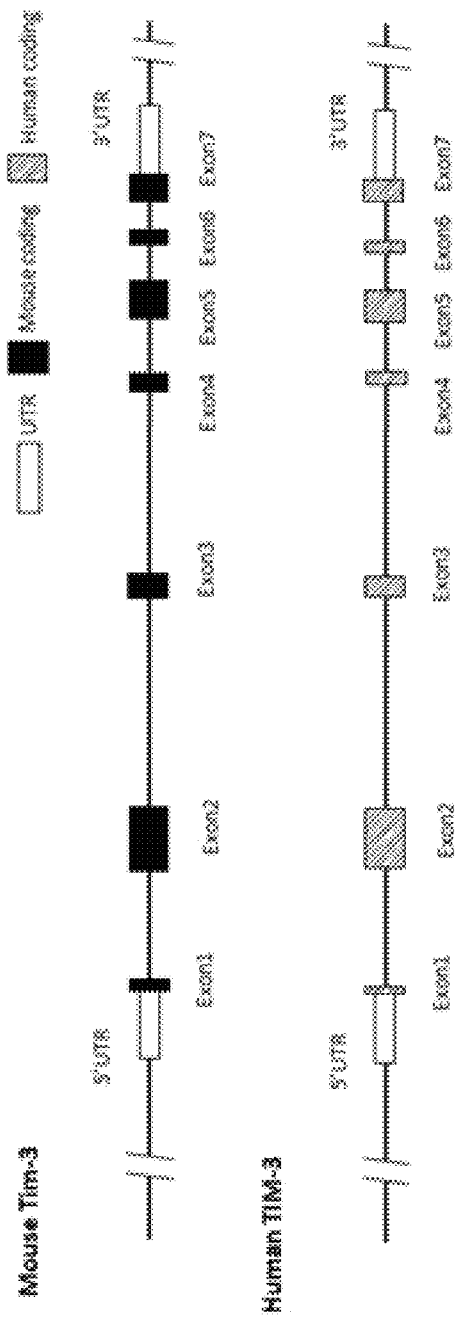
FIG. 3A is a schematic diagram showing comparison of human and mouse TIM-3 genes.

In human genomes, TIM-3 gene locus has seven exons, exon 1, exon 2, exon 3, exon 4, exon 5, exon 6, and exon 7 (FIG. 3A). The TIM-3 protein also has an extracellular region, a transmembrane region, and a cytoplasmic region, and the signal peptide is located at the extracellular region of TIM-3. The nucleotide sequence for human TIM-3 mRNA is NM 032782.4 (SEQ ID NO: 25), and the amino acid sequence for human TIM-3 is NP_116171.3 (SEQ ID NO: 26). The location for each exon and each region in human TIM-3 nucleotide sequence and amino acid sequence is listed below:

TABLE 1

| Human TIM-3 (approximate location) | NM_032782.4 2448 bp (SEQ ID NO: 25) | NP_116171.3 301 aa (SEQ ID NO: 26) |
| --- | --- | --- |
| Exon 1 | 1-312 | 1-19 |
| Exon 2 | 313-648 | 20-131 |
| Exon 3 | 649-732 | 132-159 |
| Exon 4 | 733-776 | 160-174 |
| Exon 5 | 777-930 | 175-225 |
| Exon 6 | 931-967 | 226-238 |
| Exon 7 | 968-2430 | 239-301 |
| Signal peptide | 255-317 | 1-21 |
| Extracellular region (excluding signal peptide region) | 318-860 | 22-202 |
| Transmembrane region | 861-923 | 203-223 |
| Cytoplasmic region | 924-1157 | 224-301 |
| Donor region in Example | 318-638 | 22-128 |

Similarly, in mice, TIM-3 gene locus has seven exons, exon 1, exon 2, exon 3, exon 4, exon 5, exon 6, and exon 7 (FIG. 3A). The TIM-3 protein also has an extracellular region, a transmembrane region, and a cytoplasmic region, and the signal peptide is located at the extracellular region of TIM-3. The nucleotide sequence for mouse TIM-3 cDNA is NM 134250.2 (SEQ ID NO: 23), the amino acid sequence for mouse TIM-3 is NP_599011.2 (SEQ ID NO: 24). The location for each exon and each region in the mouse TIM-3 nucleotide sequence and amino acid sequence is listed below:

TABLE 2

| Mouse TIM-3 (approximate location) | NM_134250.2 2725 bp (SEQ ID NO: 23) | NP_599011.2 281 aa (SEQ ID NO: 24) |
| --- | --- | --- |
| Exon 1 | 1-128 | 1-19 |
| Exon 2 | 129-467 | 20-132 |
| Exon 3 | 468-551 | 133-160 |
| Exon 4 | 552-592 | 161-174 |
| Exon 5 | 593-719 | 175-216 |
| Exon 6 | 720-756 | 217-229 |
| Exon 7 | 757-2725 | 230-281 |
| Signal peptide | 71-127 | 1-19 |
| Extracellular region (excluding signal peptide region) | 128-649 | 20-193 |
| Transmembrane region | 650-712 | 194-214 |
| Cytoplasmic region | 713-913 | 215-281 |
| Replaced region in Example | 134-457 | 22-129 |

The mouse TIM-3 gene (Gene ID: 171285) is located in Chromosome 11 of the mouse genome, which is located from 46454931-46481255 of NC_000077.6 (GRCm38.p4 (GCF_000001635.24)). The 5'-UTR is from 46454935 to 46454995, exon 1 is from 46454996 to 46455058, the first intron is from 46455059 to 46456255, exon 2 is from 46456256 to 46456594, the second intron is from 46456595 to 46459049, exon 3 is from 46459050 to 46459133, the third intron is from 46459134 to 46466871, exon 4 is from 46466872 to 46466912, the fourth intron is from 46466913 to 46469469, exon 5 is from 46469470 to 46469596, the fifth intron is from 46469597 to 46475883, exon 6 is from 46475884 to 46475920, the sixth intron is from 46475921 to 46479286, exon 7 is from 46479287 to 46479446, the 3'-UTR is from 46479447 to 46481255 of NC_000077.6, based on transcript NM 134250.2. All relevant information for mouse TIM-3 locus can be found in the NCBI website with Gene ID: 171285, which is incorporated by reference herein in its entirety.

FIG. 24 shows the alignment between mouse TIM-3 amino acid sequence (NP_599011.2; SEQ ID NO: 24) and human TIM-3 amino acid sequence (NP_116171.3; SEQ ID NO: 26). Thus, the corresponding amino acid residue or region between human and mouse TIM-3 can also be found in FIG. 24.

TIM-3 genes, proteins, and locus of the other species are also known in the art. For example, the gene ID for TIM-3 in *Rattus norvegicus* is 363578, the gene ID for TIM-3 in *Macaca mulatta* (Rhesus monkey) is 714891, the gene ID for TIM-3 in *Danio rerio* is 100536120. The relevant information for these genes (e.g., intron sequences, exon sequences, amino acid residues of these proteins) can be found, e.g., in NCBI database.

The present disclosure provides human or chimeric (e.g., humanized) TIM-3 nucleotide sequence and/or amino acid sequences. In some embodiments, the entire sequence of mouse exon 1, exon 2, exon 3, exon 4, exon 5, exon 6, exon 7, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, signal peptide, extracellular region, transmembrane region, or cytoplasmic region. In some embodiments, a region, a portion, or the entire sequence of mouse exon 1, exon 2, exon 3, exon 4, exon 5, exon 6 and/or exon 7 (e.g., exon 2) are replaced by the human exon 1, exon 2, exon 3, exon 4, exon 5, exon 6, and/or exon 7 (e.g., exon 2) sequence.

In some embodiments, the present disclosure also provides a chimeric (e.g., humanized) TIM-3 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse TIM-3 mRNA sequence (e.g., SEQ ID NO: 23), mouse TIM-3 amino acid sequence (e.g., SEQ ID NO: 24), or a portion thereof (e.g., exon 2); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human TIM-3 mRNA sequence (e.g., SEQ ID NO: 25), human TIM-3 amino acid sequence (e.g., SEQ ID NO: 26), or a portion thereof (e.g., exon 2).

In some embodiments, the sequence encoding amino acids 22-129 of mouse TIM-3 (SEQ ID NO: 24) is replaced. In some embodiments, the sequence is replaced by a sequence encoding a corresponding region of human TIM-3 (e.g., amino acids 22-128 of human TIM-3 (SEQ ID NO: 26).

In some embodiments, the nucleic acids as described herein are operably linked to a promotor or regulatory element, e.g., an endogenous mouse TIM-3 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse TIM-3 nucleotide sequence (e.g., exon 1, exon 2, exon 3, exon 4, exon 5, exon 6, exon 7, or NM_134250.2 (SEQ ID NO: 23)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse TIM-3 nucleotide sequence (e.g., exon 1, exon 2, exon 3, exon 4, exon 5, exon 6, exon 7, or NM_134250.2 (SEQ ID NO: 23)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human TIM-3 nucleotide sequence (e.g., exon 1, exon 2, exon 3, exon 4, exon 5, exon 6, exon 7, or NM_032782.4 (SEQ ID NO: 25)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human TIM-3 nucleotide sequence (e.g., exon 1, exon 2, exon 3, exon 4, exon 5, exon 6, exon 7, or NM_032782.4 (SEQ ID NO: 25)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse TIM-3 amino acid sequence (e.g., exon 1, exon 2, exon 3, exon 4, exon 5, exon 6, exon 7, or NP_599011.2 (SEQ ID NO: 24)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse TIM-3 amino acid sequence (e.g., exon 1, exon 2, exon 3, exon 4, exon 5, exon 6, exon 7, or NP_599011.2 (SEQ ID NO: 24)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human TIM-3 amino acid sequence (e.g., exon 1, exon 2, exon 3, exon 4, exon 5, exon 6, exon 7, or NP_116171.3 (SEQ ID NO: 26)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human TIM-3 amino acid sequence (e.g., exon 1, exon 2, exon 3, exon 4, exon 5, exon 6, exon 7, or NP_116171.3 (SEQ ID NO: 26)).

The present disclosure also provides a humanized TIM-3 mouse amino acid sequence, wherein the amino acid sequence is selected from the group consisting of:

a) an amino acid sequence shown in SEQ ID NO: 30;

b) an amino acid sequence having a homology of at least 90% with or at least 90% identical to the amino acid sequence shown in SEQ ID NO: 30;

c) an amino acid sequence encoded by a nucleic acid sequence, wherein the nucleic acid sequence is able to hybridize to a nucleotide sequence encoding the amino acid shown in SEQ ID NO: 30 under a low stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 30; e) an amino acid sequence that is different from the amino acid sequence shown in SEQ ID NO: 30 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 30.

The present disclosure also relates to a TIM-3 DNA sequence, wherein the DNA sequence can be selected from the group consisting of:

a) a DNA sequence as shown in SEQ ID NO: 28, or a DNA sequence encoding a homologous TIM-3 amino acid sequence of a humanized mouse;

b) a DNA sequence that is shown in SEQ ID NO: 29;

c) a DNA sequence that is able to hybridize to the nucleotide sequence as shown in SEQ ID NO: 28 or SEQ ID NO: 29 under a low stringency condition;

d) a DNA sequence that has a homology of at least 90% or at least 90% identical to the nucleotide sequence as shown in SEQ ID NO: 28 or SEQ ID NO: 29;

e) a DNA sequence that encodes an amino acid sequence, wherein the amino acid sequence has a homology of at least 90% with or at least 90% identical to the amino acid sequence shown in SEQ ID NO: 30;

f) a DNA sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 30;

g) a DNA sequence that encodes an amino acid sequence, wherein the amino acid sequence is different from the amino acid sequence shown in SEQ ID NO: 30 by no more than 10, 9, 8, 7, 6, 5, 4, 3, 2 or no more than 1 amino acid; and/or h) a DNA sequence that encodes an amino acid sequence, wherein the amino acid sequence comprises a substitution, a deletion and/or insertion of one or more amino acids to the amino acid sequence shown in SEQ ID NO: 30.

The present disclosure further relates to a TIM-3 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 28 or SEQ ID NO: 29.

The disclosure also provides an amino acid sequence that has a homology of at least 90% with, or at least 90% identical to the sequence shown in SEQ ID NO: 30, and has protein activity. In some embodiments, the homology with the sequence shown in SEQ ID NO: 30 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 30 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleotide sequence that has a homology of at least 90%, or at least 90% identical to the sequence shown in SEQ ID NO: 29, and encodes a polypeptide that has protein activity. In some embodiments, the homology with the sequence shown in SEQ ID NO: 29 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 29 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or chimeric (e.g., humanized) TIM-3 from an endogenous non-human TIM-3 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous TIM-3 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized TIM-3 gene or a humanized TIM-3 nucleic acid. In some embodiments, at least one or more portions of the gene or the nucleic acid is from the human TIM-3 gene, at least one or more portions of the gene or the nucleic acid is from a non-human TIM-3 gene. In some embodiments, the gene or the nucleic acid comprises a sequence that encodes a TIM-3 protein. The encoded TIM-3 protein is functional or has at least one activity of the human TIM-3 protein or the non-human TIM-3 protein, e.g., binding to human or non-human GALECTIN-9 or HMGB1, regulating immune response, TCR signaling, and/or Th1 and CTL responses.

In some embodiments, the chimeric protein or the chimeric polypeptide is a humanized TIM-3 protein or a humanized TIM-3 polypeptide. In some embodiments, at least one or more portions of the amino acid sequence of the protein or the polypeptide is from a human TIM-3 protein, and at least one or more portions of the amino acid sequence of the protein or the polypeptide is from a non-human TIM-3 protein. The humanized TIM-3 protein or the humanized TIM-3 polypeptide is functional or has at least one activity of the human TIM-3 protein or the non-human TIM-3 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/

SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 129S4/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized TIM-3 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human TIM-3 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature TIM-3 coding sequence with human mature TIM-3 coding sequence.

Genetically modified non-human animals that comprise a modification of an endogenous non-human TIM-3 locus. In some embodiments, the modification can comprise a human nucleic acid sequence encoding at least a portion of a mature TIM-3 protein (e.g., at least 10%, 20%, 30%, 40%, 50%, 60%, 70%, 80%, 90%, 95%, 96%, 97%, 98%, or 99% identical to the mature TIM-3 protein sequence). Although genetically modified cells are also provided that can comprise the modifications described herein (e.g., ES cells, somatic cells), in many embodiments, the genetically modified non-human animals comprise the modification of the endogenous TIM-3 locus in the germline of the animal.

Genetically modified animals can express a human TIM-3 and/or a chimeric (e.g., humanized) TIM-3 from endogenous mouse loci, wherein the endogenous mouse TIM-3 gene has been replaced with a human TIM-3 gene and/or a nucleotide sequence that encodes a region of human TIM-3 sequence or an amino acid sequence that is at least 10%, 20%, 30%, 40%, 50%, 60%, 70&, 80%, 90%, 95%, 96%, 97%, 98%, or 99% identical to the human TIM-3 sequence. In various embodiments, an endogenous non-human TIM-3 locus is modified in whole or in part to comprise human nucleic acid sequence encoding at least one protein-coding sequence of a mature TIM-3 protein.

In some embodiments, the genetically modified mice express the human TIM-3 and/or chimeric TIM-3 (e.g., humanized TIM-3) from endogenous loci that are under control of mouse promoters and/or mouse regulatory elements. The replacement(s) at the endogenous mouse loci provide non-human animals that express human TIM-3 or chimeric TIM-3 (e.g., humanized TIM-3) in appropriate cell types and in a manner that does not result in the potential pathologies observed in some other transgenic mice known in the art. The human TIM-3 or the chimeric TIM-3 (e.g., humanized TIM-3) expressed in animal can maintain one or more functions of the wildtype mouse or human TIM-3 in the animal. For example, human or non-human Tim-3 ligands (e.g., GALECTIN-9 or HMGB1) can bind to the expressed TIM-3 and downregulate immune response, e.g., downregulate immune response by at least 10%, 20%, 30%, 40%, or 50%. Furthermore, in some embodiments, the animal does not express endogenous TIM-3. As used herein, the term "endogenous TIM-3" refers to TIM-3 protein that is expressed from an endogenous TIM-3 nucleotide sequence of the genetically modified non-human animal (e.g., mouse) before the genetic modification.

The genome of the animal can comprise a sequence encoding an amino acid sequence that is at least 70%, 75%, 80%, 85%, 90%, 95%, 99%, or 100% identical to human TIM-3 (NP_116171.3) (SEQ ID NO: 26). In some embodiments, the genome comprises a sequence encoding an amino acid sequence that is at least 70%, 75%, 80%, 85%, 90%, 95%, 99%, or 100% identical to SEQ ID NO: 30.

The genome of the genetically modified animal can comprise a replacement at an endogenous TIM-3 gene locus of a sequence encoding a region of endogenous TIM-3 with a sequence encoding a corresponding region of human TIM-3. In some embodiments, the sequence that is replaced is any sequence within the endogenous TIM-3 gene locus, e.g., exon 1, exon 2, exon 3, exon 4, exon 5, exon 6, exon 7, 5'-UTR, 3'UTR, the first intron, the second intron, and the third intron, the fourth intron, the fifth intron, the sixth intron etc. In some embodiments, the sequence that is replaced is within the regulatory region of the endogenous TIM-3 gene. In some embodiments, the sequence that is replaced is exon 2 of an endogenous mouse TIM-3 gene locus.

The genetically modified animal can have one or more cells expressing a human or chimeric TIM-3 (e.g., humanized TIM-3) having an extracellular region and a cytoplasmic region, wherein the extracellular region comprises a sequence that is at least 50%, 60%, 70%, 80%, 90%, 95%, 99% identical to the extracellular region of human TIM-3. In some embodiments, the extracellular region of the humanized TIM-3 has a sequence that has at least 10, 20, 30, 40, 50, 60, 70, 80, 90, or 100 amino acids (e.g., contiguously or non-contiguously) that are identical to human TIM-3.

Because human TIM-3 and non-human TIM-3 (e.g., mouse TIM-3) sequences, in many cases, are different, antibodies that bind to human TIM-3 will not necessarily have the same binding affinity with mouse TIM-3 or have the same effects to mouse TIM-3. Therefore, the genetically modified animal having a human or a humanized extracellular region can be used to better evaluate the effects of anti-human TIM-3 antibodies in an animal model. In some embodiments, the genome of the genetically modified animal comprises a sequence encoding an amino acid sequence that corresponds to part or the entire sequence of exon 1, exon 2, exon 3, exon 4, exon 5, exon 6 and/or exon 7 of human TIM-3, part or the entire sequence of extracellular region of human TIM-3 (with or without signal peptide), or part or the entire sequence of amino acids 22-128 of SEQ ID NO: 26.

In some embodiments, the non-human animal can have, at an endogenous TIM-3 gene locus, a nucleotide sequence encoding a chimeric human/non-human TIM-3 polypeptide, wherein a human portion of the chimeric human/non-human TIM-3 polypeptide comprises a portion of human TIM-3 extracellular domain, and wherein the animal expresses a functional TIM-3 on a surface of a cell of the animal. The human portion of the chimeric human/non-human TIM-3 polypeptide can comprise a portion of exon 1, exon 2, exon 3, exon 4, exon 5, exon 6, and/or exon 7 of human TIM-3. In some embodiments, the human portion of the chimeric human/non-human TIM-3 polypeptide can comprise a sequence that is at least 80%, 85%, 90%, 95%, or 99% identical to amino acids 22-128 of SEQ ID NO: 26.

In some embodiments, the non-human portion of the chimeric human/non-human TIM-3 polypeptide comprises transmembrane and/or cytoplasmic regions of an endogenous non-human TIM-3 polypeptide. There may be several advantages that are associated with the transmembrane and/or cytoplasmic regions of an endogenous non-human TIM-3 polypeptide. For example, once a TIM-3 ligand (e.g., GALECTIN-9 or HMGB1) binds to TIM-3, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of TIM-3 are also derived from endogenous sequence.

Furthermore, the genetically modified animal can be heterozygous with respect to the replacement at the endogenous TIM-3 locus, or homozygous with respect to the replacement at the endogenous TIM-3 locus.

In some embodiments, the humanized TIM-3 locus lacks a human TIM-3 5'-UTR. In some embodiment, the humanized TIM-3 locus comprises a rodent (e.g., mouse) 5'-UTR. In some embodiments, the humanization comprises a human 3'-UTR. In appropriate cases, it may be reasonable to presume that the mouse and human TIM-3 genes appear to be similarly regulated based on the similarity of their 5'-flanking sequence. As shown in the present disclosure, humanized TIM-3 mice that comprise a replacement at an endogenous mouse TIM-3 locus, which retain mouse regulatory elements but comprise a humanization of TIM-3 encoding sequence, do not exhibit pathologies. Both genetically modified mice that are heterozygous or homozygous for humanized TIM-3 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized TIM-3 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized TIM-3 in the genome of the animal.

Figure 2:
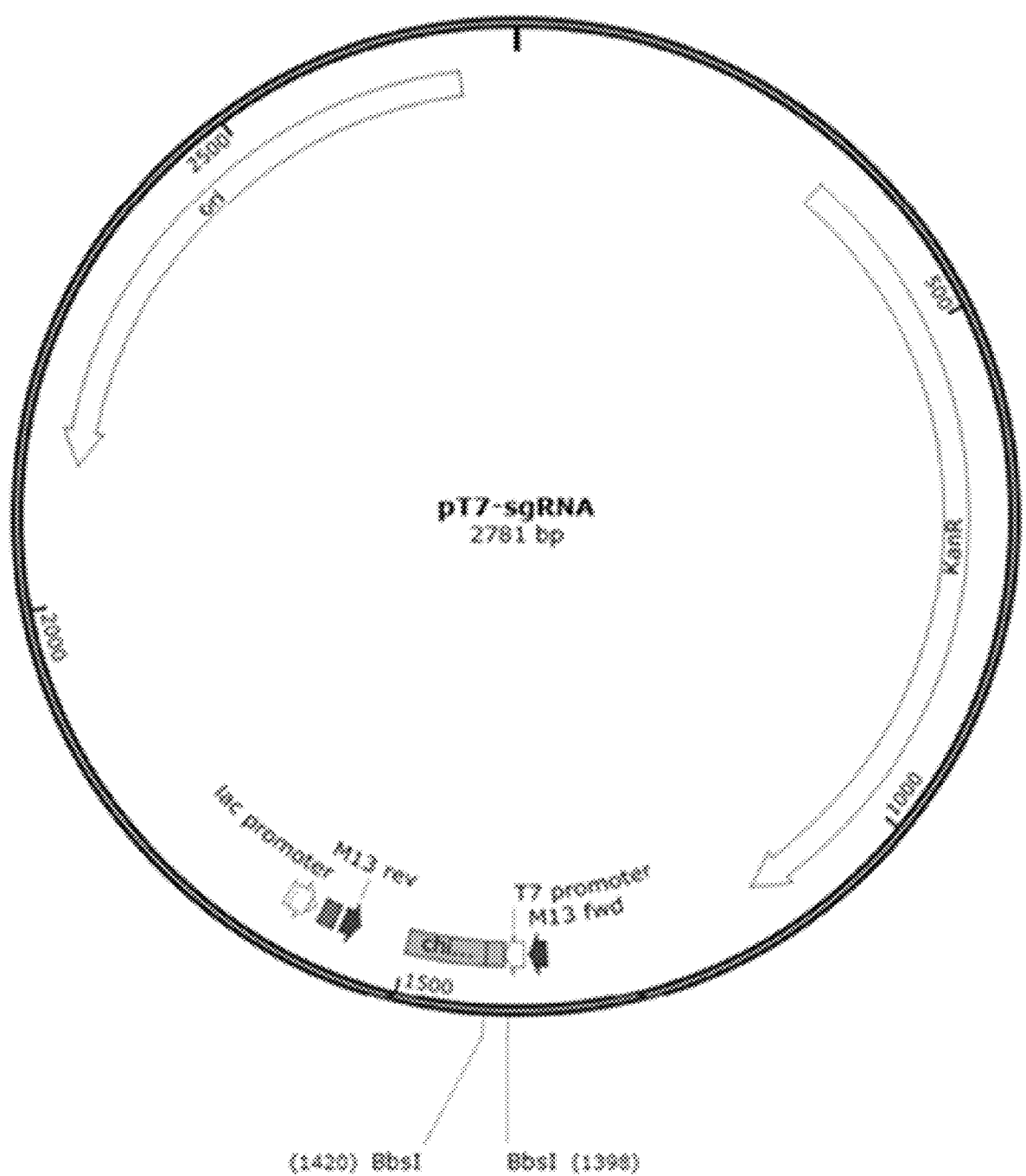
FIG. 2 is a schematic diagram showing pT7-sgRNA plasmid map.

In some embodiments, the non-human mammal comprises the genetic construct as described herein (e.g., gene construct as shown in FIG. 2). In some embodiments, a non-human mammal expressing human or humanized TIM-3 is provided. In some embodiments, the tissue-specific expression of human or humanized TIM-3 protein is provided.

In some embodiments, the expression of human or humanized TIM-3 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human TIM-3 protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human TIM-3 protein.

Vectors

The present disclosure relates to a targeting vector, comprising: a) a DNA fragment homologous to the 5' end of a region to be altered (5' arm), which is selected from the TIM-3 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the TIM-3 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000077.6; c) the DNA fragment homologous to the 3' end of the region to be altered (3' arm) is selected from the nucleotide sequences that have at least 90% homology to the NCBI accession number NC_000077.6.

In some embodiments, a) the DNA fragment homologous to the 5' end of a region to be altered (5' arm) is selected from the nucleotides from the position 46454902 to the position 46456260 of the NCBI accession number NC_000077.6; c) the DNA fragment homologous to the 3' end of the region to be altered (3' arm) is selected from the nucleotides from the position 46456585 to the position 46457884 of the NCBI accession number NC_000077.6.

In some embodiments, the length of the selected genomic nucleotide sequence in the targeting vector can be about 1.2 kb, about 1.5 kb, or about 1 kb. In some embodiments, the length is about 1359 bp or about 1300 bp.

In some embodiments, the region to be altered is exon 1, exon 2, exon 3, exon 4, exon 5, exon 6 and/or exon 7 of TIM-3 gene (e.g., exon 2 of TIM-3 gene).

The targeting vector can further include a selected gene marker.

In some embodiments, the sequence of the 5' arm is shown in SEQ ID NO: 31; and the sequence of the 3' arm is shown in SEQ ID NO: 37.

In some embodiments, the target region is derived from human (e.g., 157106637-157106957 of NC_000005.10). For example, the target region in the targeting vector is a part or entirety of the nucleotide sequence of a human TIM-3, preferably the nucleotide sequence is shown as a first exon, a second exon, a third exon, a fourth exon, a fifth exon, a sixth exon and/or a seventh exon of the DNA sequence of the human TIM-3. In some embodiments, the nucleotide sequence of the humanized TIM-3 encodes the humanized TIM-3 protein with the NCBI accession number NP_116171.3 (SEQ ID NO: 26).

The disclosure also relates to a cell comprising the targeting vectors as described above.

Moreover, the disclosure also relates to an sgRNA sequence for constructing a humanized animal model, wherein the sgRNA sequence targets the TIM-3 gene, the sgRNA is unique on the target sequence of the TIM-3 gene to be altered, and meets the sequence arrangement rule of 5'-NNN (20)-NGG3' or 5'-CCN—N (20)-3'; and in some embodiments, the targeting site of the sgRNA in the mouse TIM-3 gene is located on the exon 1, exon 2, exon 3, exon 4, exon 5, exon 6, or exon 7 of the mouse TIM-3 gene (e.g., exon 2 of the mouse TIM-3 gene).

In some embodiments, an upstream sequence thereof is shown as SEQ ID NO: 14, and a downstream sequence thereof is shown as SEQ ID NO: 16, and the sgRNA sequence recognizes a 5' targeting site. In some embodiments, the forward oligonucleotide sequence is obtained by adding TAGG to the 5' end of SEQ ID NO: 14; and the reverse oligonucleotide sequence is obtained by adding AAAC to the 5' end of SEQ ID NO: 16.

In some embodiments, the disclosure provides an sgRNA sequence for constructing a humanized animal model, wherein an upstream sequence thereof is shown as SEQ ID NO: 18, and a downstream sequence thereof is shown as SEQ ID NO: 20, and the sgRNA sequence recognizes a 3' targeting site. In some embodiments, the forward oligonucleotide sequence is obtained by adding TAGG to the 5' end of SEQ ID NO: 18; and the reverse oligonucleotide sequence is obtained by adding AAAC to the 5' end of SEQ ID NO: 20.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous TIM-3 gene locus, a sequence encoding a region of an endogenous TIM-3 with a sequence encoding a corresponding region of human or chimeric TIM-3. In some embodiments, the replacement occurs in a germ cell, a somatic cell, a blastocyst, or a fibroblast, etc. The nucleus of a somatic cell or the fibroblast can be inserted into an enucleated oocyte.

Figure 3B:
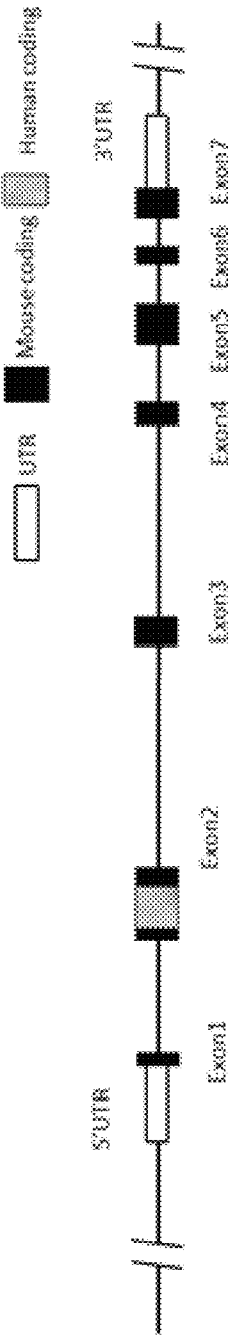
FIG. 3B is a schematic diagram showing humanized TIM-3 mouse gene map.
Figure 3C:
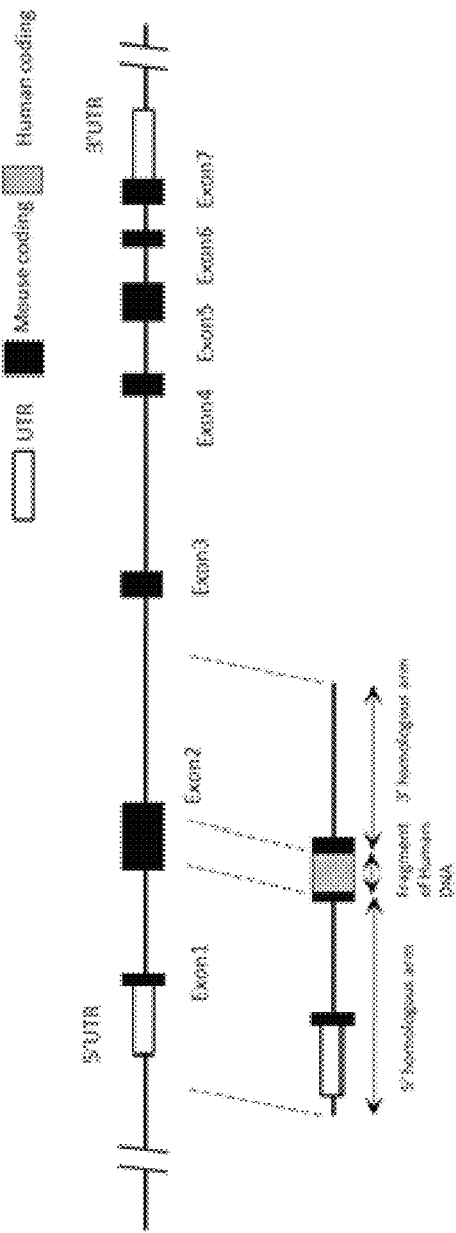
FIG. 3C is a schematic diagram showing mouse TIM-3 gene targeting strategy.

FIG. 3C shows a humanization strategy for a mouse TIM-3 locus. In FIG. 3C, the targeting strategy involves a vector comprising the 5' end homologous arm, human TIM-3 gene fragment, 3' homologous arm. The process can involve replacing endogenous TIM-3 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous TIM-3 sequence with human TIM-3 sequence.

Thus, in some embodiments, the methods for making a genetically modified, humanized animal, can include the step of replacing at an endogenous TIM-3 locus (or site), a nucleic acid encoding a sequence encoding a region of endogenous TIM-3 with a sequence encoding a corresponding region of human TIM-3. The sequence can include a region (e.g., a part or the entire region) of exon 1, exon 2, exon 3, exon 4, exon 5, exon 6, and/or exon 7, of a human TIM-3 gene. In some embodiments, the sequence includes a region of exon 2 of a human TIM-3 gene (e.g., amino acids 22-128 of SEQ ID NO: 26). In some embodiments, the region is located within the extracellular region of TIM-3. In some embodiments, the endogenous TIM-3 locus is exon 2 of mouse TIM-3.

In some embodiments, the methods of modifying a TIM-3 locus of a mouse to express a chimeric human/mouse TIM-3 peptide can include the steps of replacing at the endogenous mouse TIM-3 locus a nucleotide sequence encoding a mouse TIM-3 with a nucleotide sequence encoding a human TIM-3, thereby generating a sequence encoding a chimeric human/mouse TIM-3.

In some embodiments, the nucleotide sequence encoding the chimeric human/mouse TIM-3 can include a first nucleotide sequence encoding an extracellular region of mouse TIM-3 (with or without the mouse signal peptide sequence); a second nucleotide sequence encoding an extracellular region of human TIM-3; a third nucleotide sequence encoding a transmembrane and a cytoplasmic region of a mouse TIM-3.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a TIM-3 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized TIM-3 protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized TIM-3, which are useful for testing agents that can decrease or block the interaction between TIM-3 and GALECTIN-9 or the interaction between TIM-3 and other ligands (e.g., HMGB1), testing whether an agent can increase or decrease the immune response, and/or determining whether an agent is an TIM-3 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-TIM-3 antibody for the treatment of cancer. The methods involving administering the anti-TIM-3 antibody to the animal as described herein, wherein the animal has a tumor; and determining the inhibitory effects of the anti-TIM-3 antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more tumor cells that express GALECTIN-9 or HMGB1 (Cancer Immunol Res. 2014 May; 2(5):393-8; Curr Top Microbiol Immunol. 2017 Sep. 13). In some embodiments, the tumor comprises one or more cancer cells (e.g., human or mouse cancer cells) that are injected into the animal. In some embodiments, the anti-TIM-3 antibody or anti-GALECTIN-9 antibody prevents GALECTIN-9 from binding to TIM-3. In some embodiments, the anti-TIM-3 antibody or anti-GALECTIN-9 antibody does not prevent GALECTIN-9 from binding to TIM-3. In some embodiments, the anti-TIM-3 antibody or anti-HMGB1 antibody prevents HMGB1 from binding to TIM-3. In some embodiments, the anti-TIM-3 antibody or anti-HMGB1 antibody does not prevent HMGB1 from binding to TIM-3.

In some embodiments, the genetically modified animals can be used for determining whether an anti-TIM-3 antibody is an TIM-3 agonist or antagonist. In some embodiments, the methods as described herein are also designed to determine the effects of the agent (e.g., anti-TIM-3 antibodies) on TIM-3, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-TIM-3 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-TIM-3 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-TIM-3 antibody is designed for treating hepatocellular, ovarian, colon, or cervical carcinomas.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the TIM-3 gene function, human TIM-3 antibodies, drugs for human TIM-3 targeting sites, the drugs or efficacies for human TIM-3 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric TIM-3 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (TNFRSF4; or OX40).

The methods of generating genetically modified animal model with two or more human or chimeric genes (e.g., humanized genes) can include the following steps:

(a) using the methods of introducing human TIM-3 gene or chimeric TIM-3 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, 4-1BB, CD27, CD28, CD47, TIGIT, CD27, GITR, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024; each of which is incorporated herein by reference in its entirety.

In some embodiments, the TIM-3 humanization is directly performed on a genetically modified animal having a human or chimeric PD-1, CTLA-4, BTLA, PD-L1, 4-1BB, CD27, CD28, CD47, TIGIT, CD27, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-TIM-3 antibody and an additional therapeutic agent for the treatment of cancer. The methods include administering the anti-TIM-3 antibody and the additional therapeutic agent to the animal, wherein the animal has a tumor; and determining the inhibitory effects of the combined treatment to the tumor.

In some embodiments, the animal further comprises a sequence encoding a human or humanized programmed cell death protein 1 (PD-1), or a sequence encoding a human or humanized CTLA4. In some embodiments, the additional therapeutic agent is an anti-PD-1 antibody (e.g., nivolumab, pembrolizumab) or an CTLA-4 antibody. In some embodiments, the tumor comprises one or more tumor cells that express GALECTIN-9, HMGB1, CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, and/or prostate cancer (e.g., metastatic hormone-refractory prostate cancer).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods
The following materials were used in the following examples.

Ambion™ in vitro transcription kit was purchased from Ambion. Catalog number is AM1354.

*E. coli* TOP10 competent cells were purchased from the Tiangen Biotech (Beijing) Co. Catalog number is CB104-02.

EcoRI, BamHI, BbsI, NdeI, XbaI were purchased from NEB. Catalog numbers are R3101M, R3136M, R0539L, R0111L, and R0145M.

Kanamycin was purchased from Amresco. Catalog number is 0408.

Cas9 mRNA was obtained from SIGMA. Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

Reverse Transcription Kit was obtained from Takara. Catalog number is 6110A.

C57BL/6 mice were purchased from the China Food and Drugs Research Institute National Rodent Experimental Animal Center.

B-hPD-1 mice were obtained from Beijing Biocytogen Co., Ltd.

Mouse colon cancer cell line MC38 was purchased from Shanghai Enzyme Research Biotechnology Co., Ltd.

Mouse CD3 antibody was obtained from BD. Catalog number is 563123.

mTIM-3 APC was obtained from Biolegend. Catalog number is 119706.

hTIM-3 PE was obtained from Biolegend. Catalog number is 345006.

mTcRβ PerCP was obtained from Biolegend. Catalog number is 109228.

mPD-1 PE was obtained from Biolegend. Catalog number is 109104.hPD-1 FITC was obtained from Biolegend. Catalog number is 329904.

The flow cytometer was purchased from BD Biosciences (model: FACS Calibur™)

Example 1: Construction of pT7-TIM-3 and pT7-TIM-8

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA6) and the 3'-terminal targeting sites (sgRNA7 to sgRNA13) were designed and synthesized. The 5'-terminal targeting sites and the 3'-terminal targeting sites are located on exon 2 of mouse TIM-3 gene, and the targeting site sequence on TIM-3 of each sgRNA is as follows:

```
sgRNA-1 targeting sequence:
5'-TCCTTACTTTATAGGGTCATTGG-3'       (SEQ ID NO: 1)

sgRNA-2 targeting sequence:
5'-AGTGTAACTGCAGGGCAGATAGG-3'       (SEQ ID NO: 2)

sgRNA-3 targeting sequence:
5'-GGAAAATGCTTATGTGTTTGAGG-3'       (SEQ ID NO: 3)

sgRNA-4 targeting sequence:
5'-TGTAGATAGAGTGTAACTGCAGG-3'       (SEQ ID NO: 4)

sgRNA-5 targeting sequence:
5'-GTTACACTCTATCTACACCTGGG-3'       (SEQ ID NO: 5)
```

-continued sgRNA-6 targeting sequence:
5'-CACATAGGCACAAGTGCCCCAGG-3'    (SEQ ID NO: 6)

sgRNA-7 targeting sequence:
5'-CTGAAATTAGACATCAAAGCAGG-3'    (SEQ ID NO: 7)

sgRNA-8 targeting sequence:
5'-ATGTGACTCTGGATGACCATGGG-3'    (SEQ ID NO: 8)

sgRNA-9 targeting sequence:
5'-GATCATAAAGAATGTGACTCTGG-3'    (SEQ ID NO: 9)

sgRNA-10 targeting sequence:
5'-TCCAGCAGATACCAGCTAAAGGG-3'    (SEQ ID NO: 10)

sgRNA-11 targeting sequence:
5'-CTAAAGGGCGATCTCAACAAAGG-3'    (SEQ ID NO: 11)

sgRNA-12 targeting sequence:
5'-TGTTGAGATCGCCCTTTAGCTGG-3'    (SEQ ID NO: 12)

sgRNA-13 targeting sequence:
5'-GCCCTTTAGCTGGTATCTGCTGG-3'    (SEQ ID NO: 13)

Figure 1B:
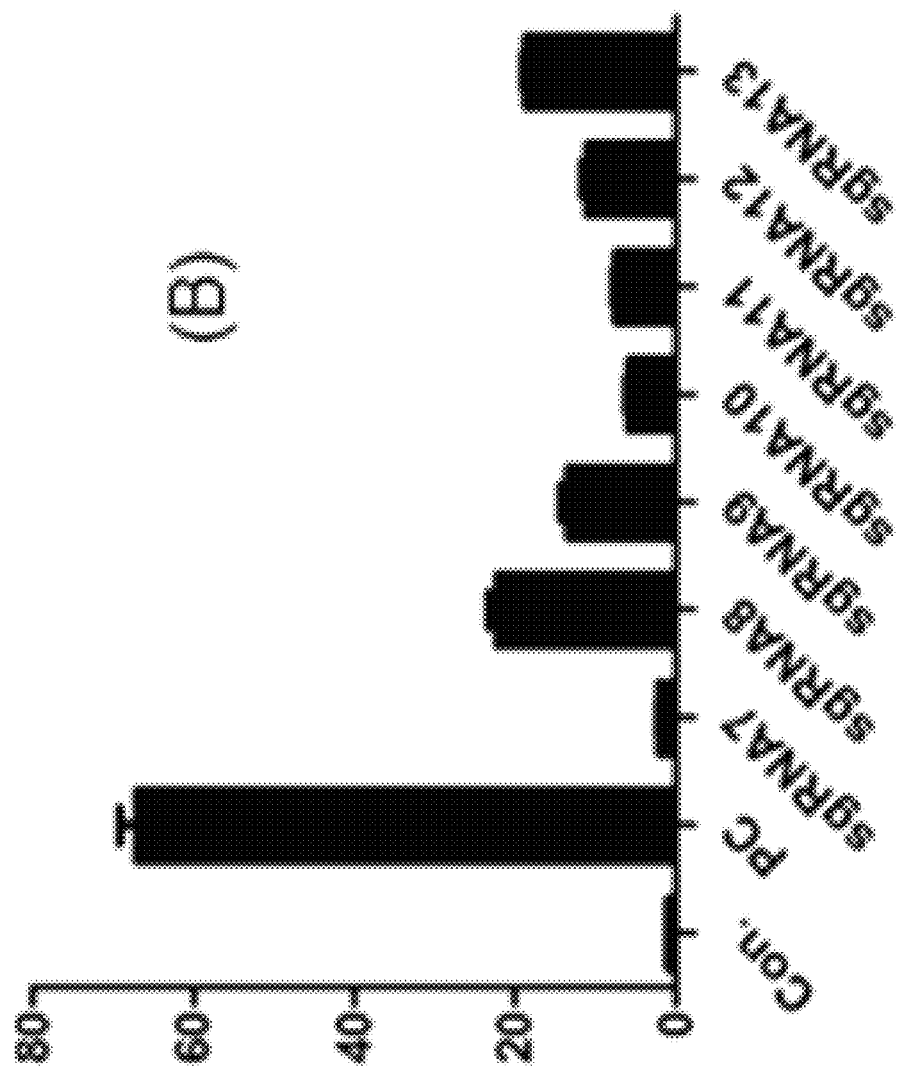
FIG. 1B is a graph showing activity testing results for sgRNA7-sgRNA13 (Con is a negative control; and PC is a positive control).

The UCA kit was used to detect the activities of sgRNAs (FIGS. 1A and 1B). The results show that the guide sgRNAs have different activities. Two of them (sgRNA3 and sgRNA8) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-TIM-3 and pT7-TIM-8.

TABLE 3 sgRNA3 and sgRNA8 sequences sgRNA3 sequences

| SEQ ID NO: 14 | Upstream:<br>5'-AAAATGCTTATGTGTTTG-3' |
|---|---|
| SEQ ID NO: 15<br>(adding TAGG to obtain a forward oligonucleotide sequence) | Upstream:<br>5'-TAGGAAAATGCTTATGTGTTTG-3' |
| SEQ ID NO: 16 | Downstream:<br>5'-CAAACACATAAGCATTTT-3' |
| SEQ ID NO: 17<br>(complementary strand was added with AAAC to obtain a reverse oligonucleotide sequence) | Downstream:<br>5'-AAACCAAACACATAAGCATTTT-3' | sgRNA8 sequences

| SEQ ID NO: 18 | Upstream:<br>5'-TGACTCTGGATGACCAT-3' |
|---|---|
| SEQ ID NO: 19<br>(adding TAGG to obtain a forward oligonucleotide sequence) | Upstream:<br>5'-TAGGTGACTCTGGATGACCAT-3' |
| SEQ ID NO: 20 | Downstream:<br>5'-ATGGTCATCCAGAGTCA-3' |

TABLE 3-continued sgRNA3 and sgRNA8 sequences

| SEQ ID NO: 21<br>(complementary strand was added with AAAC to obtain a reverse oligonucleotide sequence) | Downstream:<br>5'-AAACATGGTCATCCAGAGTCA-3' |
|---|---|

TABLE 4

The ligation reaction conditions (10 μL)

| Double stranded fragment | 1 μL (0.5 μM) |
|---|---|
| pT7-sgRNA vector | 1 μL (10 ng) |
| T4 DNA Ligase | 1 μL (5 U) |
| 10x T4 DNA Ligase buffer | 1 μL |
| 50% PEG4000 | 1 μL |
| H₂O | Add to 10 μL |

Reaction Conditions:

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-TIM-3 and pT7-TIM-8 were selected for subsequent experiments.

Source of pT7-sgRNA Plasmid

PT7-sgRNA vector map is shown in FIG. 2. The plasmid backbone was obtained from Takara (Catalog No. 3299). The DNA fragment containing T7 promoter and sgRNA scaffold was synthesized by a plasmid synthesis company, and linked to the backbone vector by restriction enzyme digestion (EcoRI and BamHI) and ligation. The target plasmid was confirmed by the sequencing results.

The DNA fragment containing the T7 promoter and sgRNA scaffold (SEQ ID NO: 22):

GAATTCTAATACGACTCACTATAGGGGGTCTTCGAGAAGACCTGTTTT

AGAGCTAGAAATAGCAAGTTAAAATAAGGCTAGTCCGTTATCAACTTGAA

AAAGTGGCACCGAGTCGGTGCTTTTAAAGGATCC

Example 2. Construction of Vector pClon-4G-TIM

A partial coding sequence of the mouse TIM-3 gene (Gene ID: 171285) from exon 2 (based on the transcript of NCBI accession number NM_134250.2→NP_599011.2 whose mRNA sequence is shown in SEQ ID NO: 23, and the corresponding protein sequence is shown in SEQ ID NO: 24) was replaced with a corresponding coding sequence of human homologous TIM-3 gene (Gene ID: 84868) (based on the transcript of NCBI accession number NM_032782.4→NP_116171.3, whose mRNA sequence was shown in SEQ ID NO: 25, and the corresponding protein sequence is shown in SEQ ID NO: 26). The comparison between the mouse TIM-3 and human TIM-3 is shown in FIG. 3A, and the finally obtained humanized TIM-3 gene is shown in FIG. 3B, the humanized mouse TIM-3 gene DNA sequence (chimeric TIM-3 gene DNA) is shown in SEQ ID NO: 27.

TTATAGGGTCA<u>*TCAGAAGTGGAATACAGAGCGGAGGTCGGTCAGAATGCC*</u>

<u>*TATCTGCCCTGCTTCTACACCCCAGCCGCCCCAGGGAACCTCGTGCCCGT*</u>

<u>*CTGCTGGGGCAAAGGAGCCTGTCCTGTGTTTGAATGTGGCAACGTGGTGC*</u>

<u>*TCAGGACTGATGAAAGGGATGTGAATTATTGGACATCCAGATACTGGCTA*</u>

<u>*AATGGGGATTTCCGCAAAGGAGATGTGTCCCTGACCATAGAGAATGTGAC*</u>

<u>*TCTAGCAGACAGTGGGATCTACTGCTGCCGGATCCAAATCCCAGGCATAA*</u>

<u>*TGAATGATGAAAAATTTAACCTGAAGTTGGTC*</u>ATCAAAGCAG

SEQ ID NO: 27 lists only the portion of DNA sequence involved in the modification, wherein the italicized underlined region is the human TIM-3 gene sequence fragment.

The coding region sequence, mRNA sequence and the encoded protein sequence thereof of the modified humanized TIM-3 are respectively shown in SEQ ID NO: 28, SEQ ID NO: 29, and SEQ ID NO: 30.

To the extent that either human TIM-3 or mouse TIM-3 has more than one isoform, the methods as described herein can be applied to other isoforms.

A targeting strategy involving a vector comprising the 5' end homologous arm, human TIM-3 gene fragment, 3' homologous arm as shown in FIG. 3C is also developed. The process is as follows:

(1). Design upstream primers of homologous recombination fragments, and downstream primers matching therewith, as well as other related sequences. Specifically:

5' end homologous arm (SEQ ID NO: 31), nucleotide sequence of the positions from 46454902 to 46456260 of the NCBI accession number NC_000077.6 as follows:

```
Upstream primer (SEQ ID NO: 32):
F:
5'-tttaagaaggagatatacatggagctcattctggggactcaggagtt agagg-3'

Downstream primer (SEQ ID NO: 33):
R:
5'-gtattccacttctgatgaccctataaagtaaggaaaggaggtcag-

3'
```

(2). Design the primers and related sequences of the desired conversion region. Human DNA fragment (321 bp) (SEQ ID NO: 34) is the nucleotide sequence from positions 157106637 to 157106957 of the NCBI accession number NC_000005.10.

```
The upstream primer (SEQ ID NO: 35) is:
F:
5'-cttactttatagggtcatcagaagtggaatacagagcggagg-3'

The downstream primer (SEQ ID NO: 36) is:
R:
5'-ctcacctgctttgatgaccaacttcaggttaaatttttcatcattc-

3'
```

(3). Design the upstream primers of the homologous recombination fragment and the downstream primers matching therewith, as well as other related sequences. Specifically:

3' homologous arm (SEQ ID NO: 37), which was the nucleotide sequence from positions 46456585 to 46457884 of the NCBI accession number NC_000077.6:

```
Upstream primer (SEQ ID NO: 38):
F:
5'-aacctgaagttggtcatcaaagcaggtgagtagacctttcc-3'

Downstream primer (SEQ ID NO: 39):
R:
5'-ttgttagcagccggatctcagaagcttatctactgeggaggaaggtc aaatg-3'
```

C57BL/6 mouse DNA is used as the template to carry out PCR amplification for the 5'-terminal homologous arm fragment and the 3'-terminal homologous arm fragment. Human DNA is used as the template to carry out PCR amplification for the DNA fragment, and the AIO kit is used to ligate the fragments to the pClon-4G plasmid provided by the kit, so as to obtain the vector pClon-4G-TIM.

Example 3. Verification of Vector pClon-4G-TIM

Figure 4:
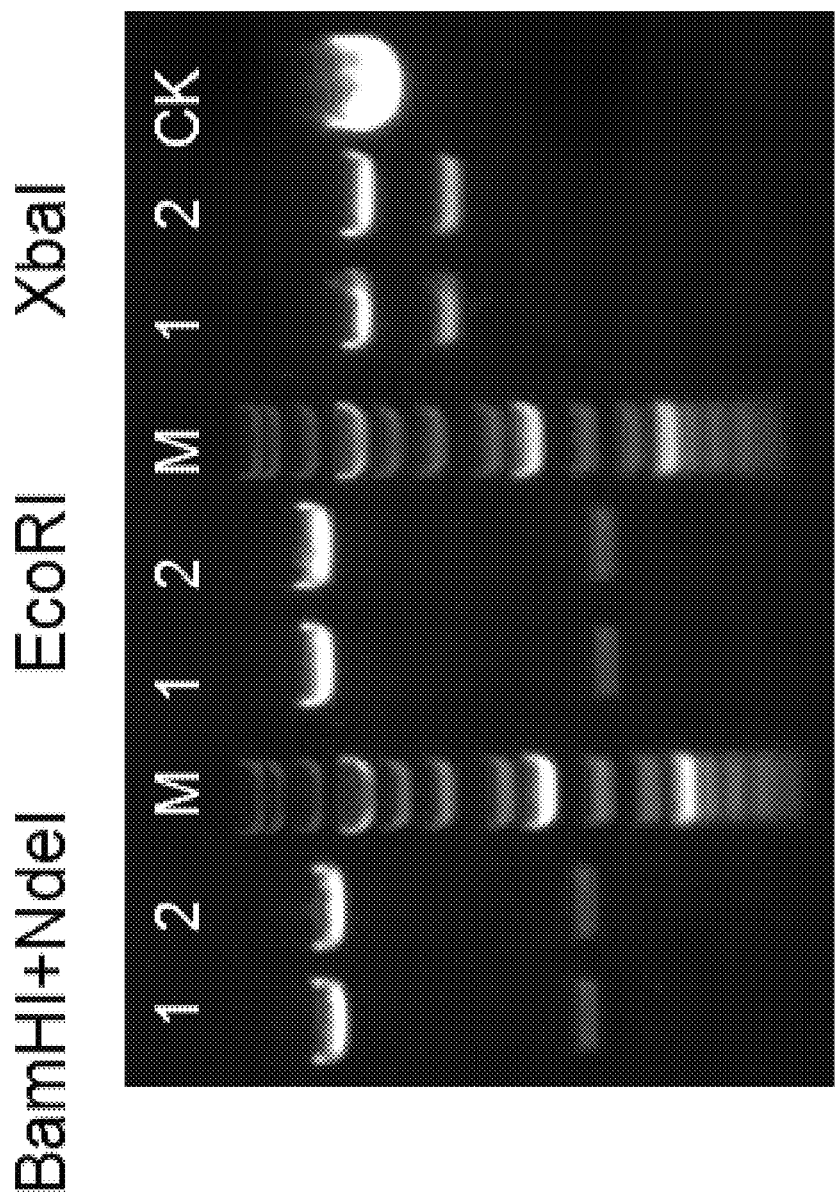
FIG. 4 shows pClon-4G-TIM plasmid digestion result (M is the Marker, CK is undigested plasmid).

Two pClon-4G-TIM clones were randomly selected and identified by three sets of enzymes. Among them, BamHI+NdeI should generate 5447 bp+1048 bp fragments, EcoRI should generate 5677 bp+818 bp fragments, XbaI should generate 4207 bp+2288 bp fragments. The results were in line with the expectations (FIG. 4). The sequences of Plasmids 1 and 2 were further verified by sequencing. Plasmid 2 was selected for subsequent experiments.

Example 4. Microinjection and Embryo Transfer

The pre-mixed Cas9 mRNA, pClon-4G-TIM plasmid and in vitro transcription products of pT7-TIM-3, pT7-TIM-8 plasmids were injected into the cytoplasm or nucleus of mouse fertilized eggs (C57BL/6 background) with a microinjection instrument (using in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mice population was further expanded by cross-mating and self-mating to establish stable mouse lines. The humanized mouse was named as B-hTIM-3 mouse.

Example 5. Verification of Genetically Modified Humanized Mouse Model

1. Genotype Determination for F0 Generation Mice

PCR analysis was performed for mouse tail genomic DNA of F0 generation mice. The primers are for exon 2 of mouse TIM-3 gene. The primers for PCR-1 were located on the left side of the 5' homologous arm, the primers for PCR-4 were located on the right side of the 3' homologous arm; in addition, the primers for PCR-2 and PCR-3 were located on the humanized fragment, which are shown below:

```
5' terminus primers:
PCR-1 (SEQ ID NO: 40):
5'-ctcagagtgccttgcagggtgtatc-3'

PCR-2 (SEQ ID NO: 41):
5'-ttgcggaaatccccatttagccagt-3'

3' terminus primers:
PCR-3 (SEQ ID NO: 42):
5'-gcaaaggagcctgtcctgtgtttgaatg-3'

PCR-4 (SEQ ID NO: 43):
5'-cgcaagcaccaagaggagatggaaa-3'
```

If the recombinant vector has the correct insertion, there should be one PCR product band from the PCR reaction by the 5' terminus primers (1719 bp), and one PCR product band from the PCR reaction by the 3' terminus primers (1883 bp).

TABLE 5

The PCR reaction system (20 μL)

| | |
|---|---|
| 10× buffer | 2 μL |
| dNTP (2 mM) | 2 μL |
| MgSO₄ (25 mM) | 0.8 μL |
| Upstream primer (10 μM) | 0.6 μL |
| Downstream primer (10 μM) | 0.6 μL |
| Mouse tail genomic DNA | 200 ng |
| KOD-Plus-(1 U/μL) | 0.6 μL |

TABLE 6

The PCR reaction conditions

| Temperature | Time | Cycles |
|---|---|---|
| 94° C. | 5 min | 1 |
| 94° C. | 30 sec | 15 |
| 67° C. (−0.7° C./cycle) | 30 sec | |
| 68° C. | 1 kb/min | |
| 94° C. | 30 sec | 25 |
| 56° C. | 30 sec | |
| 68° C. | 1 kb/min | |
| 68° C. | 10 min | 1 |
| 4° C. | 10 min | 1 |

Figure 5:
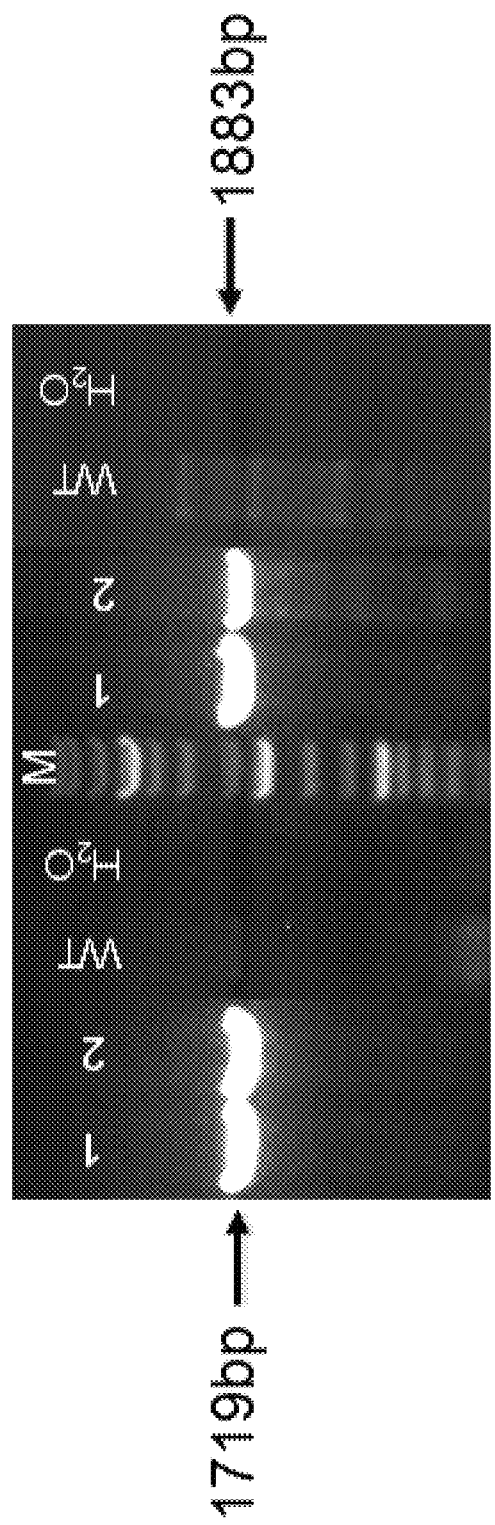
FIG. 5 shows PCR identification result of samples collected from tails of F0 generation mice (M is the Marker; WT is wildtype; mice labeled with No. 1 and 2 are positive).

The verification results for two F0 generation mice are shown in FIG. 5.

2. Genotype Determination for F1 Generation Mice

Figure 6:
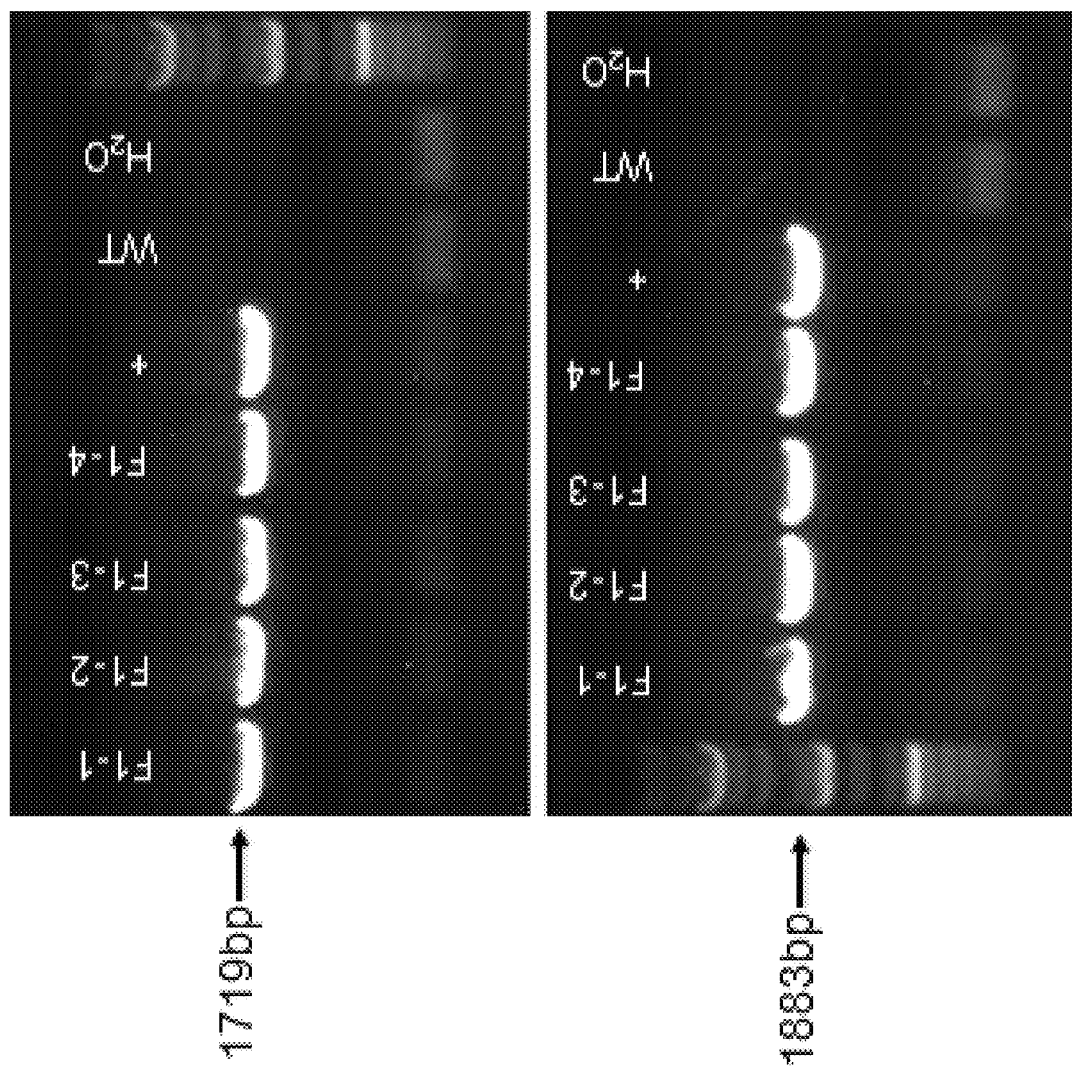
FIG. 6 shows PCR identification result of samples collected from tails of F1 generation mice (M is the Marker; WT is wildtype; + is positive control; mice labeled with F1-1 to F1-4 are all positive).

F1 generation mice were obtained by cross-mating F0 generation mice with C57BL/6 mice. PCR was performed for four F1 generation mice with the same primers under the same conditions used for F0 verification. The results showed that all four F1 generation mice were positive (FIG. 6).

These four mice were further examined by Southern blotting to determine whether they had a random insertion. The genomic DNA was extracted from the mouse tail, and BamHI was used to digest the genomic DNA. The digestion products were transferred to membrane and hybridized. The probes P1 and P2 were located respectively outside of the 3' homologous arm, and on the 5' homologous arm. The primers for probe synthesis are as follows:

```
P1-F (SEQ ID NO: 44):
5'-atgttcactccctgtcaactggttg-3'

P1-R (SEQ ID NO: 45):
5'-tctgctccacatgaccacaaagatg-3'

P2-F (SEQ ID NO: 46):
5'-cagagctgtccttggatttcccctg-3'

P2-R (SEQ ID NO: 47):
5'-gactgcaagcatgactcctctccca-3'
```

The wildtype C57BL/6 mice would have an 8.2 kb band for both P1 probe and P2 probe. The genetically engineered homozygous mice should have a 4.0 kb band (P1 probe) or a 4.3 kb band (P2 probe). The genetically engineered heterozygous mice should have an 8.2 kb band and a 4.0 kb band (P1 probe), or an 8.2 kb and a 4.3 kb band (P2 probe). No other band should be present.

Figure 7:
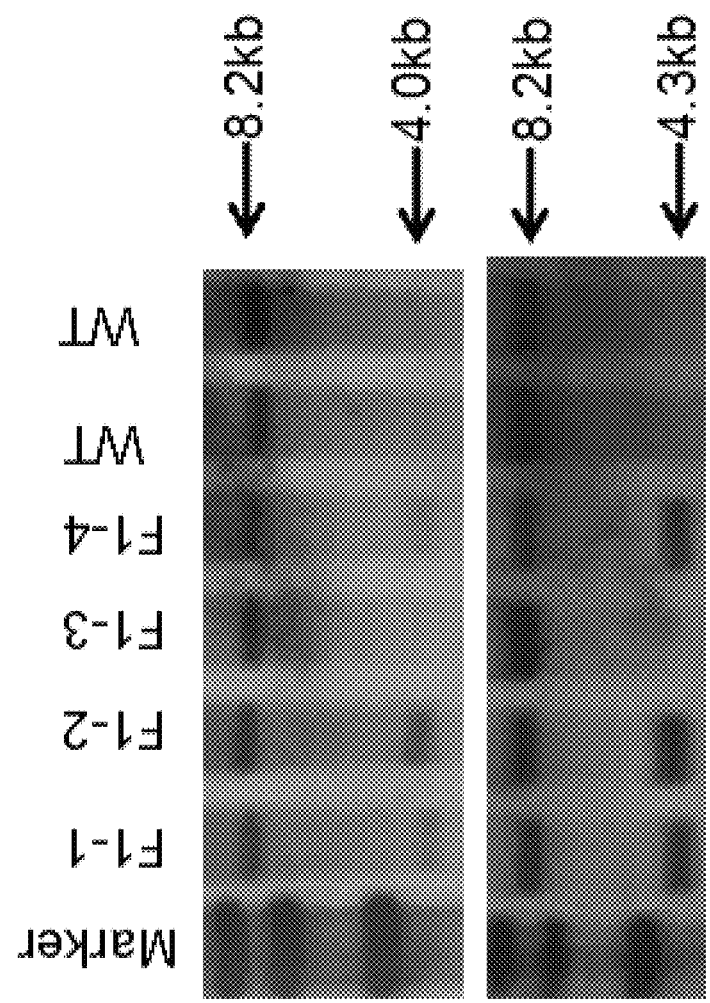
FIG. 7 shows Southern blot results for F1 generation mice by P1 and P2 probes (WT is wildtype). The results show that the mice labeled with F1-1, F1-2, and F1-4 have no random insertion.

The results are shown in FIG. 7. F1-1, F1-2, and F1-4 showed the expected bands for both the P1 probe and the P2 probe, without any other bands. The results confirmed that F1-1, F1-2, and F1-4 were positive heterozygous mice with no random insertions.

It thus shows that this method can be used to generate humanized B-hTIM-3 mice that have no random insertion.

3. Protein Expression Analysis for Heterozygous F1 Generation Mouse

A humanized heterozygous F1 generation mouse was selected for this experiment. One wildtype C57BL/6 mouse was used as the control.

7.5 μg of mouse anti-CD3 antibody was injected intraperitoneally to the mice. The spleens were collected 24 hours after the injection, and the spleen samples were grinded. The ground samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed once with PBS.

Figures 8A, 8B, 8C, 8D, 8E, 8F:
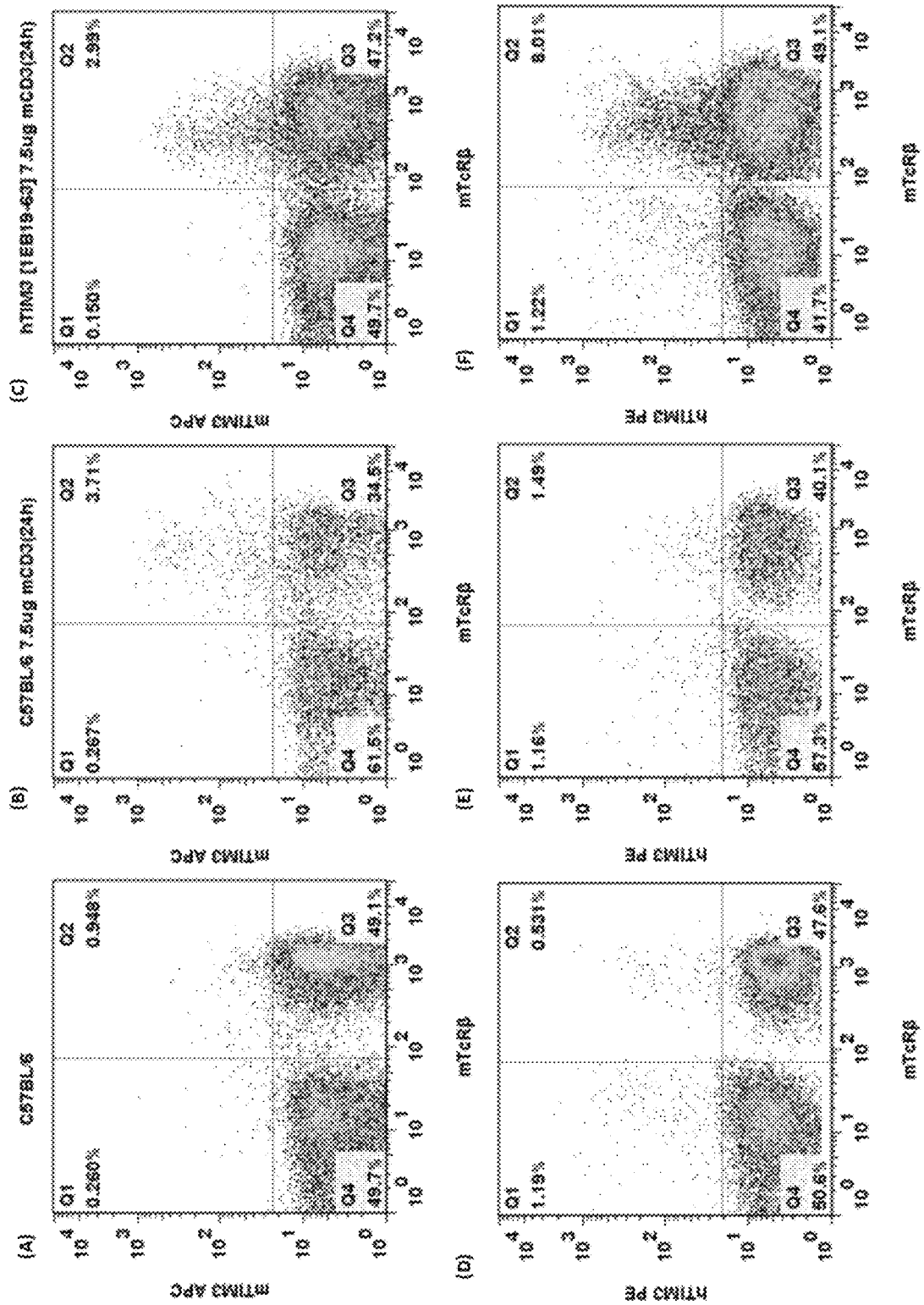
FIGS. 8A-8F are results of flow cytometry analysis for C57BL/6 mice and TIM-3 humanized mice. The anti-mouse CD3 antibody was used to stimulate the T cells in the spleen, and then fluorescent anti-mouse TIM-3 antibodies (FIGS. 8A-8C) or fluorescent anti-human TIM-3 antibodies (FIGS. 8D-8F) were used to label cells. Compared to the control group (FIGS. 8A and 8D), the cells with the expression of humanized TIM-3 protein can be detected in the spleen of TIM-3 humanized F1 hybrids (FIG. 8F); whereas in the spleen of C57BL/6 mice, no cells expressing humanized TIM-3 protein were detected (FIG. 8E).

FACS:

T cells in C57BL/6 mice and humanized TIM-3 mice were first activated with anti-CD3 antibody. Then, anti-mouse TIM-3 antibodies (mTIM-3 APC) and anti-mTCRβ antibody (TCRβ PerCP), or anti-human TIM-3 antibodies (hTIM-3 PE) and anti-mTCRβ antibody (TCRβ PerCP) were used to stain the cells. The cells were washed once with PBS and analyzed with flow cytometry. The results of flow cytometry (FIGS. 8A-8F) showed that when compared with the C57BL/6 mice without anti-CD3 antibody stimulation (FIGS. 8A and 8D) or with anti-CD3 antibody stimulation (FIGS. 8B and 8E), the humanized mouse spleen (FIGS. 8C and 8F) had cells expressing humanized TIM-3 proteins as detected by anti-human TIM-3 antibody, while the spleen of the C57BL/6 control mice did not have detectable cells expressing humanized TIM-3 proteins (FIGS. 8D, and 8E). The foregoing results indicate that the genetically modified TIM-3 humanized mice were able to express humanized TIM-3 proteins, which can be detected by an anti-human TIM-3 antibody. In contrast, humanized TIM-3 protein cannot be detected in C57BL/6 mice.

RT-PCR Detection:

RNA was extracted from the spleen cells, and cDNA were then obtained by reverse transcription using a reverse transcription kit.

```
Primers for mTIM-3 RT-PCR:
mTIM-3 RT-PCR F1 (SEQ ID NO: 48):
CCTATCTGCCCTGCAGTTAC,
and mTIM-3 RT-PCR R1 (SEQ ID NO: 49):
TTCATAAGACCAGGGAACTG
``` were used to amplify mouse TIM-3 fragment of 259 bp.

```
Primers for hTIM-3 RT-PCR:
hTIM-3 RT-PCR F1 (SEQ ID NO: 50):
ATCTGCCCTGCTTCTACACC,
and hTIM-3 RT-PCR R1 (SEQ ID NO: 51) :
GCGGAAATCCCCATTTAGCC
``` were used to amplify human TIM-3 fragment of 164 bp.

PCR reaction system was 20 μL, reaction conditions: 95° C., 5 min; (95° C., 30 sec; 60° C., 30 sec; 72° C., 30 sec, 35 cycles); 72° C., 10 min; and then keeping it at 4° C. GAPDH was used as an internal reference.

Figure 9:
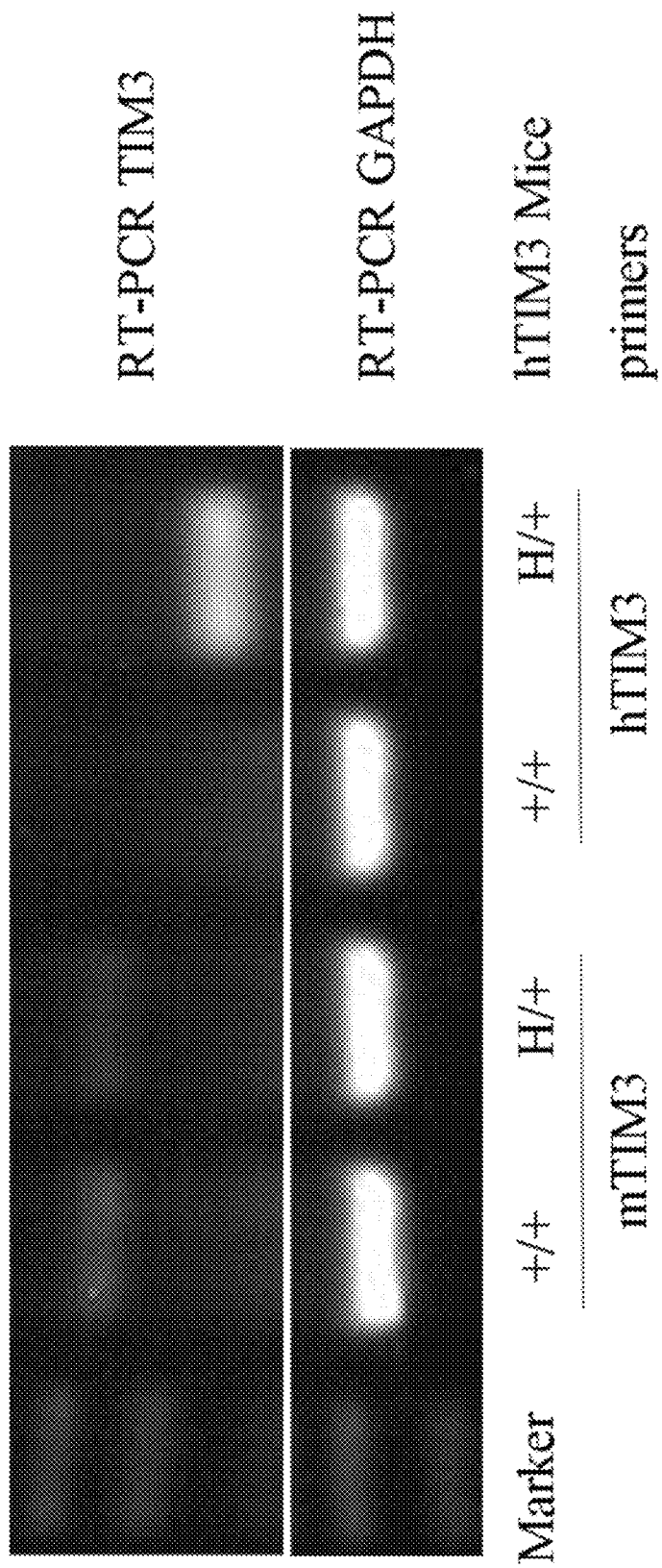
FIG. 9 shows RT-PCR detection results, wherein +/+ is wildtype C57BL/6 mouse; H/+ is F1 generation hTIM-3 heterozygous mouse; and GAPDH is an internal control.

The results are shown in FIG. 9. The mRNA expression of mouse TIM-3 was detected in the activated cells of wildtype C57BL/6 mice and F1 generation heterozygous mouse; while the mRNA expression of humanized TIM-3 was only detected in the activated cells of the F1 generation heterozygous mouse.

4. Protein Expression Analysis for B-hTIM-3 Homozygous Mice

The B-hTIM-3 genetically engineered homozygous mice were obtained by mating the previously obtained heterozygous mice with each other. One homozygous B-hTIM-3 mouse (6 weeks) was selected, and two wildtype C57BL/6 mouse were selected as a control. 7.5 μg of mouse anti-CD3 antibody was injected intraperitoneally to the mice, and the spleens of the mice were collected after 24 h. The spleen samples were ground and then filtered through a 70 μm cell filter, the obtained cell suspensions were centrifuged and the resulting supernatants were discarded. The cell samples were added with erythrocyte lysis solution for lysis of 5 min. Then PBS solution was added to neutralize the lysis reaction, followed by centrifugation where the supernatants were discarded. The cells were washed once again with PBS. The obtained samples were used in FACS and RT-PCR.

Figures 10A, 10B, 10C, 10D, 10E, 10F:
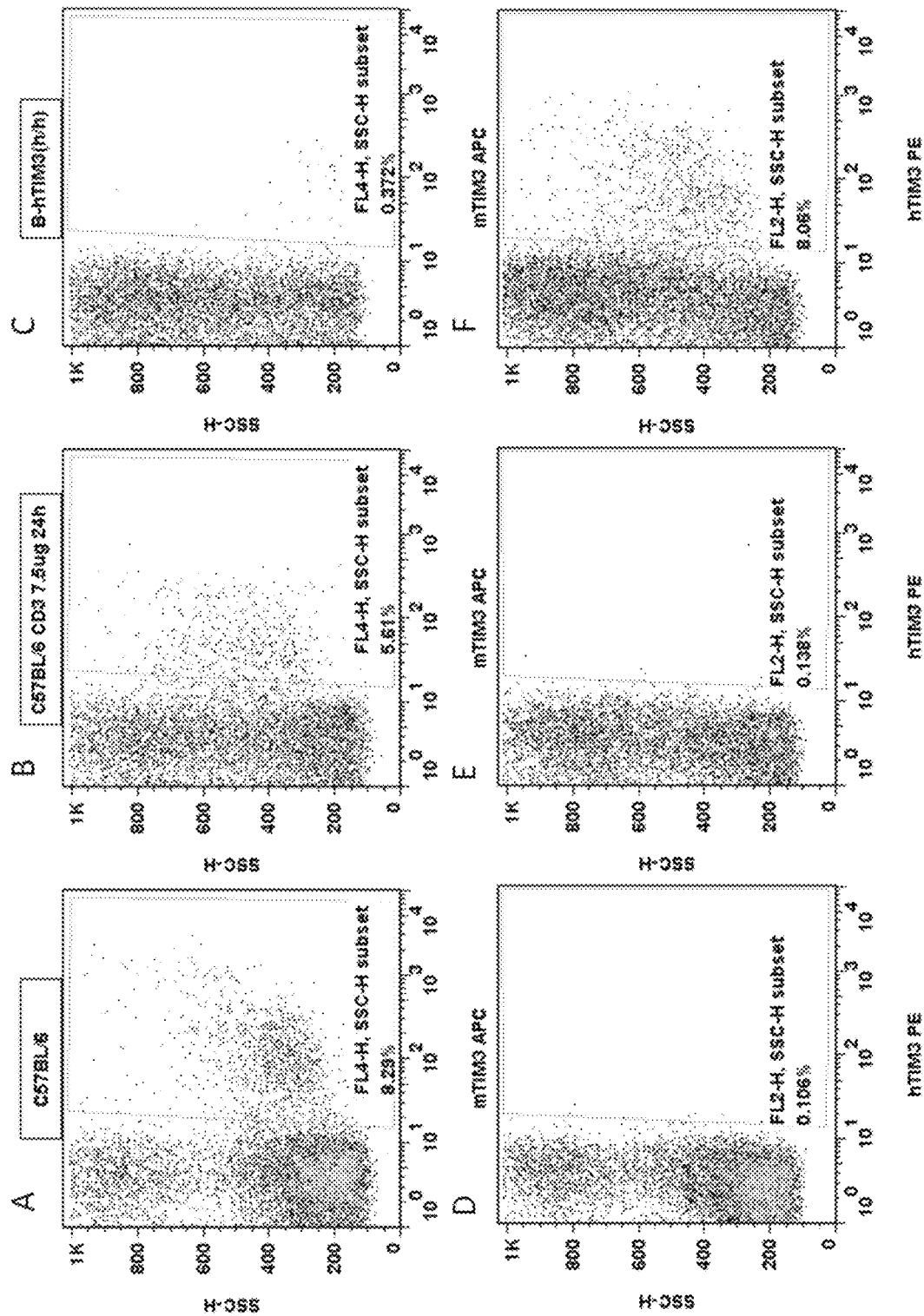
FIGS. 10A-10F are results of flow cytometry analysis for C57BL/6 mice and B-hTIM-3 homozygous mice. Anti-mouse CD3 antibody was used to stimulate the T cells in the spleen, and then anti-mouse TIM-3 antibodies (mTIM3 APC) or anti-human TIM-3 antibodies (hTIM-3 PE) were used to label the cells. Non-T and non-B cells expressing mouse TIM-3 proteins can be detected in the spleen of C57BL/6 mice (FIGS. 10A and 10B), but not cells expressing humanized TIM-3 (FIGS. 10D and 10E). Non-T and Non-B cells expressing humanized TIM-3 proteins can be detected in the spleen of hTIM-3 homozygous mice (FIG. 10F), but not cells expressing mouse TIM-3 proteins.

FACS Experiment 1:

Anti-mouse TIM-3 antibody (mTIM-3 APC) or anti-human TIM-3 antibody (hTIM-3 PE) were used to stain the cells, followed by PBS wash and Flow Cytometry analysis. The results are shown in FIGS. 10A-10F. Non-T and non-B cells in the spleens of C57BL/6 mice expressing mouse TIM-3 were detected with Fluorescent anti-mouse TIM-3 antibody (FIGS. 10A, 10B). No cell expressing mouse TIM-3 proteins was detected in the spleens of homozygous humanized TIM-3 mice (FIG. 10C). Non-T and non-B cells in the spleens of homozygous humanized TIM-3 mice expressing humanized TIM-3 were detected with Fluorescent anti-human TIM-3 antibody (FIG. 10F). No cell expressing humanized TIM-3 proteins was detected in the spleens of C57BL/6 control mice (FIG. 10D, 10E).

Figures 11A, 11B, 11C, 11D, 11E, 11F:
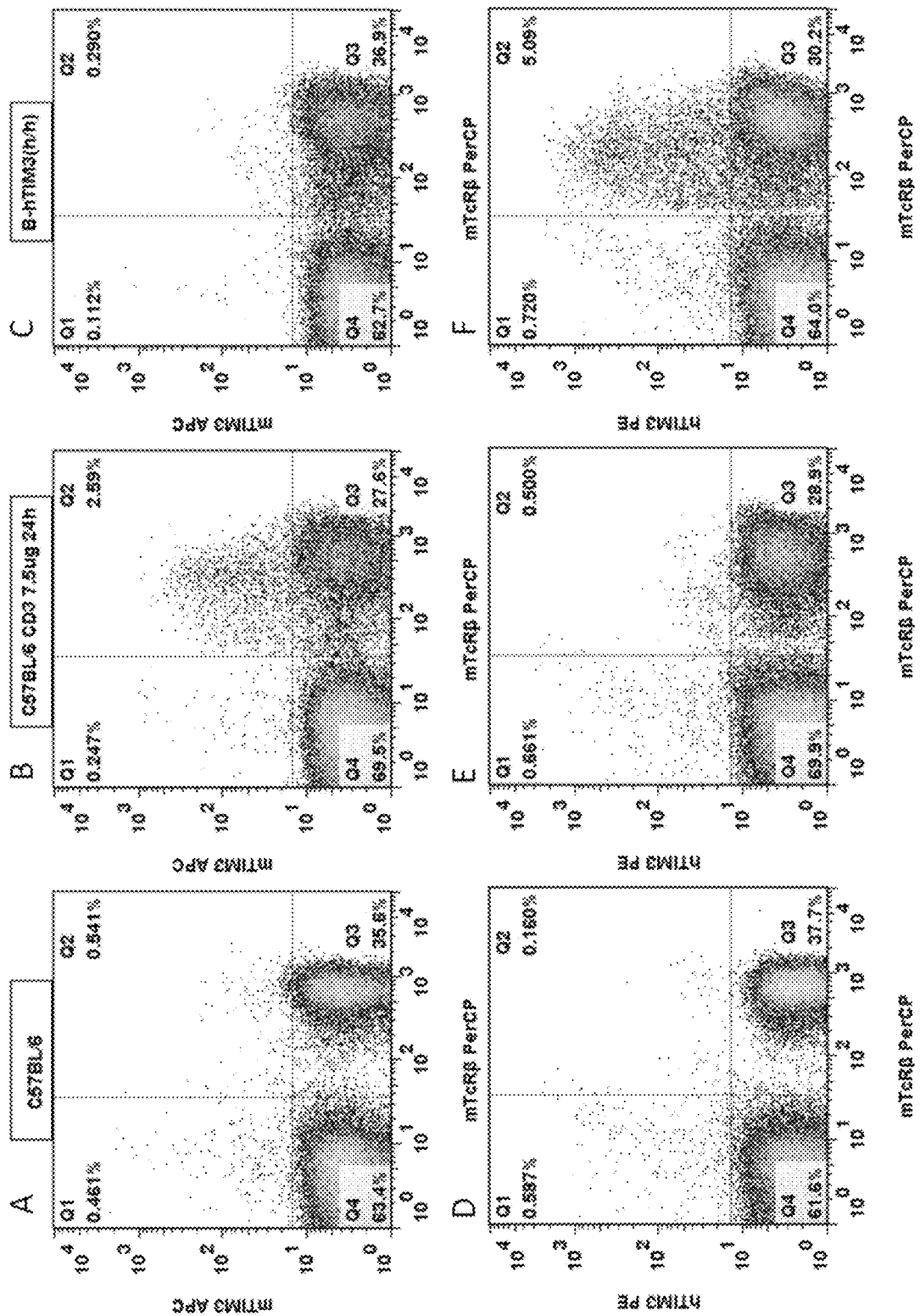
FIGS. 11A-11F are results of flow cytometry analysis for C57BL/6 mice and B-hTIM-3 homozygous mice. The anti-mouse CD3 antibody was used to stimulate the T cells in the spleen, and then anti-mouse TIM-3 antibodies (mTIM3 APC) and anti-mouse mTcRfβ antibody (mTcRβ PerCP) (FIGS. 11A-11C), or anti-human TIM-3 antibodies (hTIM-3 PE) and anti-mTcRfβ antibody (mTcRβ PerCP) (FIGS. 11D-11F), were used to label the cells. Cells expressing mouse TIM-3 proteins were detected in the spleen of C57BL/6 mice stimulated with CD3 antibodies (FIG. 11B), but not cells expressing humanized TIM-3 (FIG. 11E). Cells expressing humanized TIM-3 proteins were detected in the spleen of hTIM-3 homozygous mice stimulated with CD3 antibodies (FIG. 11F), but not cells expressing mouse TIM-3 proteins (FIG. 11C).

FACS Experiment 2:

Co-staining with anti-mouse TIM-3 antibody (mTIM-3 APC) and anti-mTCRβ antibody (TCRβ PerCP) or anti-human TIM-3 antibody (hTIM-3 PE) and anti-mTCRβ antibody (TCRβ PerCP) was carried out, followed by PBS wash and Flow Cytometry analysis. The results of Flow Cytometry are shown in FIGS. 11A-11F. Cells expressing mouse TIM-3 proteins in the spleens of C57BL/6 mice stimulated with CD3 antibody were detected with fluorescence labeled anti-mouse TIM-3 antibody (FIG. 11B). No cell expressing mouse TIM-3 protein was detected in the spleens of homozygous humanized TIM-3 mice (FIG. 11C). Cells expressing humanized TIM-3 proteins in the spleens of homozygous humanized TIM-3 mice were detected with fluorescence labeled anti-human TIM-3 antibody (FIG. 11F). No cell expressing humanized TIM-3 protein was detected in the spleens of C57BL/6 control mice (FIG. 11D, 11E).

The results above prove that the genetically modified humanized mice could express humanized TIM-3 proteins, detectable by an anti-human TIM-3 antibody.

Rt-PCR Detection:

Total RNA was extracted from the spleen cells of C57BL/6 mice and B-hTIM-3 homozygotes, and cDNA were then obtained by reverse transcription using a reverse transcription kit. mTIM-3 RT-PCR F1 (SEQ ID NO: 48) and mTIM-3 RT-PCR R1 (SEQ ID NO: 49) were used to amplify a mouse TIM-3 fragment of 259 bp. hTIM-3 RT-PCR F1 (SEQ ID NO: 50) and hTIM-3 RT-PCR R1 (SEQ ID NO: 51) were used to amplify a human TIM-3 fragment of 164 bp. The PCR reaction system was 20 reaction conditions: 95° C., 5 min; (95° C., 30 sec; 60° C., 30 sec; 72° C., 30 sec, 35 cycles); 72° C., 10 min; and then keeping it at 4° C. GAPDH was used as an internal reference.

Figure 12:
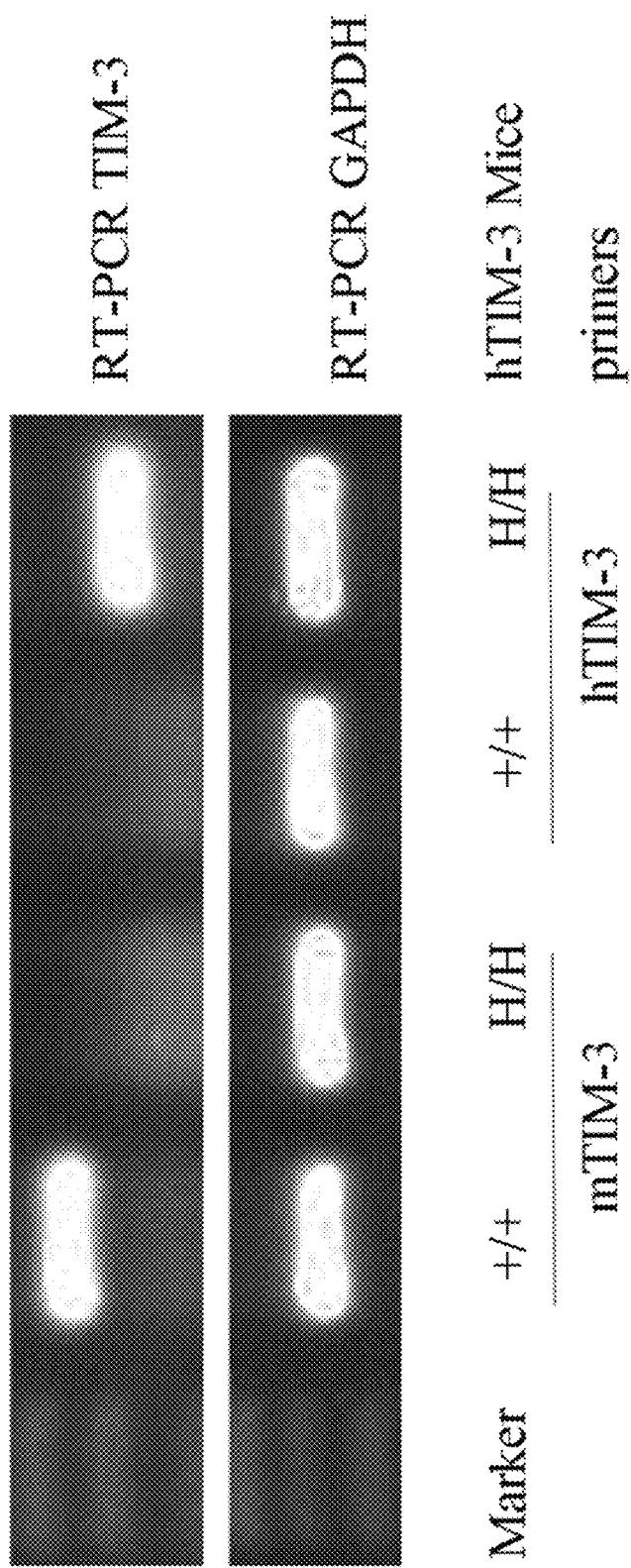
FIG. 12 shows RT-PCR detection results, wherein +/+ is wildtype C57BL/6 mouse; H/H is B-hTIM-3 homozygous mouse; and GAPDH is an internal control.

The results are shown in FIG. 12. The mRNA of mouse TIM-3 was detected in the activated cells of wildtype C57BL/6 mice (+/+); while the mRNA of humanized TIM-3 was only detected in B-hTIM-3 homozygotes (H/H).

Example 6. TIM-3 Knockout Mice

Since the cleavage of Cas9 results in DNA double strands break, and the homologous recombination repair may result in insertion/deletion mutations, it is possible to obtain TIM-3 knockout mouse when preparing the humanized TIM-3 mouse. A pair of primers was thus designed. They are located on the left side of the 5' end target site, and to the right side of the 3' end target site, which are shown as follows:

```
F:    5'-CAACAGGGCAGCCATAGTTTCCTCA-3' (SEQ ID NO: 52)

R:    5'-CACATGTGGAAGCTATACCACTGCA-3' (SEQ ID NO: 53)
```

Figure 13:
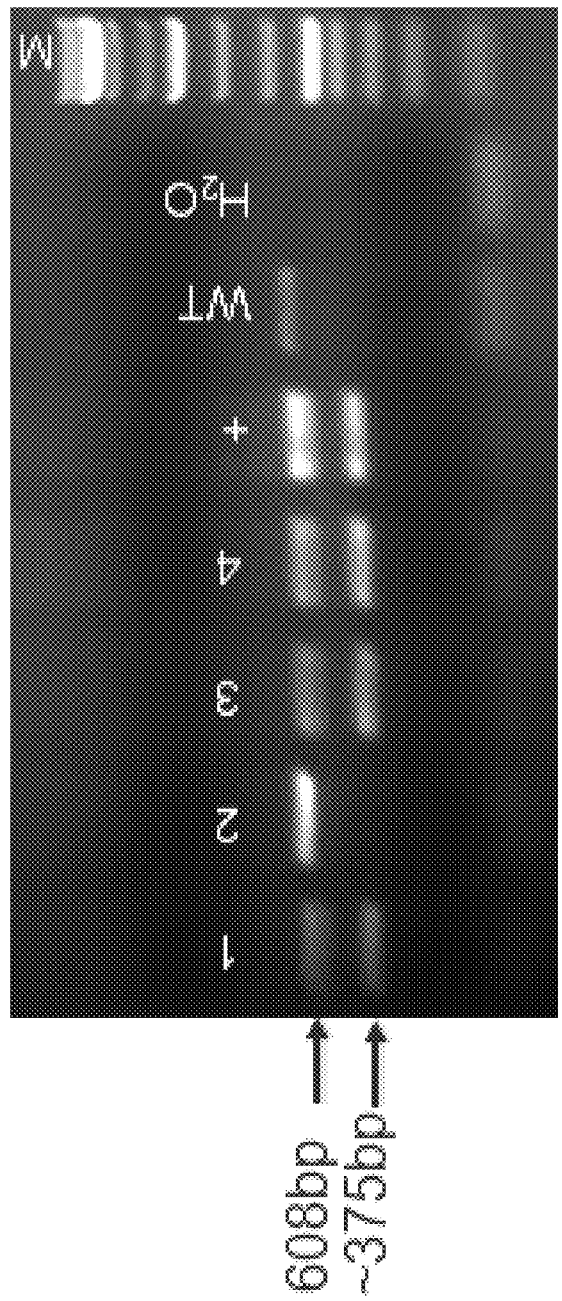
FIG. 13 shows PCR identification results for TIM-3 gene knockout mice, wherein WT is wildtype, M is the maker, + is the positive control, the mice with No. 1, No. 3, and No. 4 are TIM-3 knockout mice.

The PCR reaction systems and conditions are listed in Table 5 and Table 6. Under this condition, the wide type mice should have only one PCR band, and the product length should be approximately 608 bp. The heterozygous mice should have one additional band at approximately 375 bp. The results are shown in FIG. 13. Mouse 1, 3, 4 were heterozygous TIM3 knockout mice.

Example 7. Preparation and Identification of Mice with Double Humanized or Multiple Humanized Genes Mice containing the humanized TIM-3 gene (such as the B-hTIM-3 animal model prepared using the methods as described in the present disclosure) can also be used to prepare an animal model with double-humanized or multi-humanized genes. For example, in Example 4, the fertilized egg cells used in the microinjection and embryo transfer process can be selected from the fertilized egg cells of other genetically modified mice or the fertilized egg cells of B-hTIM-3 mice, so as to obtain double- or multiple-gene modified mouse models.

In addition, the B-hTIM-3 animal model homozygote or heterozygote can be mated with other genetically modified homozygous or heterozygous animal models, and the progeny is then screened; according to the Mendelian law, there is a chance to obtain the double-gene or multiple-gene modified heterozygous animal models, and then the obtained heterozygous can be mated with each other to finally obtain the double-gene or multiple-gene modified homozygotes.

In the case of the generating double humanized TIM-3/CTLA-4 mouse, since the mouse TIM-3 gene and CTLA-4 gene are located on different chromosomes, the double humanized TIM-3/CTLA-4 mouse was obtained by mating the B-hTIM-3 mouse with B-hCTLA-4 mouse (mice with humanized CTLA-4 gene).

Figures 14A, 14B, 14C, 14D:
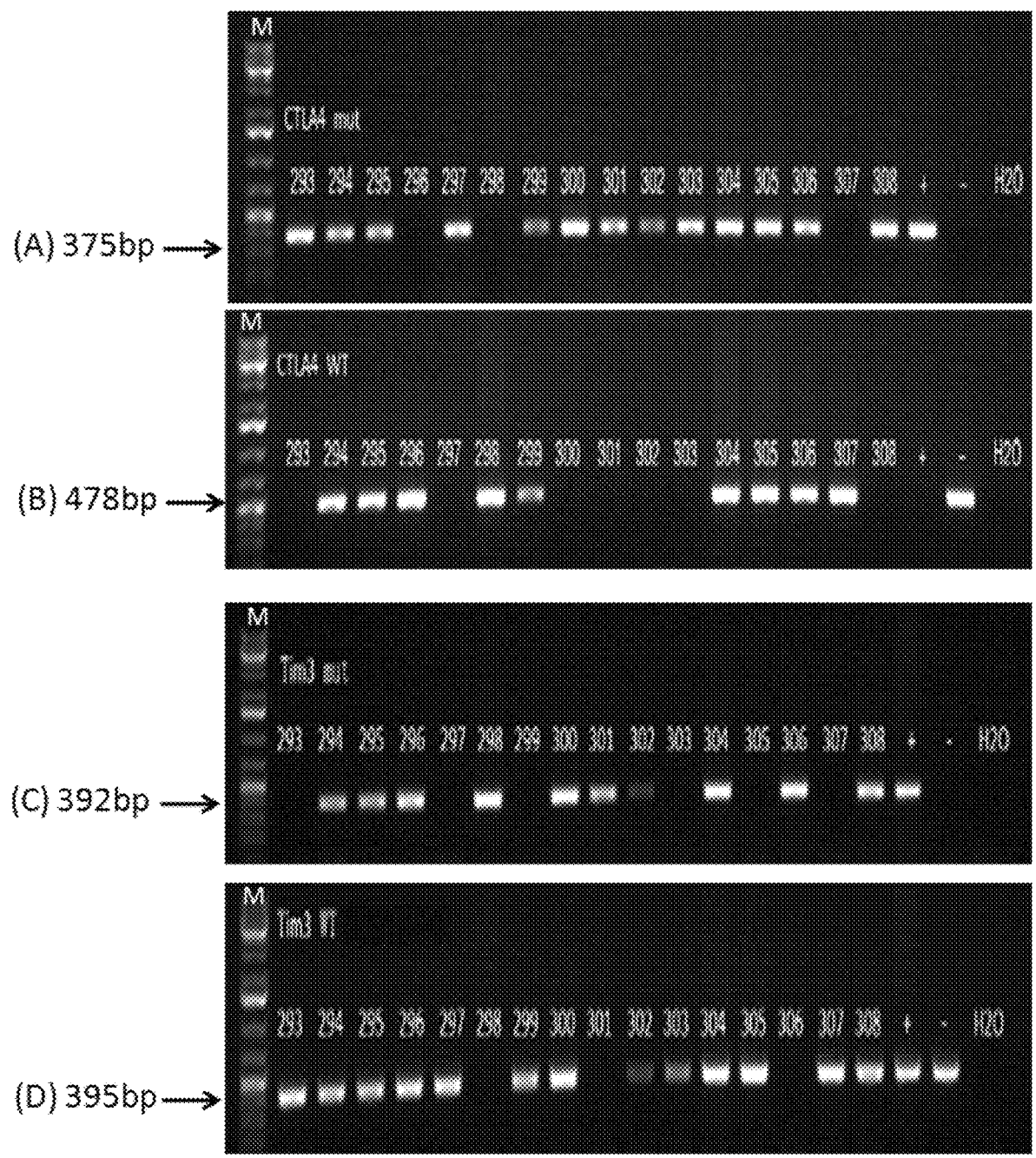
FIGS. 14A-14D. Mouse tail PCR identification results.

PCR analysis was performed on the mouse tail genomic DNA of double humanized TIM-3/CTLA-4 mice using four pairs of primers. The specific sequences and product lengths are shown in Table 7. The reaction system and reaction conditions are shown in Table 8 and Table 9. The results for a number of humanized TIM-3/CTLA-4 mice are shown in FIGS. 14A-14D, wherein FIGS. 14A and 14B show that the mice numbered 293, 297, 300, 301, 302, 303, and 308 were homozygous for humanized CTLA-4. FIGS. 14C and 14D show that the mice numbered 298, 301, and 306 were homozygous for humanized TIM-3, and the mice numbered 294, 295, 296, 300, 302, 304, 308 were heterozygous for humanized TIM-3. The combined results show that the mouse numbered 301 was homozygous for both humanized TIM-3 and humanized CTLA-4, the mice numbered 300, 302, and 308 were TIM-3$^{H/+}$/CTLA-4$^{H/H}$, the mouse numbered 306 was TIM-3$^{H/H}$/CTLA-4$^{H/+}$, and the mice numbered 294, 295, and 304 were TIM-3$^{H/+}$/CTLA-4$^{H/+}$.

TABLE 7

Primer sequences

| Primer | Sequence | Product length |
|---|---|---|
| TIM-3 WT | F: 5'-gtgtttgaatgtggcaacgtggtgc-3' (SEQ ID NO: 54) | WT: 395 bp |
| | R: 5'-cacatgtggaagctataccactgca-3' (SEQ ID NO: 53) | |
| TIM-3 MUT | F: 5'-tggtcacagtgtaccaacgagttgc-3' (SEQ ID NO: 55) | Mut: 392 bp |
| | R: 5'-cacatgtggaagctataccactgca-3' (SEQ ID NO: 53) | |
| CTLA-4 MUT | F: 5'-acagctgaaagatgggaagtggagt-3' (SEQ ID NO: 56) | Mut: 375 bp |
| | R: 5'-tcaactcattccccatcatgtaggttgc-3' (SEQ ID NO: 57) | |
| CTLA-4 WT | F: 5'-ccatcacacaacactgatgaggtcc-3' (SEQ ID NO: 58) | WT: 478 bp |
| | R: 5'-cacatcccaaatgcgtttcattgc-3' (SEQ ID NO: 59) | |

TABLE 8

PCT reaction

| | |
|---|---|
| 2x Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| ddH$_2$O | Add to to 20 μL |

TABLE 9

PCR amplification reaction condition

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

As another example, double humanized TIM-3/PD-1 mice were generated. Since the mouse TIM-3 gene and PD-1 gene are located on different chromosomes, the double humanized TIM-3/PD-1 mice were obtained by mating B-hTIM-3 mice with humanized PD-1 mice (e.g. B-hPD-1, mice with humanized PD-1 gene). The progeny were screened and further mated to eventually obtain double humanized TIM-3/PD-1 mice.

Figures 15A, 15B, 15C, 15D:
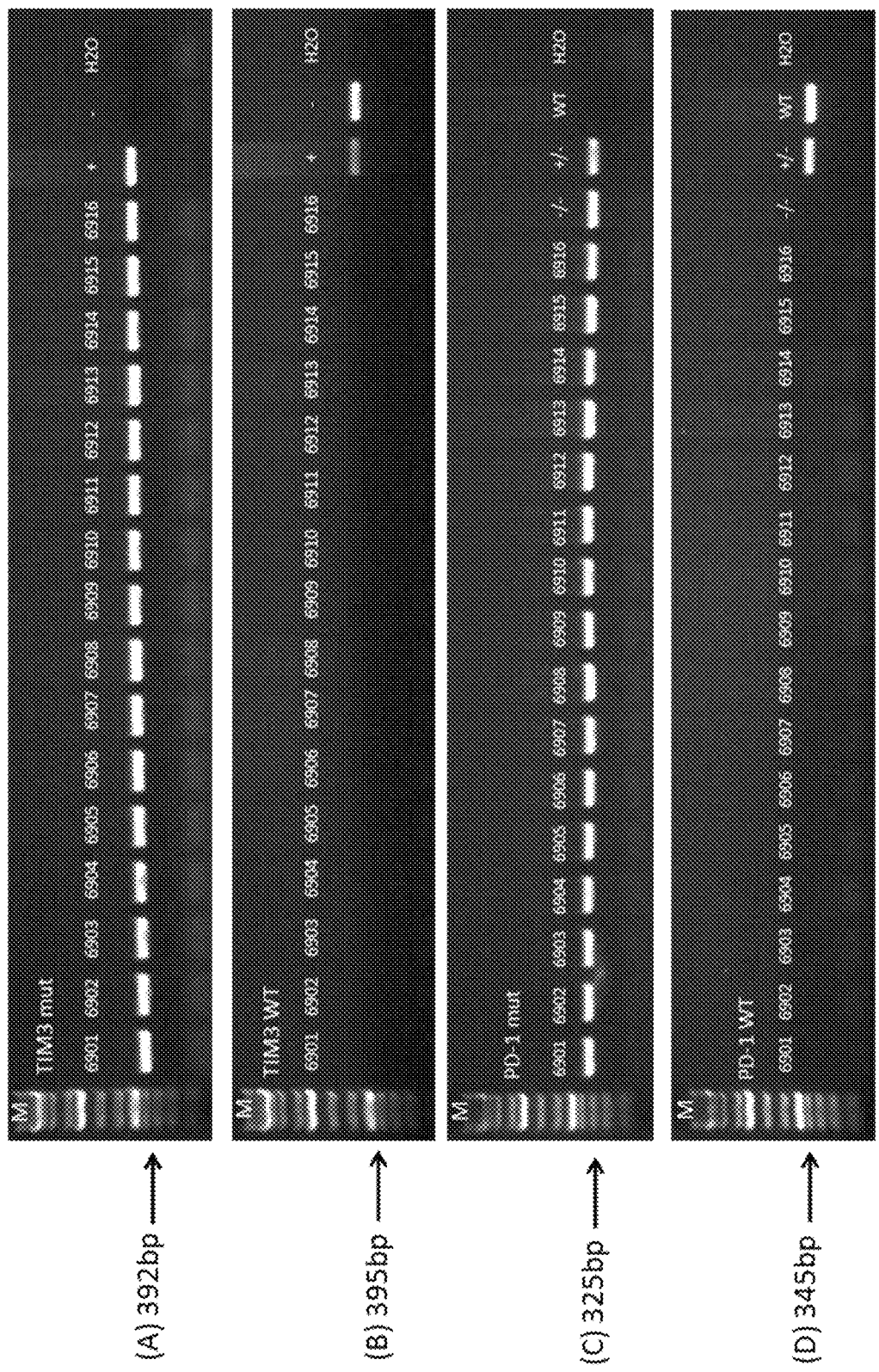
FIGS. 15A-15D. Mouse tail PCR identification results.
Figures 16A, 16B, 16C, 16D, 16E, 16F:
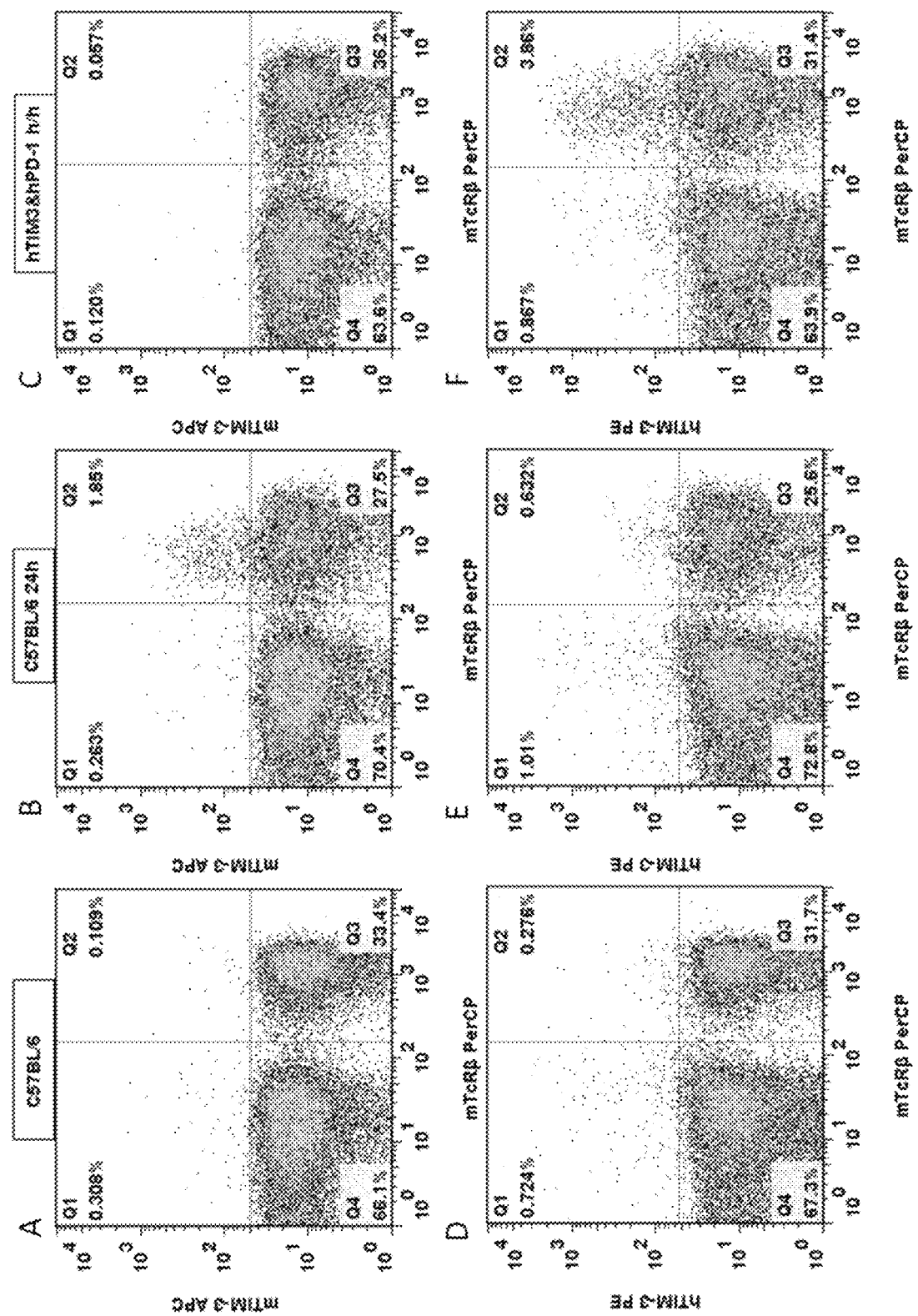
FIGS. 16A-16F show flow cytometry analysis results for C57BL/6 mice and double humanized TIM-3/PD-1 homozygous mice. Anti-mouse CD3 antibody was used to stimulate T cell activation in the spleens of the mice, and then the mouse TIM-3 antibody (mTIM-3 APC) and anti-mTCRβ antibody (mTcRβ PerCP) (FIGS. 17A, 17B, 17C), or anti-human TIM-3 antibody (hTIM-3 PE) and anti-mTCRβ antibody (mTcRβ PerCP) (FIGS. 17D, 17E, 17F), were used to label the cells. The results showed that the cells expressing humanized TIM-3 proteins were detected in the spleens of double humanized TIM-3/PD-1 mice, while no cell expressing humanized TIM-3 protein was detected in the spleen of C57BL/6 control mice.
Figures 17A, 17B, 17C, 17D, 17E, 17F:
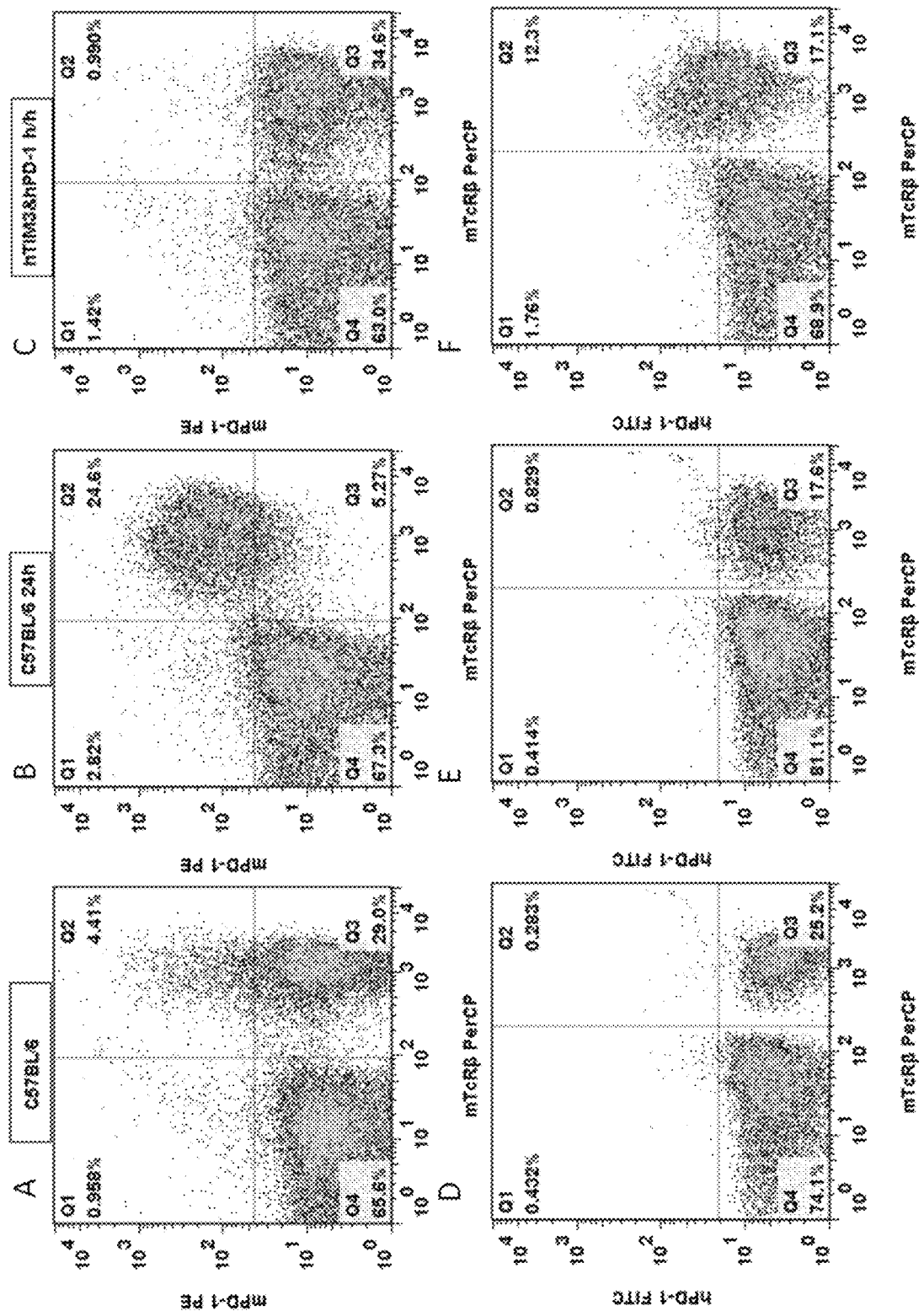
FIGS. 17A-17F show flow cytometry analysis results for C57BL/6 mice and double humanized TIM-3/PD-1 homozygous mice. Anti-mouse CD3 antibody was used to stimulate T cell activation in the spleens of the mice, and then anti-mouse PD-1 antibody (mPD-1 PE) and anti-mTcRβ antibody (mTcRβ PerCP) (FIGS. 17A, 17B, 17C), or anti-human PD-1 antibody (hPD-1 FITC) and anti-mTcRβ antibody (mTcRβ PerCP) (FIGS. 17D, 17E, 17F), were used to label the cells. The results showed that the cells expressing humanized PD-1 proteins were detected in the spleens of double humanized TIM-3/PD-1 mice, while no cell expressing humanized PD-1 protein was detected in the spleen of C57BL/6 control mice.

PCR analysis was performed on the mouse tail genomic DNA of double humanized TIM-3/PD-1 mice using four pairs of primers. The specific sequences and product lengths are shown in Table 10. The reaction system and reaction conditions are shown in Table 8 and Table 9. The results for a number of humanized TIM-3/PD-1 mice are shown in FIGS. 15A-15D, wherein FIGS. 15A and 15B show that the mice numbered 6901~6916 were homozygous for humanized TIM-3. FIGS. 15C and 15D show that the mice numbered 6901~6916 were homozygous for humanized PD-1. The combined results show that the mice numbered 6901~6916 were all homozygous for both humanized TIM-3 and humanized PD-1.

TABLE 10

Primer sequences

| Primer | Sequence | Product length |
|---|---|---|
| TIM-3 WT | F: 5'-gtgtttgaatgtggcaacgtggtgc-3' (SEQ ID NO: 54) | WT: 395 bp |
| | R: 5'-cacatgtggaagctataccactgca-3' (SEQ ID NO: 53) | |
| TIM-3 MUT | F: 5'-tggtcacagtgtaccaacgagttgc-3' (SEQ ID NO: 55) | Mut: 392 bp |
| | R: 5'-cacatgtggaagctataccactgca-3' (SEQ ID NO: 53) | |
| PD-1 MUT | F: 5'-cttccacatgagcgtggtcagggcc-3' (SEQ ID NO: 60) | Mut: 325 bp |
| | R: 5'-ccaagggactattttagatgggcag-3' (SEQ ID NO: 61) | |
| PD-1 WT | F: 5'-gaagctacaagctcctaggtaggggg-3' (SEQ ID NO: 62) | WT: 345 bp |

TABLE 10-continued

Primer sequences

| Primer | Sequence | Product length |
|---|---|---|
| | R: 5'-acgggttggctcaaaccattaca-3'<br>(SEQ ID NO: 63) | |

The expression of the double humanized TIM-3/PD-1 mice was further examined. A double humanized TIM-3/PD-1 homozygote (7 weeks old) was selected for the study. Two wildtype C57BL/6 mice were selected as controls. Mice were injected with 7.5 µg of mouse CD3 antibody intraperitoneally. After 24 hours, the mice were euthanized, and then the spleens of the mice were collected. The spleen samples were ground and the ground samples were filtered through a 70 µm cell mesh. The filtered cell suspensions were centrifuged and the supernatants were discarded; erythrocyte lysis solution was added for lysis for 5 min, and then PBS solution was added to neutralize the lysis reaction. The solution was centrifuged again and the supernatants were discarded, the cells were washed once with PBS. The obtained spleen cell samples were then subject to FACS and RT-PCR analysis.

FACS:

Expression of TIM-3 proteins in double humanized TIM-3/PD-1 mice was analyzed using the same methods as in Example 5. Briefly, the samples were stained with either 1) anti-mouse PD-1 antibody and anti-mTcRβ antibody; or 2) anti-human PD-1 antibody (hPD-1 FITC) and anti-mTcRβ antibody. The stained samples were washed in PBS and analyzed for PD-1 protein expression using Flow Cytometry. Results are shown in FIGS. 16A-16F, and FIGS. 17A-17F.

Cells expressing humanized TIM-3 and humanized PD-1 proteins were detected in the spleens of double humanized TIM-3/PD-1 homozygotes, using anti-human PD-1 antibody and anti-human TIM-3 antibody. No cell expressing humanized TIM-3 and humanized PD-1 was detected in the spleens of C57BL/6 mice either with CD3 antibody stimulation or without CD3 antibody stimulation.

RT-PCR Detection:

Total RNA was extracted from the spleen cells of wildtype C57BL/6 mice and double humanized TIM-3/PD-1 homozygotes. cDNA were then obtained by reverse transcription using a reverse transcription kit.

mTIM-3 RT-PCR F1 (SEQ ID NO: 48)
and mTIM-3 RT-PCR R1 (SEQ ID NO: 49) were used to
amplify a mouse TIM-3 fragment of 259 bp.

hTIM-3 RT-PCR F1 (SEQ ID NO: 50)
and hTIM-3 RT-PCR R1 (SEQ ID NO: 51) were used
amplify a humanized TIM-3 fragment of 164 bp.

mPD-1 RT-PCR primer F3:
5'-CCTGGCTCACAGTGTCAGAG-3',    (SEQ ID NO: 64)
and mPD-1 RT-PCR primer R3:
5'-CAGGGCTCTCCTCGATTTTT-3'    (SEQ ID NO: 65)
were used to amplify a mouse Pd-1 fragment of
approximately 297 bp.

hPD-1 RT-PCR primer F3:
5'-CCCTGCTCGTGGTGACCGAA-3',    (SEQ ID NO: 66)
and hPD-1 RT-PCR primer R3:
5'-GCAGGCTCTCTTTGATCTGC-3'    (SEQ ID NO: 67)
were used to amplify a human PD-1 fragment of
approximately 297 bp.

PCR reaction system was 20 µL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 18:
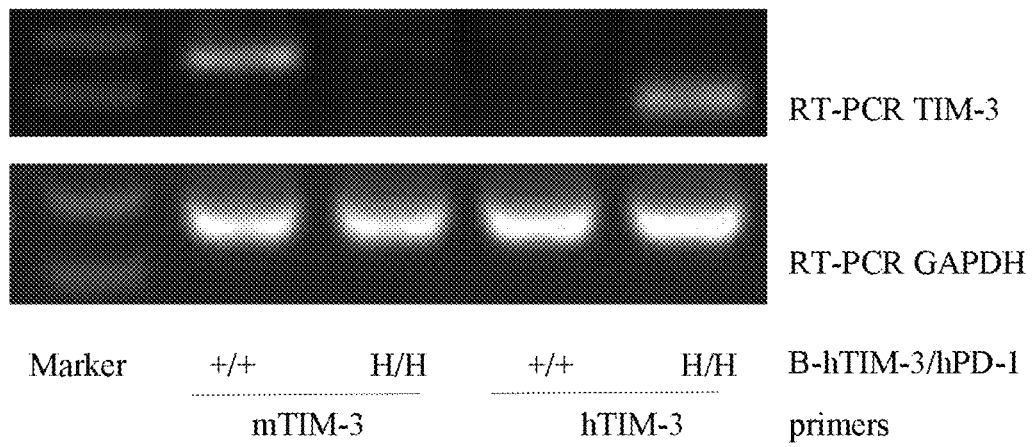
FIG. 18 shows RT-PCR detection results for mTIM-3 or humanized TIM-3 (hTIM-3), wherein +/+ is wildtype C57BL/6 mouse; H/H is double humanized TIM-3/PD-1 homozygous mice; and GAPDH is an internal control. mRNA of mouse TIM-3 was detected in activated T cells in C57BL/6 mice. mRNA of humanized TIM-3 was detected in activated T cells of double humanized TIM-3/PD-1 homozygous mice.
Figure 19:
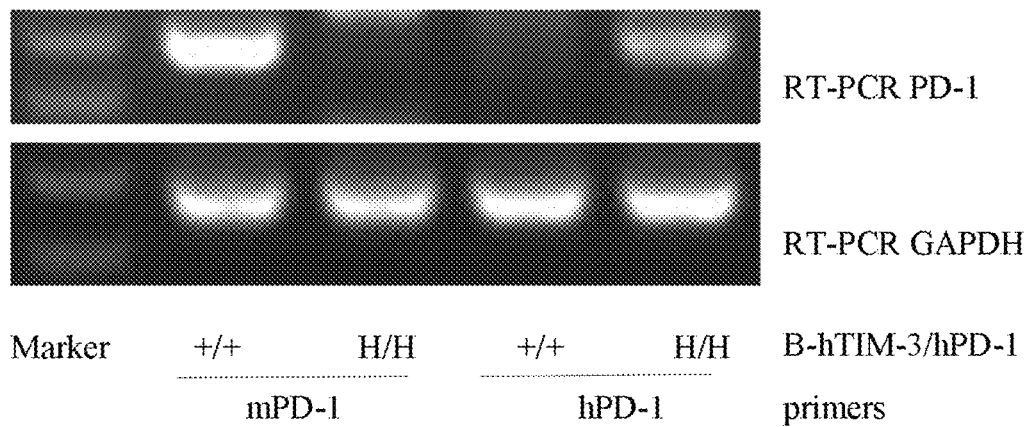
FIG. 19 shows RT-PCR detection results for mPD-1 or humanized PD-1 (hPD-1), wherein +/+ is wildtype C57BL/6 mouse; H/H is double humanized TIM-3/PD-1 homozygous mice; and GAPDH is an internal control. mRNA of mouse PD-1 was detected in activated T cells in C57BL/6 mice. mRNA of humanized PD-1 was detected in activated T cells of double humanized TIM-3/PD-1 homozygous mice.

The results are shown in FIG. 18 and FIG. 19. The mRNA of mouse TIM-3 and mouse PD-1 were detected in the activated cells of wildtype C57BL/6 mice; while the mRNA of humanized TIM-3 and humanized PD-1 were detected in the activated cells of double humanized TIM-3/PD-1 homozygotes.

Example 8. Pharmacological Validation of B-hTIM-3 Humanized Animal Model

B-hTIM-3 homozygous mice (4-8 weeks) were subcutaneously injected with mouse colon cancer cell MC38 ($5\times10^5$/100 µl PBS), and when the tumor volume grew to about 100 mm$^3$, the mice were divided to a control group and six treatment groups based on tumor size (n=5/group). The treatment groups were randomly selected for anti-human TIM-3 antibodies (Ab1, Ab2, Ab3) treatment (10 mg/kg); the control group was injected with an equal volume of blank solvent. The frequency of administration was twice a week (6 times of administrations in total). The tumor volume was measured twice a week and the body weight of the mice was weighed as well. Euthanasia was performed when the tumor volume of the mouse reached 3000 mm$^3$.

Figure 20:
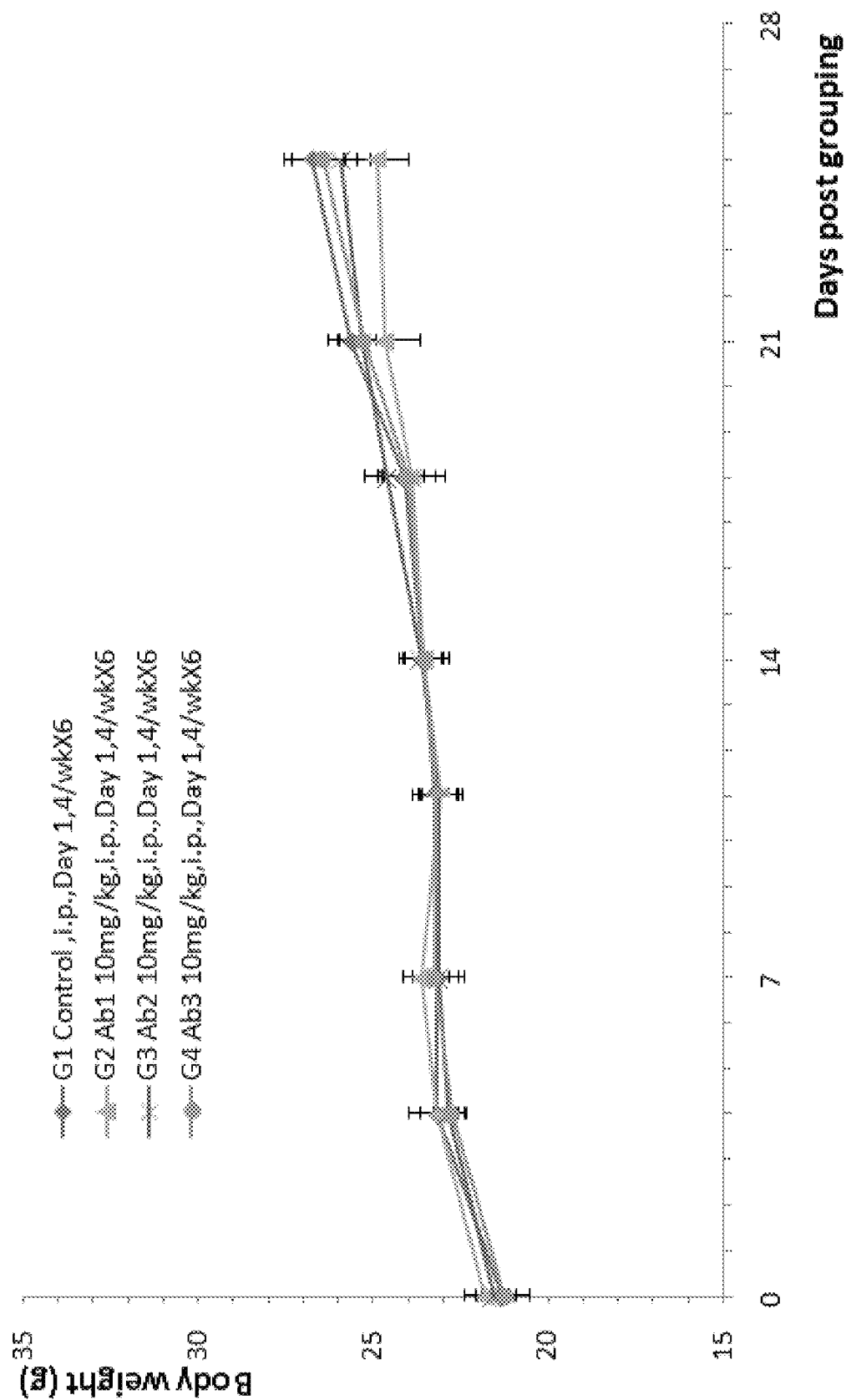
FIG. 20. Mouse colon cancer cells MC38 were injected into B-hTIM-3 mice and antitumor efficacy studies were performed with 3 anti-human TIM-3 antibodies (Ab1, Ab2, and Ab3, 10 mg/kg). There was no significant difference in the average weight between the G1 control group and the G2-G4 treatment groups.
Figure 21:
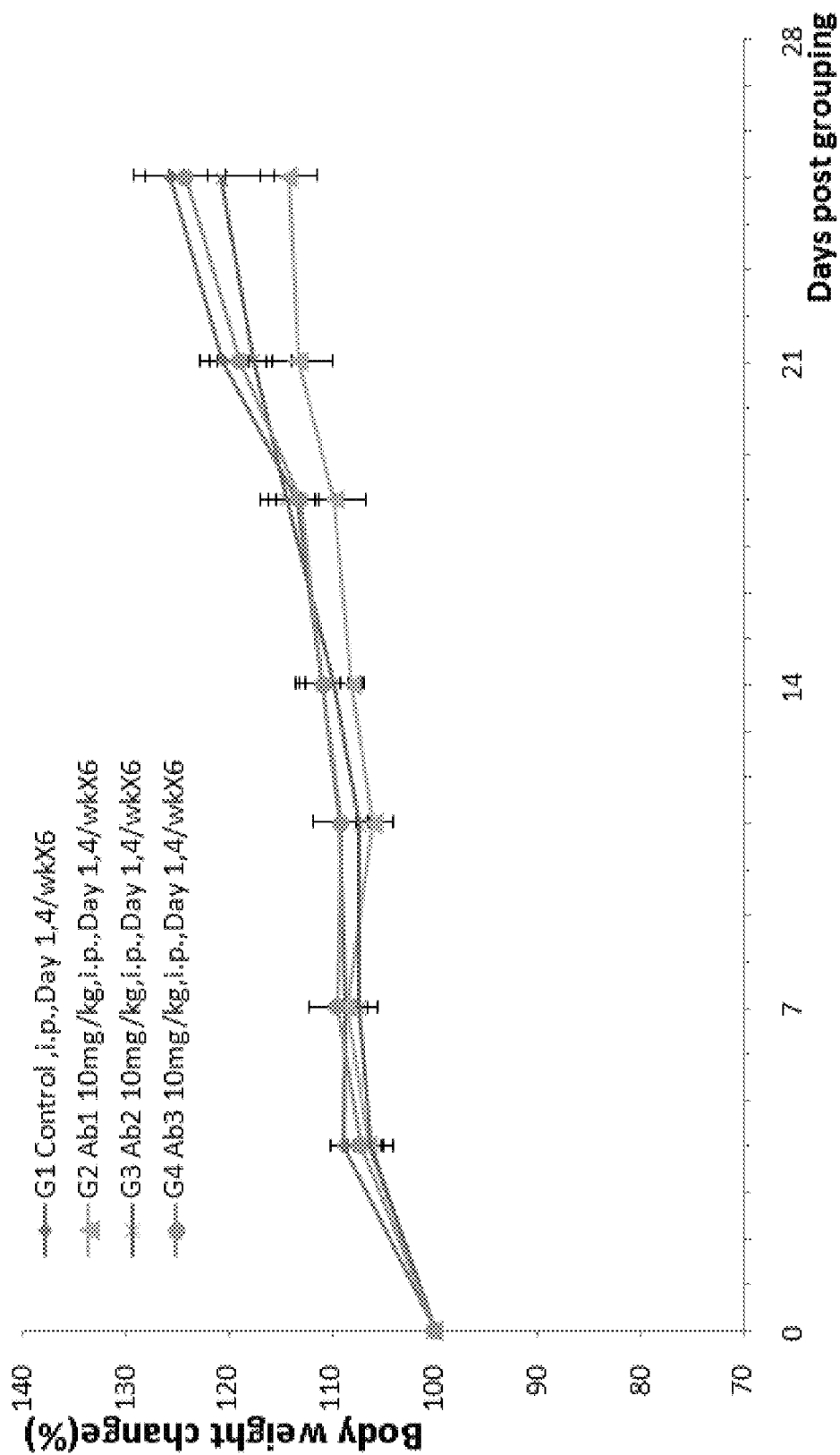
FIG. 21. Mouse colon cancer cells MC38 were injected into B-hTIM-3 mice and antitumor efficacy studies were performed with 3 anti-human TIM-3 antibodies (Ab1, Ab2, and Ab3, 10 mg/kg). There was no significant difference in the percentage of body weight change among the different groups.
Figure 22:
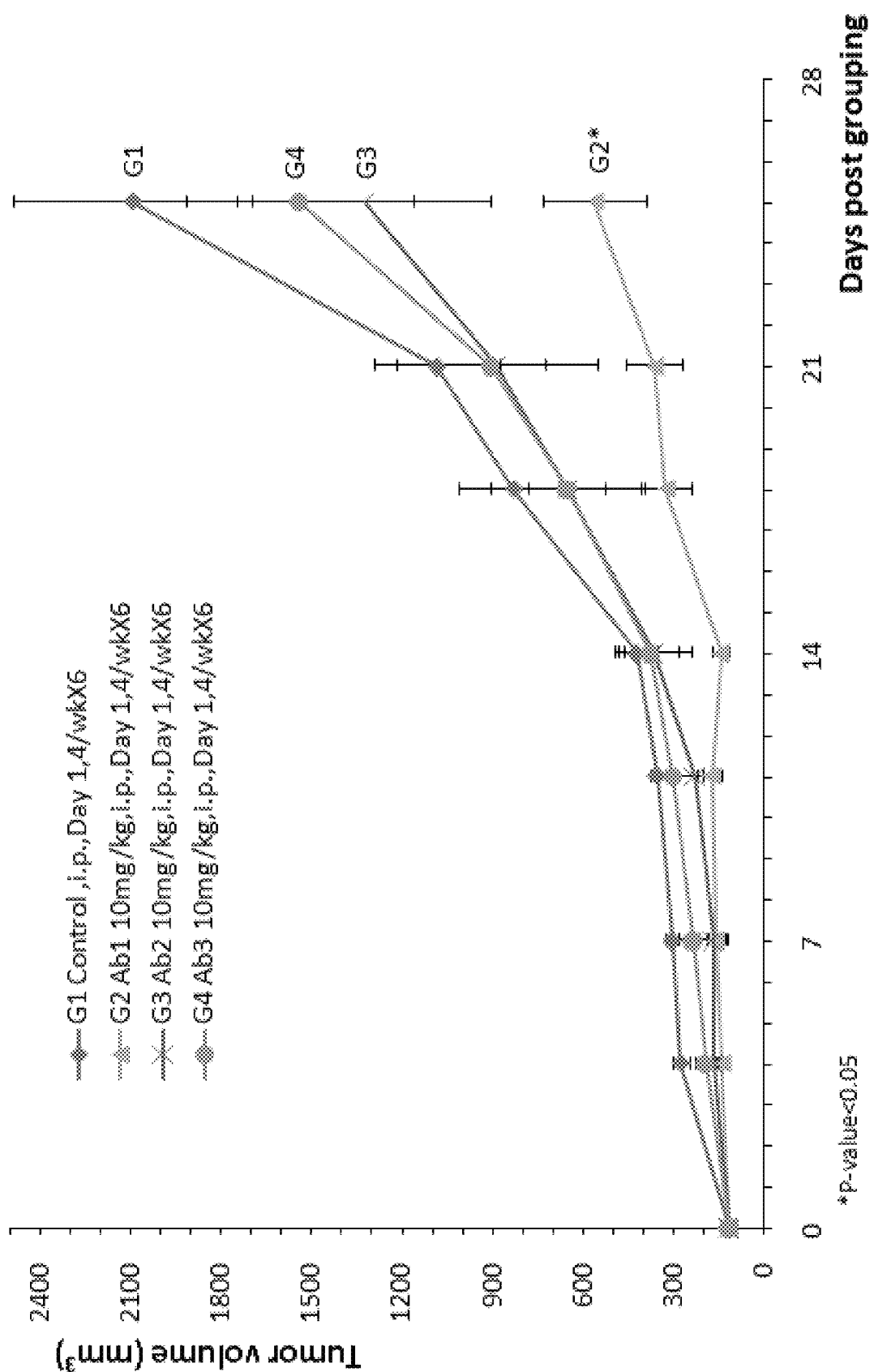
FIG. 22. Mouse colon cancer cells MC38 were injected into B-hTIM-3 mice and antitumor efficacy studies were performed with 3 anti-human TIM-3 antibodies (Ab1, Ab2, Ab3, 10 mg/kg). The average volumes of tumors in the G2-G4 treatment groups were smaller than the G1 control group, and the differences were significant.

Overall, the animals in each group were healthy, and the body weights of all the treatment and control group mice increased, and were not significantly different from each other (FIG. 20 and FIG. 21). The tumor in the control group continued growing during the experimental period; when compared with the control group mice, the tumor volumes in the treatment groups were smaller than the control group (FIG. 22). The results indicated that the use of anti-human TIM-3 antibodies (Ab1, Ab2, and Ab3) were well tolerated without causing toxic effects, and inhibited tumor growth in mice.

Table 11 shows results for this experiment, including the tumor volumes at the day of grouping (day 0), 18 days after the grouping (day 18), and at the end of the experiment (day 25), the survival rate of the mice, the number of tumor-free mice (non-existence of tumor), the Tumor Growth Inhibition value ($TGI_{TV}$), and the statistical differences (P value) in mouse body weights and tumor volume between the treatment and control groups.

TABLE 11

| | | Tumor volume (mm³) | | | Non- | | P value | |
|---|---|---|---|---|---|---|---|---|
| | | Day 0 | Day 18 | Day 25 | Survival | existence of tumor | $TGI_{TV}$% | Body weight | Tumor Volume |
| Control | G1 | 118 ± 7 | 831 ± 186 | 2096 ± 396 | 5/5 | 0/5 | N/A | N/A | N/A |
| Treatment | G2 (Ab1) | 118 ± 7 | 327 ± 85 | 563 ± 168 | 5/5 | 0/5 | 77.5 | 0.183 | 0.007 |
| | G3 (Ab2) | 118 ± 11 | 654 ± 254 | 1326 ± 420 | 5/5 | 0/5 | 38.9 | 0.529 | 0.219 |
| | G4 (Ab3) | 118 ± 12 | 665 ± 127 | 1540 ± 376 | 5/5 | 0/5 | 28.1 | 0.820 | 0.339 |

At the end of the experiment (day 25), the body weight of each group increased and there was no significant difference between the groups (p>0.05), indicating that the animals well tolerated the three anti-hTIM-3 antibodies. With respect to the tumor volume, in the control group (G1), the average tumor volume was 2096±885 mm³.

The tumor volumes in the treatment groups were 563±168 mm³ (G2), 1326±420 mm³ (G3), and 1540±376 mm³ (G4). The tumor volumes in the treatment groups G2-G4 were significantly smaller than the control group G1, with $TGI_{TV}$ values of 77.5% (G2), 38.9% (G3), and 28.1% (G4). The results show that anti-human TIM-3 antibodies Ab1, Ab2, and Ab3 had different tumor inhibitory effects in B-hTIM-3 mice, with Ab1 (G2) showing significant tumor inhibition ($TGI_{TV}$>60%), better than those of Ab2 (G3) and Ab3 (G4). All three antibodies were well tolerated with no obvious toxic effects.

The results above have demonstrated that the humanized TIM-3 mouse model (B-hTIM-3) can be used as an in vivo animal model for investigating in vivo efficacy and toxicity of potential anti-cancer drugs. The humanized TIM-3 mouse model can also be used to screen for potential modulators of the TIM-3 signaling pathway, to evaluate the efficacy and toxicity of these modulators, and to design treatment regimens using these modulators. The humanized TIM-3 mouse model can additionally be used to evaluate and predict the efficacy and toxicity of anti-human TIM-3 antibodies, and the potential treatment results of drug candidates targeting human TIM-3.

Example 9. Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 23:
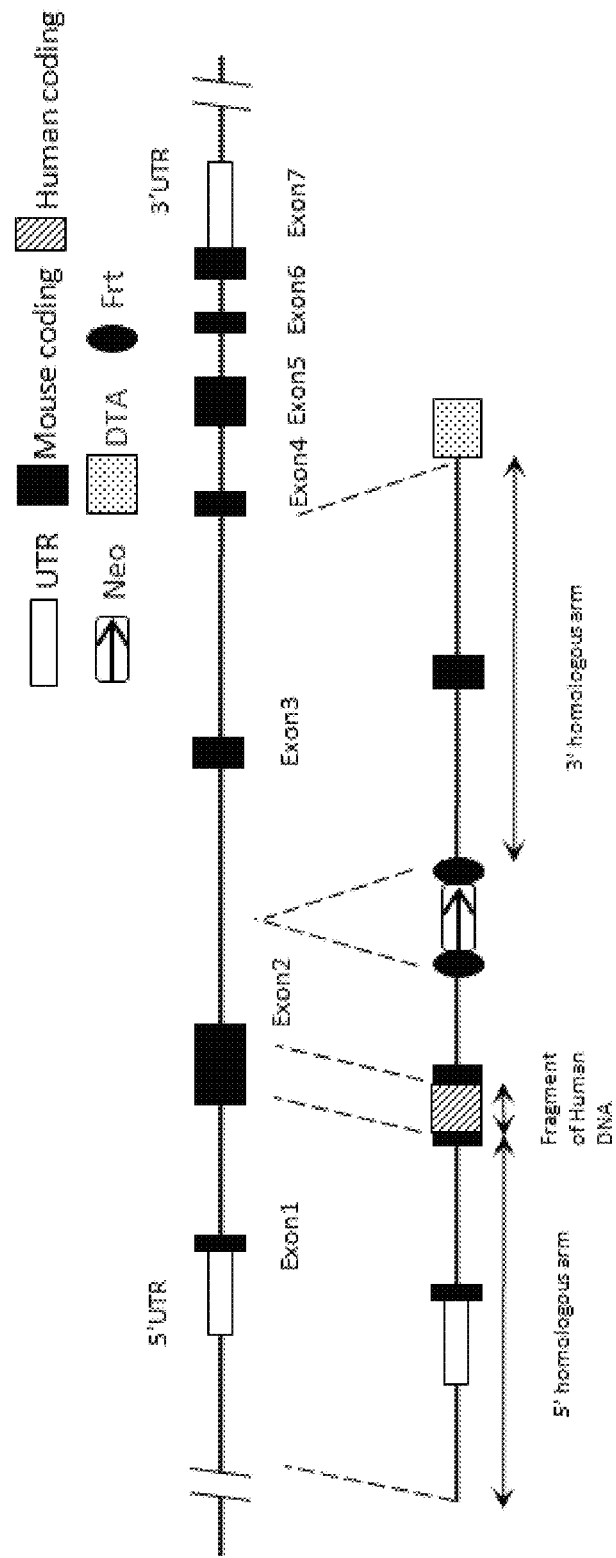
FIG. 23 is a schematic diagram of the targeting strategy for embryonic stem cells.

In this example, the conventional ES cell gene homologous recombination technique is used as an example to describe how to obtain TIM-3 gene humanized mice by other methods. Based on the humanized mouse TIM-3 gene map (FIG. 3B), a gene editing strategy and methods are shown in FIG. 23, which also shows the design of the recombinant vector. Since objective is to replace exon 2 of the mouse TIM-3 gene in whole or in part with the corresponding human TIM-3 gene fragment, a recombinant vector that contains a 5' homologous arm (3122 bp), a 3' homologous arm (5000 bp) and a humanized gene fragment (321 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the TIM-3 gene humanized homozygous mice can be obtained by mating these mice with each other. The methods of genotyping and phenotypic detection of the obtained F1 heterozygous mice or F2 homozygous mice are similar to those used in Example 5 described above.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mammal whose genome comprises a chimeric TIM-3 gene at an endogenous TIM-3 locus, wherein the chimeric TIM-3 gene comprises a nucleic acid encoding a portion of an extracellular domain of a human TIM-3 protein in place of a nucleic acid encoding a corresponding portion of an extracellular domain of an endogenous TIM-3 protein, wherein the chimeric TIM-3 gene is operably linked to an endogenous TIM-3 promoter, wherein the mammal expresses a chimeric TIM-3 protein encoded by the chimeric TIM-3 gene, wherein the mammal is a mouse, a rat, or a non-human primate.

2. The mammal of claim 1, wherein the mammal is a mouse and the chimeric TIM-3 gene comprises a sequence that encodes an amino acid sequence that is at least 95% identical to SEQ ID NO:30.

3. The mammal of claim 1, wherein the chimeric TIM-3 gene comprises a sequence that encodes amino acids 22-128 of SEQ ID NO:26.

4. The mammal of claim 1, wherein the mammal is a non-human primate.

5. The mammal of claim 1, wherein the mammal is a mouse.

6. The mammal of claim 1, wherein the mammal does not express endogenous TIM-3.

7. The mammal of claim 1, wherein the mammal is homozygous with respect to the chimeric TIM-3 gene.

8. The mammal of claim 1, wherein the mammal further comprises a sequence encoding an additional human or chimeric protein.

9. The mammal of claim 8, wherein the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), TNF Receptor Superfamily Member 9 (4-1BB), CD27, CD28, CD47, T-Cell Immunoreceptor With Ig And ITIM Domains (TIGIT), CD27, Glucocorticoid-Induced TNFR-Related Protein (GITR), or TNF Receptor Superfamily Member 4 (OX40).

10. The mammal of claim 1, wherein the portion of the extracellular region of the human TIM-3 protein comprises at least 50 amino acid residues of the extracellular region of the human TIM-3 protein.

11. The mammal of claim 1, wherein the portion of the extracellular region of the human TIM-3 protein comprises at least 80 amino acid residues of the extracellular region of the human TIM-3 protein.

12. The mammal of claim 1, wherein the chimeric TIM-3 gene comprises a nucleic acid encoding the entire extracellular domain of the human TIM-3 protein in place of a nucleic acid encoding the entire extracellular domain of the endogenous TIM-3 protein.

13. The mammal of claim 1, wherein the chimeric TIM-3 gene comprises a sequence that encodes an amino acid sequence that is identical to SEQ ID NO: 30.

14. A genetically-modified, non-human mammal whose genome comprises a nucleic acid sequence encoding a chimeric TIM-3 protein at an endogenous TIM-3 gene locus, wherein the chimeric TIM-3 protein comprises a humanized TIM-3 extracellular region and an endogenous TIM-3 cytoplasmic region, and the nucleic acid sequence encoding the chimeric TIM-3 protein is operably linked to an endogenous TIM-3 promoter, wherein the mammal expresses the chimeric TIM-3 protein, and wherein the mammal is a mouse, rat, or non-human primate.

15. The mammal of claim 14, wherein the humanized TIM-3 extracellular region comprises at least 50 amino acid residues of the extracellular region of the human TIM-3 protein.

16. The mammal of claim 14, wherein the nucleic acid sequence encodes an amino acid sequence that is at least 95% identical to SEQ ID NO: 30.

17. The mammal of claim 14, wherein the mammal is a mouse.

18. The mammal of claim 14, wherein the humanized TIM-3 extracellular region comprises at least 80 amino acid residues of the extracellular region of the human TIM-3 protein.

19. The mammal of claim 14, wherein the mammal is a rat.

20. The mammal of claim 14, wherein the mammal does not express endogenous TIM-3.

* * * * *

SEQUENCE LISTING

<160> NUMBER OF SEQ ID NOS: 67

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1
tccttacttt atagggtcat tgg                                          23

<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2
agtgtaactg cagggcagat agg                                          23

<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3
ggaaaatgct tatgtgtttg agg                                          23

<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4
tgtagataga gtgtaactgc agg                                          23

<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5
gttacactct atctacacct ggg                                          23

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
cacataggca caagtgcccc agg                                          23

<210> SEQ ID NO 7
<211> LENGTH: 23
<212> TYPE: DNA
<213> ORGANISM: Artificial

```
<220> FEATURE:
<223> OTHER INFORMATION: sgRNA target sequence

<400> SEQUENCE: 7
ctgaaattag acatcaaagc agg                                              23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
atgtgactct ggatgaccat ggg                                              23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
gatcataaag aatgtgactc tgg                                              23

<210> SEQ ID NO 10
<211> LENGTH: 23
<212> TYPE: DNA
<213> ORGANISM: Artificial
<220> FEATURE:
<223> OTHER INFORMATION: sgRNA target sequence

<400> SEQUENCE: 10
tccagcagat accagctaaa ggg                                              23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
ctaaagggcg atctcaacaa agg                                              23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
tgttgagatc gccctttagc tgg                                              23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
gccctttagc tggtatctgc tgg                                              23
```

```
<210> SEQ ID NO 14
<211> LENGTH: 18
<212> TYPE: DNA
<213> ORGANISM: Artificial
<220> FEATURE:
<223> OTHER INFORMATION: sgRNA target sequence

<400> SEQUENCE: 14
aaaatgctta tgtgtttg                                                       18

<210> SEQ ID NO 15
<211> LENGTH: 22
<212> TYPE: DNA
<213> ORGANISM: Artificial
<220> FEATURE:
<223> OTHER INFORMATION: sgRNA target sequence

<400> SEQUENCE: 15
taggaaaatg cttatgtgtt tg                                                  22

<210> SEQ ID NO 16
<211> LENGTH: 18
<212> TYPE: DNA
<213> ORGANISM: Artificial
<220> FEATURE:
<223> OTHER INFORMATION: sgRNA target sequence

<400> SEQUENCE: 16
caaacacata agcatttt                                                       18

<210> SEQ ID NO 17
<211> LENGTH: 22
<212> TYPE: DNA
<213> ORGANISM: Artificial
<220> FEATURE:
<223> OTHER INFORMATION: sgRNA target sequence

<400> SEQUENCE: 17
aaaccaaaca cataagcatt tt                                                  22

<210> SEQ ID NO 18
<211> LENGTH: 17
<212> TYPE: DNA
<213> ORGANISM: Artificial
<220> FEATURE:
<223> OTHER INFORMATION: sgRNA target sequence

<400> SEQUENCE: 18
tgactctgga tgaccat                                                        17

<210> SEQ ID NO 19
<211> LENGTH: 21
<212> TYPE: DNA
<213> ORGANISM: Artificial
<220> FEATURE:
<223> OTHER INFORMATION: sgRNA target sequence

<400> SEQUENCE: 19
taggtgactc tggatgacca t                                                   21

<210> SEQ ID NO 20
<211> LENGTH: 17
<212> TYPE: DNA
<213> ORGANISM: Artificial
<220> FEATURE:
<223> OTHER INFORMATION: sgRNA target sequence
```

```
<400> SEQUENCE: 20
atggtcatcc agagtca                                                    17

<210> SEQ ID NO 21
<211> LENGTH: 21
<212> TYPE: DNA
<213> ORGANISM: Artificial
<220> FEATURE:
<223> OTHER INFORMATION: sgRNA target sequence

<400> SEQUENCE: 21
aaacatggtc atccagagtc a                                               21

<210> SEQ ID NO 22
<211> LENGTH: 132
<212> TYPE: DNA
<213> ORGANISM: Artificial
<220> FEATURE:
<223> OTHER INFORMATION: sgRNA target sequence

<400> SEQUENCE: 22
gaattctaat acgactcact ataggggtc ttcgagaaga cctgttttag agctagaaat      60
agcaagttaa aataaggcta gtccgttatc aacttgaaaa agtggcaccg agtcggtgct    120
tttaaaggat cc                                                        132

<210> SEQ ID NO 23
<211> LENGTH: 2725
<212> TYPE: DNA
<213> ORGANISM: Mus musculus

<400> SEQUENCE: 23
accattttaa ccgaggagct aaagctatcc ctacacagag ctgtccttgg atttcccctg     60
ccaagtactc atgttttcag gtcttaccct caactgtgtc ctgctgctgc tgcaactact   120
acttgcaagg tcattggaaa atgcttatgt gtttgaggtt ggtaagaatg cctatctgcc   180
ctgcagttac actctatcta cacctggggc acttgtgcct atgtgctggg gcaagggatt   240
ctgtccttgg tcacagtgta ccaacgagtt gctcagaact gatgaaagaa atgtgacata   300
tcagaaatcc agcagatacc agctaaaggg cgatctcaac aaaggagacg tgtctctgat   360
cataaagaat gtgactctgg atgaccatgg gacctactgc tgcaggatac agttccctgg   420
tcttatgaat gataaaaaat tagaactgaa attagacatc aaagcagcca aggtcactcc   480
agctcagact gccatggggg actctactac agcttctcca agaaccctaa ccacggagag   540
aaatggttca gagacacaga cactggtgac cctccataat aacaatggaa caaaaatttc   600
cacatgggct gatgaaatta aggactctgg agaaacgatc agaactgcta tccacattgg   660
agtgggagtc tctgctgggt tgaccctggc acttatcatt ggtgtcttaa tccttaaatg   720
gtattcctgt aagaaaaaga agttatcgag tttgagcctt attacactgg ccaacttgcc   780
tccaggaggg ttggcaaatg caggagcagt caggattcgc tctgaggaaa atatctacac   840
catcgaggag aacgtatatg aagtggagaa ttcaaatgag tactactgct acgtcaacag   900
ccagcagcca tcctgaccgc ctctggactg ccactttaa aggctcgcct tcatttctga    960
ctttggtatt tcccttttg aaaactatgt gatatgtcac ttggcaacct cattggaggt   1020
tctgaccaca gccactgaga aaagagttcc agttttctgg ggataattaa ctcacaaggg   1080
gattcgactg taactcatgc tacattgaaa tgctccattt tatccctgag tttcagggat   1140
```

```
cggatctccc actccagaga cttcaatcat gcgtgttgaa gctcactcgt gctttcatac    1200
attaggaatg gttagtgtga tgtctttgag acatagaggt ttgtggtata tctgcaaagc    1260
tcctgaacag gtaggggaa taaagggcta agataggaag gtgaggttct tgttgatgt      1320 tgaaaatcta agaagttgg tagcttttct agagatttct gaccttgaaa gattaagaaa     1380
aagccaggtg gcatatgctt aacactatat aacttgggaa ccttaggcag gagggtgata   1440
agttcaaggt cagccagggc tatgctggta agactgtctc aaaatccaaa gacgaaaata   1500
aacatagaga cagcaggagg ctggagatga ggctcggaca gtgaggtgca ttttgtacaa   1560
gcacgaggaa tctatatttg atcgtagacc ccacatgaaa aagctaggcc tggtagagca   1620
tgcttgtaga ctcaagagat ggagaggtaa aggcacaaca gatccccggg gcttgcgtgc   1680
agtcagctta gcctaggtgc tgagttccaa gtccacaaga gtccctgtct caaagtaaga   1740
tggactgagt atctggcgaa tgtccatggg ggttgtcctc tgctctcaga agagacatgc   1800
acatgaacct gcacacacac acacacacac acacacacac acacacacac acacacacac   1860
acacacatga aatgaaggtt ctctctgtgc ctgctaccct tctataacat gtatctctac    1920
aggactctcc tctgcctctg ttaagacatg agtgggagca tggcagagca gtccagtaat   1980
taattccagc actcagaagg ctggagcaga agcgtggaga gttcaggagc actgtgccca   2040
acactgccag actcttctta cagaagaaaa aggttacccg caagcagcct gctgtctgta    2100
aaaggaaacc ctgcgaaagg caaactttga ctgttgtgtg ctcaagggga actgactcag   2160
acaacttctc cattcctgga ggaaactgga gctgtttctg acagaagaac aaccggtgac   2220
tgggacatac gaaggcagag ctcttgcagc aatctatata gtcagcaaaa tattctttgg   2280
gaggacagtc gtcaccaaat tgatttccaa gccggtggac ctcagtttca tctggcttac   2340
agctgcctgc ccagtgccct tgatctgtgc tggctcccat ctataacaga atcaaattaa   2400
atagaccccg agtgaaaata ttaagtgagc agaaaggtag cttttgttcaa agatttttt   2460 gcattgggga gcaactgtgt acatcagagg acatctgtta gtgaggacac caaaacctgt   2520
ggtaccgttt tttcatgtat gaattttgtt gtttaggttg cttctagcta gctgtggagg   2580
tcctggcttt cttaggtggg tatggaaggg agaccatcta acaaaatcca ttagagataa   2640
cagctctcat gcagaaggga aaactaatct caaatgtttt aaagtaataa aactgtactg   2700
gcaaagtact ttgagcatat ttaaa                                         2725
```

<210> SEQ ID NO 24
<211> LENGTH: 281
<212> TYPE: PRT
<213> ORGANISM: Mus musculus

<400> SEQUENCE: 24

Met Phe Ser Gly Leu Thr Leu Asn Cys Val Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
            115                 120                 125

Asp Ile Lys Ala Ala Lys Val Thr Pro Ala Gln Thr Ala His Gly Asp
        130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
            195                 200                 205

Ile Ile Gly Val Leu Ile Leu Lys Trp Tyr Ser Cys Lys Lys Lys Lys
            210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
            275                 280

<210> SEQ ID NO 25
<211> LENGTH: 2448
<212> TYPE: DNA
<213> ORGANISM: Homo sapiens

<400> SEQUENCE: 25
agaacactta caggatgtgt gtagtgtggc atgacagaga actttggttt cctttaatgt      60
gactgtagac ctggcagtgt tactataaga atcactggca atcagacacc cgggtgtgct    120
gagctagcac tcagtggggg cggctactgc tcatgtgatt gtggagtaga cagttggaag    180
aagtacccag tccatttgga gagttaaaac tgtgcctaac agaggtgtcc tctgactttt    240
cttctgcaag ctccatgttt tcacatcttc cctttgactg tgtcctgctg ctgctgctgc    300
tactacttac aaggtcctca gaagtggaat acagagcgga ggtcggtcag aatgcctatc    360
tgccctgctt ctacccccag ccgcccccag gaacctcgt gcccgtctgc tggggcaaag    420
gagcctgtcc tgtgtttgaa tgtggcaacg tggtgctcag gactgatgaa agggatgtga    480
attattggac atccagatac tggctaaatg gggatttccg caaggagat gtgtccctga    540 ccatagagaa tgtgactcta gcagacagtg ggatctactg ctgccggatc caaatcccag    600
gcataatgaa tgatgaaaaa tttaacctga agttggtcat caaaccagcc aaggtcaccc    660
ctgcaccgac tcggcagaga gacttcactg cagcctttcc aaggatgctt accaccaggg    720
gacatggccc agcagagaca cagacactgg ggagcctccc tgatataaat ctaacacaaa    780
tatccacatt ggccaatgag ttacgggact ctagattggc caatgactta cgggactctg    840
gagcaaccat cagaataggc atctacatcg gagcagggat ctgtgctggg ctggctctgg    900
ctcttatctt cggcgcttta attttcaaat ggtattctca tagcaaagag aagatacaga    960
atttaagcct catctctttg gccaacctcc ctccctcagg attggcaaat gcagtagcag   1020

| | | | |
|---|---|---|---|
| agggaattcg ctcagaagaa aacatctata ccattgaaga gaacgtatat gaagtggagg | 1080 |
| agcccaatga gtattattgc tatgtcagca gcaggcagca accctcacaa cctttgggtt | 1140 |
| gtcgctttgc aatgccatag atccaaccac cttattttg agcttggtgt tttgtctttt | 1200 |
| tcagaaacta tgagctgtgt cacctgactg gttttggagg ttctgtccac tgctatggag | 1260 |
| cagagttttc ccattttcag aagataatga ctcacatggg aattgaactg ggacctgcac | 1320 |
| tgaacttaaa caggcatgtc attgcctctg tatttaagcc aacagagtta cccaacccag | 1380 |
| agactgttaa tcatggatgt tagagctcaa acgggctttt atatacacta ggaattcttg | 1440 |
| acgtggggtc tctggagctc caggaaattc gggcacatca tatgtccatg aaacttcaga | 1500 |
| taaactaggg aaaactgggt gctgaggtga agcataact ttttggcac agaaagtcta | 1560 |
| aaggggccac tgattttcaa agagatctgt gatcccttt tgtttttgt ttttgagatg | 1620 |
| gagtcttgct ctgttgccca ggctggagtg caatggcaca atctcggctc actgcaagct | 1680 |
| ccgcctcctg ggttcaagcg attctcctgc ctcagcctcc tgagtggctg ggattacagg | 1740 |
| catgcaccac catgcccagc taatttgttg tattttagt agagacaggg tttcaccatg | 1800 |
| ttggccagtg tggtctcaaa ctcctgacct catgatttgc ctgcctcggc ctcccaaagc | 1860 |
| actgggatta caggcgtgag ccaccacatc cagccagtga tccttaaaag attaagagat | 1920 |
| gactggacca ggtctacctt gatcttgaag attcccttgg aatgttgaga tttaggctta | 1980 |
| tttgagcact gcctgcccaa ctgtcagtgc cagtgcatag cccttctttt gtctcccta | 2040 |
| tgaagactgc cctgcagggc tgagatgtgg caggagctcc cagggaaaaa cgaagtgcat | 2100 |
| ttgattggtg tgtattggcc aagttttgct tgttgtgtgc ttgaaagaaa atatctctga | 2160 |
| ccaacttctg tattcgtgga ccaaactgaa gctatatttt tcacagaaga gaagcagtg | 2220 |
| acggggacac aaattctgtt gcctggtgga agaaggcaa aggccttcag caatctatat | 2280 |
| taccagcgct ggatccttg acagagagtg gtccctaaac ttaaatttca agacggtata | 2340 |
| ggcttgatct gtcttgctta tgttgcccc ctgcgcctag cacaattctg acacacaatt | 2400 |
| ggaacttact aaaaattttt ttttactgtt aaaaaaaaaa aaaaaaa | 2448 |

<210> SEQ ID NO 26
<211> LENGTH: 301
<212> TYPE: PRT
<213> ORGANISM: Homo sapiens

<400> SEQUENCE: 26

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

```
Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
                260                 265                 270

Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
290                 295                 300
```

<210> SEQ ID NO 27
<211> LENGTH: 342
<212> TYPE: DNA
<213> ORGANISM: Artificial
<220> FEATURE:
<223> OTHER INFORMATION: Mouse human chimeric sequence

<400> SEQUENCE: 27

```
ttatagggtc atcagaagtg aatacagag cggaggtcgg tcagaatgcc tatctgccct      60
gcttctacac cccagccgcc ccagggaacc tcgtgcccgt ctgctggggc aaaggagcct    120
gtcctgtgtt tgaatgtggc aacgtggtgc tcaggactga tgaaagggat gtgaattatt    180
ggacatccag atactggcta atggggatt ccgcaaagg agatgtgtcc ctgaccatag      240
agaatgtgac tctagcagac agtgggatct actgctgccg gatccaaatc ccaggcataa    300
tgaatgatga aaaatttaac ctgaagttgg tcatcaaagc ag                       342
```

<210> SEQ ID NO 28
<211> LENGTH: 843
<212> TYPE: DNA
<213> ORGANISM: Artificial
<220> FEATURE:
<223> OTHER INFORMATION: Mouse human chimeric sequence

<400> SEQUENCE: 28

```
atgttttcag gtcttaccct caactgtgtc ctgctgctgc tgcaactact acttgcaagg     60
tcatcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa gcagccaagg tcactccagc tcagactgcc    420
```

```
catggggact ctactacagc ttctccaaga accctaacca cggagagaaa tggttcagag    480
acacagacac tggtgaccct ccataataac aatggaacaa aaatttccac atgggctgat    540
gaaattaagg actctggaga aacgatcaga actgctatcc acattggagt gggagtctct    600
gctgggttga ccctggcact tatcattggt gtcttaatcc ttaaatggta ttcctgtaag    660
aaaaagaagt tatcgagttt gagccttatt acactggcca acttgcctcc aggagggttg    720
gcaaatgcag gagcagtcag gattcgctct gaggaaaata tctacaccat cgaggagaac    780
gtatatgaag tggagaattc aaatgagtac tactgctacg tcaacagcca gcagccatcc    840
tga                                                                  843
```

<210> SEQ ID NO 29
<211> LENGTH: 2722
<212> TYPE: DNA
<213> ORGANISM: Artificial
<220> FEATURE:
<223> OTHER INFORMATION: Mouse human chimeric sequence
<400> SEQUENCE: 29

```
accattttaa ccgaggagct aaagctatcc ctacacagag ctgtccttgg atttcccctg     60
ccaagtactc atgttttcag gtcttaccct caactgtgtc ctgctgctgc tgcaactact    120
acttgcaagg tcatcagaag tggaatacag agcggaggtc ggtcagaatg cctatctgcc    180
ctgcttctac accccagccg ccccagggaa cctcgtgccc gtctgctggg gcaaaggagc    240
ctgtcctgtg tttgaatgtg caacgtggt gctcaggact gatgaaaggg atgtgaatta    300
ttggacatcc agatactggc taaatgggga tttccgcaaa ggagatgtgt ccctgaccat    360
agagaatgtg actctagcag acagtgggat ctactgctgc cggatccaaa tcccaggcat    420
aatgaatgat gaaaaattta acctgaagtt ggtcatcaaa gcagccaagg tcactccagc    480
tcagactgcc catggggact ctactacagc ttctccaaga accctaacca cggagagaaa    540
tggttcagag acacagacac tggtgaccct ccataataac aatggaacaa aaatttccac    600
atgggctgat gaaattaagg actctggaga aacgatcaga actgctatcc acattggagt    660
gggagtctct gctgggttga ccctggcact tatcattggt gtcttaatcc ttaaatggta    720
ttcctgtaag aaaaagaagt tatcgagttt gagccttatt acactggcca acttgcctcc    780
aggagggttg gcaaatgcag gagcagtcag gattcgctct gaggaaaata tctacaccat    840
cgaggagaac gtatatgaag tggagaattc aaatgagtac tactgctacg tcaacagcca    900
gcagccatcc tgaccgcctc tggactgcca cttttaaagg ctcgccttca tttctgactt    960
tggtatttcc cttttttgaaa actatgtgat atgtcacttg caacctcat tggaggttct   1020 gaccacagcc actgagaaaa gagttccagt tttctgggga taattaactc acaagggat   1080 tcgactgtaa ctcatgctac attgaaatgc tccatttat ccctgagttt cagggatcgg   1140
atctcccact ccagagactt caatcatgcg tgttgaagct cactcgtgct ttcatacatt   1200
aggaatggtt agtgtgatgt ctttgagaca tagaggtttg tggtatatct gcaaagctcc   1260
tgaacaggta gggggaataa agggctaaga taggaaggtg aggttctttg ttgatgttga   1320
aaatctaaag aagttggtag cttttctaga gatttctgac cttgaaagat taagaaaaag   1380
ccaggtggca tatgcttaac actatataac ttgggaacct taggcaggag ggtgataagt   1440
tcaaggtcag ccagggctat gctggtaaga ctgtctcaaa atccaaagac gaaaataaac   1500
atagagacag caggaggctg gagatgaggc tcggacagtg aggtgcattt tgtacaagca   1560
```

-continued

```
cgaggaatct atatttgatc gtagacccca catgaaaaag ctaggcctgg tagagcatgc   1620
ttgtagactc aagagatgga gaggtaaagg cacaacagat ccccggggct tgcgtgcagt   1680
cagcttagcc taggtgctga gttccaagtc cacaagagtc cctgtctcaa agtaagatgg   1740
actgagtatc tggcgaatgt ccatgggggt tgtcctctgc tctcagaaga gacatgcaca   1800
tgaacctgca cacacacaca cacacacaca cacacacaca cacacacaca cacacacaca   1860
cacatgaaat gaaggttctc tctgtgcctg ctacctctct ataacatgta tctctacagg   1920
actctcctct gcctctgtta agacatgagt gggagcatgg cagagcagtc cagtaattaa   1980
ttccagcact cagaaggctg gagcagaagc gtggagagtt caggagcact gtgcccaaca   2040
ctgccagact cttcttacag aagaaaaagg ttacccgcaa gcagcctgct gtctgtaaaa   2100
ggaaaccctg cgaaaggcaa actttgactg ttgtgtgctc aagggaact gactcagaca    2160 acttctccat tcctggagga aactggagct gtttctgaca gaagaacaac cggtgactgg   2220
gacatacgaa ggcagagctc ttgcagcaat ctatatagtc agcaaaatat tctttgggag   2280
gacagtcgtc accaaattga tttccaagcc ggtggacctc agtttcatct ggcttacagc   2340
tgcctgccca gtgccttga tctgtgctgg ctcccatcta taacagaatc aaattaaata    2400
gaccccgagt gaaatatta agtgagcaga aggtagctt tgttcaaaga ttttttttgca    2460 ttggggagca actgtgtaca tcagaggaca tctgttagtg aggacaccaa aacctgtggt   2520 accgttttt catgtatgaa ttttgttgtt taggttgctt ctagctagct gtggaggtcc    2580
tggctttctt aggtgggtat ggaagggaga ccatctaaca aaatccatta gagataacag   2640
ctctcatgca gaagggaaaa ctaatctcaa atgttttaaa gtaataaaac tgtactggca   2700
aagtactttg agcatattta aa                                            2722
```

<210> SEQ ID NO 30
<211> LENGTH: 280
<212> TYPE: PRT
<213> ORGANISM: Artificial
<220> FEATURE:
<223> OTHER INFORMATION: Mouse human chimeric sequence

<400> SEQUENCE: 30

```
Met Phe Ser Gly Leu Thr Leu Asn Cys Val Leu Leu Leu Gln Leu
1               5                   10                  15

Leu Leu Ala Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Ala Ala Lys Val Thr Pro Ala Gln Thr Ala His Gly Asp Ser
    130                 135                 140

Thr Thr Ala Ser Pro Arg Thr Leu Thr Thr Glu Arg Asn Gly Ser Glu
145                 150                 155                 160
```

```
Thr Gln Thr Leu Val Thr Leu His Asn Asn Asn Gly Thr Lys Ile Ser
                165                 170                 175
Thr Trp Ala Asp Glu Ile Lys Asp Ser Gly Glu Thr Ile Arg Thr Ala
            180                 185                 190
Ile His Ile Gly Val Gly Val Ser Ala Gly Leu Thr Leu Ala Leu Ile
        195                 200                 205
Ile Gly Val Leu Ile Leu Lys Trp Tyr Ser Cys Lys Lys Lys Lys Leu
    210                 215                 220
Ser Ser Leu Ser Leu Ile Thr Leu Ala Asn Leu Pro Pro Gly Gly Leu
225                 230                 235                 240
Ala Asn Ala Gly Ala Val Arg Ile Arg Ser Glu Glu Asn Ile Tyr Thr
                245                 250                 255
Ile Glu Glu Asn Val Tyr Glu Val Glu Asn Ser Asn Glu Tyr Tyr Cys
            260                 265                 270
Tyr Val Asn Ser Gln Gln Pro Ser
        275                 280

<210> SEQ ID NO 31
<211> LENGTH: 1359
<212> TYPE: DNA
<213> ORGANISM: Mus musculus

<400> SEQUENCE: 31
attctgggga ctcaggagtt agaggaagta ccattttaac cgaggagcta aagctatccc      60
tacacagagc tgtccttgga tttcccctgc caagtactca tgttttcagg tcttaccctc     120
aactgtgtcc tgctgctgct gcaactacta cttgcaagta agtctgggcc tgggcctttt     180
caattggagg atgatttcag agtgcaaggc aaagatacca ggatggtcat agtgatgctg     240
tttgtaatag caacctaaat gtccaataat ggggaccggg taaataaatg agacataaca     300
gtaacacaag cagtgagctt aattgaagag cctcatatag actgttggca ttcacagtgc     360
tacagagaaa accaaggcaa acaatcatgt gtgcaagcgt tgtatgtgga cgtatttttaa    420 tgtttgggct ctaggaaggg aagccgtgaa atgtgaagag ttgggagagg agtcatgctt     480
gcagtcatgc ttgcacataa ctttcatgtg ctttgaatgc attgtcatag atgtgtgtgt     540
gtgttattat taaggaattt attttaaact tcaataaaac atatgaggaa tctcaaatat     600
gcaagctact agttttgttt tgtcaggggt tctattcatg acagagggag aggggaagag     660 agggagggggg agagggagga ggagaggggg agaggggggaa agaatgaagt tacctttcct   720
atgctaatta acaggcaact agtctagatt aggtgagcta ttttcctgcc aacaatgccc     780 attttctga atgttaactc cattagctct ggagtcacat tggctcataa ttggagggct      840
gttattctga aaaggagga gggatgtcct gtgtcaagga ccccacaaca cacgaaaact      900
gagagaaatg caagttctca cgtcccatct cagtccaatg gaggcacaca ttttagggaa     960
cgagcctagg tcgcccaggc tggctcaaac tcactacagt tcttcccag gctctttaca    1020 gggatgacag gcttaagtca tcgttcctgg tctggtcatt tcttttctga gagacagttt    1080
tatcactttg gctagcctgg aacttgctat aaagttcagg ctggcctcta gtttaggatt    1140
ttcctgtctc cacctgctga gttccagaat gacaggcctg tgcaatgtta ataaatgttt    1200
aaatgggatt tcttctgcc tctcaaatca gagaatcatt ggcacagcca atcctcctcc     1260
caacagggca gccatagttt cctcatttat tctgtgatgc attgcttgaa gaaatggacc    1320
ctcactgtac tgacctcctt tccttacttt ataggggtca                         1359
```

```
<210> SEQ ID NO 32
<211> LENGTH: 52
<212> TYPE: DNA
<213> ORGANISM: Artificial
<220> FEATURE:
<223> OTHER INFORMATION: PCR primer

<400> SEQUENCE: 32
tttaagaagg agatatacat ggagctcatt ctggggactc aggagttaga gg        52

<210> SEQ ID NO 33
<211> LENGTH: 45
<212> TYPE: DNA
<213> ORGANISM: Artificial
<220> FEATURE:
<223> OTHER INFORMATION: PCR primer

<400> SEQUENCE: 33
gtattccact tctgatgacc ctataaagta aggaaaggag gtcag                45

<210> SEQ ID NO 34
<211> LENGTH: 321
<212> TYPE: DNA
<213> ORGANISM: Homo sapiens

<400> SEQUENCE: 34
tcagaagtgg aatacagagc ggaggtcggt cagaatgcct atctgccctg cttctacacc    60
ccagccgccc cagggaacct cgtgcccgtc tgctggggca aggagcctg tcctgtgttt    120 gaatgtggca acgtggtgct caggactgat gaaagggatg tgaattattg gacatccaga   180
tactggctaa atggggattt ccgcaaagga gatgtgtccc tgaccataga gaatgtgact   240
ctagcagaca gtgggatcta ctgctgccgg atccaaatcc caggcataat gaatgatgaa   300
aaatttaacc tgaagttggt c                                             321

<210> SEQ ID NO 35
<211> LENGTH: 42
<212> TYPE: DNA
<213> ORGANISM: Artificial
<220> FEATURE:
<223> OTHER INFORMATION: PCR primer

<400> SEQUENCE: 35
cttactttat agggtcatca gaagtggaat acagagcgga gg                    42

<210> SEQ ID NO 36
<211> LENGTH: 46
<212> TYPE: DNA
<213> ORGANISM: Artificial
<220> FEATURE:
<223> OTHER INFORMATION: PCR primer

<400> SEQUENCE: 36
ctcacctgct ttgatgacca acttcaggtt aaattttca tcattc                 46

<210> SEQ ID NO 37
<211> LENGTH: 1300
<212> TYPE: DNA
<213> ORGANISM: Artificial
<220> FEATURE:
<223> OTHER INFORMATION: Mus musculus

<400> SEQUENCE: 37
atcaaagcag gtgagtagac ctttccatgt tatcattgtc cgtcagcatc cctgtgagtc    60
```

-continued

```
atgaattcat agaaatagag gatgctcaca tctgacttcc ttagctacag accttgggat      120
gggatgggaa gacatggatt aataggcctc ccctgtgaaa tgcagtggta tagcttccac      180
atgtgtttga actccaggat atggtctaca gaaaaggaag aaagacctag accaagggtt      240
cacaatcctg cctgatcatg agcatcacat ggaaagtctc tgctttctat ctattttaat      300 tgttttatg atatatttt tatcatattt tttcctttcc tccaacttct gattagattt        360
tctccacctt cttactcaca caactttgtg ttctttctgt ctctcaaaca cacagacaca      420
cacacaaatc aaaactcaga acaaacaagc ataatcaata atagaaaaat atctgacaaa      480
acaaagtgca caaatcaaa tggagtatgt tacttctggg taagggaccct actcttgaat      540 gtgactggta tgcccagtga cactccattg gagagaactg gattttctat ttcccagctg      600
gcatcaattg caaatagctt cttagaggag tgggcgctcc ggtctccttc ccctttccag      660
tgctgggatt tcatctggtt tgagtctgtg caagtcttat gagtgctatc attgtctcca      720
tgaacttata tgtagagtag tcccgtttcc tcgaagctat ctattacctc tggctcttac      780
aatctttctg tagagagaat ctcttgtgta gtgtgtggag gcatcacttg tcaagtaaaa      840
gctagtggtc tattagcaaa aggcaggaag taataggtgg gaattctggt tgagagtttg      900
gaactctgga agagagtcag aggcaagaga tttcatcctg ggctctgaga aattcagata      960
catgaaactg agaagaggta accaaccatg tggcagacat agtctaaaat aaatgggtta    1020
tataagttat gagccagtcg gagaacatgc caaagctatg gtctaggtac ttattcatat    1080
ataattaagt ttcagagcca ttattctgga aataaagagg ccaggtagaa aagactgtgg    1140
ctacaaatgg tgtcccacat taggcaccaa atgttgtttt taataaagtc tcaaatgttc    1200
aattttacca ataaagacta gggagccaga tgctggggta atagcctgct agctcagaga    1260
gacagcgaaa gaacccattt gaccttcctc cgcagtagat                          1300
```

<210> SEQ ID NO 38
<211> LENGTH: 41
<212> TYPE: DNA
<213> ORGANISM: Artificial
<220> FEATURE:
<223> OTHER INFORMATION: PCR primer

<400> SEQUENCE: 38

```
aacctgaagt tggtcatcaa agcaggtgag tagacctttc c                          41
```

<210> SEQ ID NO 39
<211> LENGTH: 52
<212> TYPE: DNA
<213> ORGANISM: Artificial
<220> FEATURE:
<223> OTHER INFORMATION: PCR primer

<400> SEQUENCE: 39

```
ttgttagcag ccggatctca gaagcttatc tactgcggag gaaggtcaaa tg              52
```

<210> SEQ ID NO 40
<211> LENGTH: 25
<212> TYPE: DNA
<213> ORGANISM: Artificial
<220> FEATURE:
<223> OTHER INFORMATION: PCR primer

<400> SEQUENCE: 40

```
ctcagagtgc cttgcagggt gtatc                                            25
```

```
<210> SEQ ID NO 41
<211> LENGTH: 25
<212> TYPE: DNA
<213> ORGANISM: Artificial
<220> FEATURE:
<223> OTHER INFORMATION: PCR primer

<400> SEQUENCE: 41
ttgcggaaat ccccatttag ccagt                                              25

<210> SEQ ID NO 42
<211> LENGTH: 28
<212> TYPE: DNA
<213> ORGANISM: Artificial
<220> FEATURE:
<223> OTHER INFORMATION: PCR primer

<400> SEQUENCE: 42
gcaaaggagc ctgtcctgtg tttgaatg                                           28

<210> SEQ ID NO 43
<211> LENGTH: 25
<212> TYPE: DNA
<213> ORGANISM: Artificial
<220> FEATURE:
<223> OTHER INFORMATION: PCR primer

<400> SEQUENCE: 43
cgcaagcacc aagaggagat ggaaa                                              25

<210> SEQ ID NO 44
<211> LENGTH: 25
<212> TYPE: DNA
<213> ORGANISM: Artificial
<220> FEATURE:
<223> OTHER INFORMATION: PCR primer

<400> SEQUENCE: 44
atgttcactc cctgtcaact ggttg                                              25

<210> SEQ ID NO 45
<211> LENGTH: 25
<212> TYPE: DNA
<213> ORGANISM: Artificial
<220> FEATURE:
<223> OTHER INFORMATION: PCR primer

<400> SEQUENCE: 45
tctgctccac atgaccacaa agatg                                              25

<210> SEQ ID NO 46
<211> LENGTH: 25
<212> TYPE: DNA
<213> ORGANISM: Artificial
<220> FEATURE:
<223> OTHER INFORMATION: PCR primer

<400> SEQUENCE: 46
cagagctgtc cttggatttc ccctg                                              25

<210> SEQ ID NO 47
<211> LENGTH: 25
<212> TYPE: DNA
<213> ORGANISM: Artificial
<220> FEATURE:
<223> OTHER INFORMATION: PCR primer
```

<400> SEQUENCE: 47
gactgcaagc atgactcctc tccca                                        25

<210> SEQ ID NO 48
<211> LENGTH: 20
<212> TYPE: DNA
<213> ORGANISM: Artificial
<220> FEATURE:
<223> OTHER INFORMATION: PCR primer

<400> SEQUENCE: 48
cctatctgcc ctgcagttac                                              20

<210> SEQ ID NO 49
<211> LENGTH: 20
<212> TYPE: DNA
<213> ORGANISM: Artificial
<220> FEATURE:
<223> OTHER INFORMATION: PCR primer

<400> SEQUENCE: 49
ttcataagac cagggaactg                                              20

<210> SEQ ID NO 50
<211> LENGTH: 20
<212> TYPE: DNA
<213> ORGANISM: Artificial
<220> FEATURE:
<223> OTHER INFORMATION: PCR primer

<400> SEQUENCE: 50
atctgccctg cttctacacc                                              20

<210> SEQ ID NO 51
<211> LENGTH: 20
<212> TYPE: DNA
<213> ORGANISM: Artificial
<220> FEATURE:
<223> OTHER INFORMATION: PCR primer

<400> SEQUENCE: 51
gcggaaatcc ccatttagcc                                              20

<210> SEQ ID NO 52
<211> LENGTH: 25
<212> TYPE: DNA
<213> ORGANISM: Artificial
<220> FEATURE:
<223> OTHER INFORMATION: PCR primer

<400> SEQUENCE: 52
caacagggca gccatagttt cctca                                        25

<210> SEQ ID NO 53
<211> LENGTH: 25
<212> TYPE: DNA
<213> ORGANISM: Artificial
<220> FEATURE:
<223> OTHER INFORMATION: PCR primer

<400> SEQUENCE: 53
cacatgtgga agctatacca ctgca                                        25

<210> SEQ ID NO 54

<211> LENGTH: 25
<212> TYPE: DNA
<213> ORGANISM: Artificial
<220> FEATURE:
<223> OTHER INFORMATION: PCR primer

<400> SEQUENCE: 54
gtgtttgaat gtggcaacgt ggtgc                                   25

<210> SEQ ID NO 55
<211> LENGTH: 25
<212> TYPE: DNA
<213> ORGANISM: Artificial
<220> FEATURE:
<223> OTHER INFORMATION: PCR primer

<400> SEQUENCE: 55
tggtcacagt gtaccaacga gttgc                                   25

<210> SEQ ID NO 56
<211> LENGTH: 25
<212> TYPE: DNA
<213> ORGANISM: Artificial
<220> FEATURE:
<223> OTHER INFORMATION: PCR primer

<400> SEQUENCE: 56
acagctgaaa gatgggaagt ggagt                                   25

<210> SEQ ID NO 57
<211> LENGTH: 28
<212> TYPE: DNA
<213> ORGANISM: Artificial
<220> FEATURE:
<223> OTHER INFORMATION: PCR primer

<400> SEQUENCE: 57
tcaactcatt ccccatcatg taggttgc                                28

<210> SEQ ID NO 58
<211> LENGTH: 25
<212> TYPE: DNA
<213> ORGANISM: Artificial
<220> FEATURE:
<223> OTHER INFORMATION: PCR primer

<400> SEQUENCE: 58
ccatcacaca acactgatga ggtcc                                   25

<210> SEQ ID NO 59
<211> LENGTH: 25
<212> TYPE: DNA
<213> ORGANISM: Artificial
<220> FEATURE:
<223> OTHER INFORMATION: PCR primer

<400> SEQUENCE: 59
cacatcccca aatgcgtttc attgc                                   25

<210> SEQ ID NO 60
<211> LENGTH: 25
<212> TYPE: DNA
<213> ORGANISM: Artificial
<220> FEATURE:
<223> OTHER INFORMATION: PCR primer

<400> SEQUENCE: 60

-continued cttccacatg agcgtggtca gggcc 25

<210> SEQ ID NO 61
<211> LENGTH: 25
<212> TYPE: DNA
<213> ORGANISM: Artificial
<220> FEATURE:
<223> OTHER INFORMATION: PCR primer

<400> SEQUENCE: 61
ccaagggact attttagatg ggcag 25

<210> SEQ ID NO 62
<211> LENGTH: 26
<212> TYPE: DNA
<213> ORGANISM: Artificial
<220> FEATURE:
<223> OTHER INFORMATION: PCR primer

<400> SEQUENCE: 62
gaagctacaa gctcctaggt aggggg 26

<210> SEQ ID NO 63
<211> LENGTH: 23
<212> TYPE: DNA
<213> ORGANISM: Artificial
<220> FEATURE:
<223> OTHER INFORMATION: PCR primer

<400> SEQUENCE: 63
acgggttggc tcaaaccatt aca 23

<210> SEQ ID NO 64
<211> LENGTH: 20
<212> TYPE: DNA
<213> ORGANISM: Artificial
<220> FEATURE:
<223> OTHER INFORMATION: PCR primer

<400> SEQUENCE: 64
cctggctcac agtgtcagag 20

<210> SEQ ID NO 65
<211> LENGTH: 20
<212> TYPE: DNA
<213> ORGANISM: Artificial
<220> FEATURE:
<223> OTHER INFORMATION: PCR primer

<400> SEQUENCE: 65
cagggctctc ctcgattttt 20

<210> SEQ ID NO 66
<211> LENGTH: 20
<212> TYPE: DNA
<213> ORGANISM: Artificial
<220> FEATURE:
<223> OTHER INFORMATION: PCR primer

<400> SEQUENCE: 66
ccctgctcgt ggtgaccgaa 20

<210> SEQ ID NO 67
<211> LENGTH: 20
<212> TYPE: DNA

```
<213> ORGANISM: Artificial
<220> FEATURE:
<223> OTHER INFORMATION: PCR primer

<400> SEQUENCE: 67
gcaggctctc tttgatctgc                                                    20
```